US005824770A

United States Patent [19]
Georgopoulos

[11] Patent Number: 5,824,770
[45] Date of Patent: Oct. 20, 1998

[54] IKAROS POLYPEPTIDES

[75] Inventor: Katia Georgopoulos, Cambridge, Mass.

[73] Assignee: The General Hospital Corporation, Boston, Mass.

[21] Appl. No.: 465,590

[22] Filed: Jun. 5, 1995

Related U.S. Application Data

[60] Division of Ser. No. 238,212, May 2, 1994, abandoned, which is a continuation-in-part of Ser. No. 121,438, Sep. 14, 1993, abandoned, which is a continuation-in-part of Ser. No. 946,233, Sep. 14, 1992, abandoned.

[51] Int. Cl.$^6$ ........................................................ A61K 38/00
[52] U.S. Cl. ........................... 530/300; 530/350; 435/7.1; 435/69.1; 435/252.3; 435/320.1; 436/503
[58] Field of Search ..................................... 530/300, 350; 35/7.1, 65.1, 252.3, 320.1; 436/503

[56] References Cited

FOREIGN PATENT DOCUMENTS 09406814   3/1994   WIPO .

OTHER PUBLICATIONS

Motnár et al. (1994) Molec–& Cell. Biol. 14:8292–8303.
Adams, B. et al. "Pax–5–encodes the transcription factor BSAP and is expressed in B lymphocytes, the developing CNS, and adult testis" *Genes & Development* 6: 1589–1607 (1992).
Akbar, A.N. et al. "A possible role for bcl–2 in regulating T–cell memory —a 'balancing act' between cell death and survival" *Immunology Today* 14(11):526–531 (1993).
Ardavid, C. et al. "Thymic dendritic cells and T cells develop simultaneously in the thymus from a common precursor population" *Nature* 362: 761–763 (1993).
Asarnow, D.M. et al. "Limited Diversity of γβ Antigen Receptor Genes of Thy–1$^+$ Dendritic Epidermal Cells" *Cell* 55: 837–847 (2 Dec. 1988).
Beg, A.A. and A.S. Baldwin, Jr. "The IkB proteins: multifunctional regulators of Re/NF–kB transcription factors" *Genes & Development* 7: 2064–2070 (1993).
Bigby, M. et al. "Ratio of Langerhan Cells to Thy–1$^+$ Dendritic Epidermal Cells in Murine Epidermis Influences the Intensity of Contact Hypersensitivity" *The Journal of Investigative Dermatology* 89(5): 495–499 (Nov. 1987).
Boise, L. et al. "bcl–x, a bcl–2–Related Gene that Functions as a Dominant Regulator of Apoptotic Cell Death" *Cell* 74: 597–608 (1993).
Bours, V. et al. "The Oncoprotein Bcl–3 Directly Transactivates through kB Motifs via Association with DNA–Binding p50B Homodimers" *Cell* 72: 729–739 (1993).
Cepko, C.L. et al. "Construction and Applications of a Highly Transmissible Murine Retrovirus Shuttle Vector" *Cell* 37: 1053–1062 (1984).
Clevers, H.C. et al. "Transcription factors in early T–cell development" *Immunology Today* 14(2): 591–596 (1993).
Connelly, C.S. et al. "The Role of Transgenic Animals in the Analysis of Various Biological Aspects of Normal and Pathologic States" *Experimental Cell Research* 183: 257–276 (1989).

Delwel, R. et al. Four of the Seven Zinc Fingers of the Evi–1 Myeloid–Transforming Gene Are Required for Sequence–Specific Binding to GA(C/T)AAGA(T/C)AAGATAA, *Molecular and Cellular Biology* 13(7): 4291–4300 (1993).
Ehlich, A. et al. "Immunoglobulin Heavy and Light Chain Genes Rearrange Independently at Early Stages of B Cell Development" *Cell* 72: 695–704 (1993).
Fife, A. et al. "Gram negative septicaemia diagnosed on peripheral blood smear appearances" *Journal of Clinical Pathology* 47: 82–84 (1994).
Fleming, W.H. et al. "Functional Heterogeneity Is Associated with the Cell Cycle Status of Murine Hematopoietic Stem Cells" *J. Cell Biol.* 122: 897–902 (1993).
Franzoso, G. et al "The oncoprotein Bcl–3 can facilitate NF–kB–mediated transactivation by removing inhibiting p50 homodimers from select kB sites" *EMBO J.* 12(10): 3893–3901 (1993).
Furley, A.J. et al. "Developmentally Regulated Rearrangement and Expression of Genes Encoding the T Cell Receptor–T3 Complex" *Cell,* vol. 46: 75–87 (Jul. 1986).
Garni–Wagner, B.A. et al. "Nature Killer Cells in the Thymus" *Journal of Immunology* 144(3): 796–803 (1990).
Georgopoulos, K. "Ikaros an Early Lymphoid Restricted Regulatory Protein a Putative Mediator for T Cell Specficiation" *Biochem. Suppl.* 0 (17 Part A): 158, B 631 (1993).
Georgopoulos, K. et al. "Functionally Distinct Isoforms of the CRE–BP DNA–Binding Protein Mediate Activity of a T–Cell–Specific Enhancer" *Molecular and Cellular Biology* 12(2): 747–757 (Feb. 1992).
Georgopoulos, K. et al. "Ikaros, an Early Lymphoid–Specific Transcription Factor and a Putative Mediator for T Cell Commitment" *Science* 258: 808–812 (Oct. 1992).
Georgopoulos, K. et al. "A T cell–specific enhancer is located in a DNase I–hypersensitive area at the 3' end of the CD3–δ gene" *EMBO J.* 7(8): 2401–2407 (Aug. 1988).
Georgopoulos, K. et al. "Tissue–specific nuclear factors mediate expression of the CD3δ gene during T cell development" *EMBO J.* 9(1): 109–115 (Jan. 1990.).
Godfrey, D.I. and A. Zlotnik "Control points in early T–cell development" *Immunology Today* 14(11): 547–553 (1993).
Gogos, J. et al. "Sequence Discrimination by Alternatively Spliced Isoforms of a DNA Binding Zinc Finger Domain" *Science* 257: 1951–1955 (1992).
Hackett, Jr., J. et al. "Origin and Differentiation of Natural Killer Cells" *Journal of Immunology* 136(8): 3124–3131 (1986).
Hackett, Jr., J. et al. "Transplantable progenitors of natural killer cells are distinct from those of T and B lymphocytes" *Proc. Natl. Acad. Sci USA* 83: 3427–3431 (1986).
Hardy, R.R. et al. "Resolution and Characterization of Pro–B and Pre–Pro–B Cell Stages in Normal Mouse Bone Marrow" *J. Exp. Med.* 173: 1213–1225 (May 1991).

(List continued on next page.)

Primary Examiner—Stephen Walsh
Assistant Examiner—Kenneth A. Sorensen
Attorney, Agent, or Firm—Louis Myers Lahive & Cockfield

[57] ABSTRACT

A purified polypeptide having at least 85% sequence identity with an Ikaros polypeptide or exon.

114 Claims, 25 Drawing Sheets

OTHER PUBLICATIONS

Havran, W and J.P. Allision "Developmentally ordered appearance of thymocytes expressing different T–cells antigen receptors" *Nature* 335: 443–445 (1988).

Havran, W. and J.P. Allison "Origin of Thy–1+ dendritic epidermal cells of adult mice from fetal thymic precursors" *Nature* 344: 68–70 (1990).

Havran, W. et al. "Limited diversity of T–cell receptor γ–chain expression of murine Thy–1+ dendritic epidermal cells revealed by Vγ3–specific monoclonal antibody" *Proc. Natl. Acad. Sci. USA* 86: 4185–4189 (1989).

Haynes, B.F. et al. "Ontogeny of T–cell precursors: a model for the initial stages of human T–cell development" *Immunology Today* 10(3): 87–90(1989).

Hestdal, K. et al. "Characterization and Regulation of RB6–8C5 Antigen Expression on Murine Bone Marrow Cells" *J. Immunol.* 147(1): 22–28 (1 Jul. 1991).

Ho, I.–C. et al. "Human GATA–2: a lineage–restricted transcription factor that regulates the expression of the T cell receptor α gene" *EMBO J.* 10(5): 1187–1192 (1991).

Ho, I.–C. et al. "Sequence–Specific Binding of Human Ets–1 to the T Cell Receptor α Gene Enhancer" *Science* 250: 814–818 (1990).

Hsu, T. et al. "Multiple Zinc Finger Forms Resulting from Developmentally Regulated Alternative Splicing of a Transcription Factor Gene" *Science* 257: 1946–1950 (1992).

Ikuta, K. et al. "A Developmental Switch in Thymic Lymphocyte Maturation Potential Occurs at the Level of Hematopoietic Stem Cells" *Cell* 62: 863–874 (1990).

Ikuta, K. et al. "Lymphocyte Development From Stem Cells" *Annu. Rev. Immunol.* 10: 759–783 (1992).

Jiang, J. and M. Levine "Binding Affinities and Cooperative Interactions with bHLH Activators Delimit Threshold Responses to the Dorsal Gradient Morphogen" *Cell* 72: 741–752 (1993).

Juhlin, L. and W.B. Shelley "New Staining Techniques for the Langerhans Cell" *Acta. Dermatovener.* 57: 289–296 (1977).

Kang, S.–M. et al. "NF–kB Subunit Regulation in Nontransformed CD4+ T Lymphocytes" *Science* 256: 1452–1456 (1992).

Karasuyama, H. et al. "The Expression of $V_{pre-B}/γ5$ Surrogate Light Chain in Early Bone Marrow Precursor B Cells of Normal and B Cell–Deficient Mutant Mice" *Cell* 77: 133–143 (8 Apr. 1994).

Lagasse, E. and I.L. Weissman "BCL–2 Transgene Inhibits Neutrophils Cell Death But Not Their Engulfment By Microphages", *J. Biochem.* 0 (Suppl. 17D): 168 (13–31 Mar. 1993).

Leiden, J.M. et al. "Transcriptional regulation during T–cell development: The α TCR gene as a molecular model" *Immunology Today* 13(1): 22–30 (Jan. 1992).

Lenardo, M. and D. Baltimore "NF–kB: A Pleiotropic Mediator of Inducible and Tissue–Specific Gene Control" *Cell* 58: 227–229 (1989).

Li E. et al., "Targeted Mutation of the DNA Methyltransferase Gene Results in Embryonic Lethality" *Cell* 69: 915–926 (1992).

Li, Y.–S. et al. "The Regulated Expression of B Lineage Associated Genes during B Cell Differentiation in Bone Marrow and Fetal Liver" *J. Exp. Med.* 178: 951–960 (1993).

Liang, P. et al. "Distribution and cloning of eukaryotic mRNAs by means of differential display: refinements and optimization" *Nucleic Acids Research* 21(14): 3269–3275 (1993).

Mann, R. et al. "Construction of a Retrovirus Packaging Mutant and Its Use to Produce Helper–Free Defective Retrovirus" *Cell* 33: 153–159 (1993).

Martin, D.I.K. et al. "Expression of an erythroid transcription factor in megakaryocytic and mast cell lineages" *Nature* 344: 444–447 (1990).

McDonnell, T.J. and S.J. Korsmeyer "Progression from lymphoid hyperplasia to high–grade malignant lymphoma in mice transgenic for the t(14;18)" *Nature* 349: 254–256 (1991).

McDonnell, T.J. et al. "bcl–2–Immunoglobulin Transgenic Mice Demonstrate Extended B Cell Survival and Follicular Lymphoproliferation" *Cell* 57: 79–88 (1989).

Metcalf, D. "The molecular control of cell division, differentiation commitment and maturation in haemopoietic cells" *Nature* 339:27–30 (1989).

Mombaerts, P. et al. "RAG–1–Deficient Mice Have No Mature B and T Lymphocytes" *Cell* 68: 869–877 (1992).

Mucenski, M.L. et al. "A Functional c–myb Gene is Required for Normal Murine Fetal Hepatic Hematopoiesis" *Cell* 65: 677–689 (1991).

Oltvai, Z.N. et al. "Bcl–2 Heterodimerizes In Vivo with a Conserved Homolog, Bax, That Accelerates Programed Cell Death" *Cell* 74: 609–619 (1993).

Oosterwegel, M. et al. "Cloning of Murine TCF–1, a T Cell–specific Transcription Factor Interacting with Functional Motifs in the CD3–ε and T Cell Receptor α Enhancers" *J. Exp. Med.* 173: 1133–1142 (May 1991).

Oosterwegal, M. et al. "Differential expression of the HMG box factors TCF–1 and LEF–1 during murine embryogenesis" *Development* 118: 439–448 (1993).

Philpott, K.L. et al. "Lymphoid Development in Mice Congenitally Lacking T Cell Receptor αβ–Expressing Cells" *Science* 256: 1448–1452 (5 Jun. 1992).

Raulet, D.H. et al. "Control of γβ T–Cell Development" *Immunological Reviews* 120:185–204 (1991).

Read, D. and J.L. Manley "Alternatively spliced transcripts of the *Drosophila tramtrack* gene encode zinc finger proteins with distinct DNA binding specificities" *EMBO J.* 11(3): 1035–1044 (1992).

Rodewald, H.–R. et al. "A Population of Early Fetal Thymocytes Expressing FcγRII/III Contains Precursors of T Lymphocytes and Natural Killer Cells" *Cell* 69: 139–150 (1992).

Rolink, A. and F. Melchers "Molecular and Cellular Origins of B Lymphocyte Diversity" *Cell* 66: 1061–1094 (1991).

Rudnicki, M.A. et al. "Inactivation of MyoD in Mice Leads to Up–Regulation of the Myogenic HLH Gene Myf–5 and Results in Apparently Normal Muscle Development" *Cell* 71: 383–390 (1992).

Sawyers, C.L. et al. "Leukemia and the Disruption of Normal Hematopoiesis" *Cell* 64: 337–350 (1991).

Sentman, C.L. et al. "bcl–2 Inhibits Multiple Forms of Apoptosis but Not Negative Selection in Thymocytes" *Cell* 67: 879–888 (1991).

Shinkai, Y. et al. "RAG–2–Deficient Mice Lack Mature Lymphocytes Owing to Inability to Initiate V(D)J Rearrangement" *Cell* 68: 855–867 (1992).

Singh, H. et al. "Molecular Cloning of an Enhancer Binding Protein: Isolation by Screening of an Expression Library with a Recognition Site DNA" *Cell* 52: 415–423 (12 Feb. 1988).

Skeath, J. et al. "Gene regulation in two dimensions" the proneural achaete and scute genes are controlled by combinations of axis–patterning genes thorugh a common intergenic control region *Genes & Development* 6: 2606–2619 (1992).

Spangrude, G.J. "Enrichment of murine haemopoietic stem cells: divering roads" *Immunology Today* 10(10): 344–350 (1989).

Spangrude, G.J. et al. "Purification and Characterization of Mouse Hematopoeitic Stem Cells" *Science* 241:58–62 (1 Jul. 1988).

Spanopoulou, E. et al. "Functional immunoglobulin transgenes guide ordered B–cell differentiation in Rag–1–deficient mice" *Genes & Development* 8: 1030–1042 (1994).

Travis, A. et al. "LEF–1, a gene encoding a lymphoid–specific with protein, an HMG domain, regulates T–cell receptor α enhancer function" *Genes & Development* 5: 880–894 (1991).

Turner, Jr., C.A. et al. "Blimp–1, a Novel Zinc Finger–Containing Protein that Can Drive the Maturation of B Lymphocytes into Immunoglobulin–Secreting Cells" *Cell* 77: 297–306 (22 Apr. 1994).

van de Wetering, M. et al. "Identification and cloning of TCF–1, a T lymphocyte–specific transcription factor containing a sequence–specific HMG box" *EMBO J.* 10(1): 123–132 (1991).

von Boehmer, H. "The Developmental Biology T Lymphocytes" *Ann. Rev. Immunol.* 6: 309–326 (1988).

Waterman, M.L. et al. "A thymus–specific member of the HMG protein family regulates the human T cell receptor Cα enhancer" *Genes & Development* 5: 656–669 (1991).

Weintraub, H. "The MyoD Family and Myogenesis: Redundancy, Networks, and Thresholds" *Cell* 75: 1241–1244 (31 Dec. 1993).

Xu, Y. et al. "LH–2: A LIM/homeodomain gene expressed in developing lymphocytes and neural cells" *Proc. Natl. Acad. Sci. USA* 90: 227–231 (1993).

Yokoyama, W. M. "Flow Cytometry Using the Bector Dickinson FACSan" in *Current Protocols in Immunology,* J.E. Coligan et al. (Eds.), Brooklyn, NY: Greene Publishing Associates, 5.4.1–5.4.14 (1992).

Zervos, A.S. et al. "Mxi1, a Protein that Specifically Interacts with Max to Bind Myc–Max Recognition Sites" *Cell* 72: 223–232 (1993).

FIG.2A

```
AATTCGTTCT ACCTTCTCTG AACCCCAGTG GTGTGTCAAG GCCGGACTGG GAGCTTGGGG         60

GAAGAGGAAG AGGAAGAGGA ATCTGCGGCT CATCCAGGGA TCAGGGTCCT TCCCAAGTGG        120

CCACTCAGAG GGGACTCAGA GCAAGTCTAG ATTTGTGTGG CAGAGAGAGA CAGCTCTCGT        180

TTGGCCTTGG GGAGGCACAA GTCTGTTGAT AACCTGAAGA CA                          222

ATG GAT GTC GAT GAG GGT CAA GAC ATG TCC CAA GTT TCA GGA AAG GAG         270
Met Asp Val Asp Glu Gly Gln Asp Met Ser Gln Val Ser Gly Lys Glu
 1               5                  10                  15

AGC CCC CCA GTC AGT GAC ACT CCA GAT GAA GGG GAT GAG CCC ATG CCT         318
Ser Pro Pro Val Ser Asp Thr Pro Asp Glu Gly Asp Glu Pro Met Pro
            20                  25                  30
```

FIG. 2B

```
GTC CCT GAG GAC CTG TCC ACT ACC TCT GGA GCA CAG CAG AAC TCC AAG    366
Val Pro Glu Asp Leu Ser Thr Thr Ser Gly Ala Gln Gln Asn Ser Lys
         35                   40                   45

AGT GAT CGA GGC ATG GGT GAA CGG CCT TTC CAG CGG CCT TTC CAG TGC AAC CAG TCT GGG    414
Ser Asp Arg Gly Met Gly Glu Arg Pro Phe Gln Cys Asn Gln Ser Gly
     50                   55                   60

GCC TCC TTT ACC CAG AAA GGC AAC CTC CTG CGG CAC ATC AAG CTG CAC    462
Ala Ser Phe Thr Gln Lys Gly Asn Leu Leu Arg His Ile Lys Leu His
 65                   70                   75                   80

TCG GGT GAG AAG CCC TTC AAA TGC CAT CTT TGC AAC TAT GCC TGC CGC    510
Ser Gly Glu Lys Pro Phe Lys Cys His Leu Cys Asn Tyr Ala Cys Arg
         85                   90                   95

CGG AGG GAC GCC CTC ACC GGC CAC CTG AGG ACG CAC TCC GTT GGT AAG    558
Arg Arg Asp Ala Leu Thr Gly His Leu Arg Thr His Ser Val Gly Lys
         100                  105                  110
```

FIG.2C

```
CCT CAC AAA TGT GGA TAT TGT GGC CGG AGC TAT AAA CAG CGA AGC TCT    606
Pro His Lys Cys Gly Tyr Cys Gly Arg Ser Tyr Lys Gln Arg Ser Ser
        115                 120                 125

TTA GAG GAG CAT AAA GAG CGA TGC CAC AAC TAC TTG GAA AGC ATG GGC    654
Leu Glu Glu His Lys Glu Arg Cys His Asn Tyr Leu Glu Ser Met Gly
        130                 135                 140

CTT CCG GGC GTG TGC CCA GTC ATT AAG GAA GAA ACT AAC CAC AAC GAG    702
Leu Pro Gly Val Cys Pro Val Ile Lys Glu Glu Thr Asn His Asn Glu
145                 150                 155                 160

ATG GCA GAA GAC CTG TGC AAG ATA GGA GCA GAG AGG TCC CTT GTC CTG    750
Met Ala Glu Asp Leu Cys Lys Ile Gly Ala Glu Arg Ser Leu Val Leu
        165                 170                 175

GAC AGG CTG GCA AGC AAT GTC GCC AAA CGT AAG AGC TCT ATG CCT CAG    798
Asp Arg Leu Ala Ser Asn Val Ala Lys Arg Lys Ser Ser Met Pro Gln
        180                 185                 190
```

FIG.2D

```
AAA TTT CTT GGA GAC AAG TGC CTG TCA GAC ATG CCC TAT GAC AGT GCC    846
Lys Phe Leu Gly Asp Lys Cys Leu Ser Asp Met Pro Tyr Asp Ser Ala
195                           200                 205

AAC TAT GAG GAG GAT ATG ATG ACA TCC CAC GTG ATG GAC CAG GCC        894
Asn Tyr Glu Glu Asp Met Met Thr Ser His Val Met Asp Gln Ala
210                 215                       220

ATC AAC AAT GCC ATC AAC TAC CTG GGG GCT GAG TCC CTG CGC CCA TTG    942
Ile Asn Asn Ala Ile Asn Tyr Leu Gly Ala Glu Ser Leu Arg Pro Leu
225                 230                       235                 240

GTG CAG ACA CCC CCC GGT AGC TCC GAG GTG GTG CCA GTC ATC AGC TCC    990
Val Gln Thr Pro Pro Gly Ser Ser Glu Val Val Pro Val Ile Ser Ser
          245                       250                 255

ATG TAC CAG CTG CAC AAG CCC CCC TCA GAT GGC CCC CCA CGG TCC AAC   1038
Met Tyr Gln Leu His Lys Pro Pro Ser Asp Gly Pro Pro Arg Ser Asn
260                       265                       270
```

FIG.2E

```
CAT TCA GCA CAG GAC GCC GTG GAT AAC TTG CTG CTG TCC AAG GCC           1086
His Ser Ala Gln Asp Ala Val Asp Asn Leu Leu Leu Ser Lys Ala
        275                 280                 285

AAG TCT GTG TCA TCG GAG CGA GAG GCC TCC CCG AGC AAC AGC TGC CAA       1134
Lys Ser Val Ser Ser Glu Arg Glu Ala Ser Pro Ser Asn Ser Cys Gln
        290                 295                 300

GAC TCC ACA GAT ACA GAG AGC AAC GCG GAG GAA CAG CGC AGC GGC CTT       1182
Asp Ser Thr Asp Thr Glu Ser Asn Ala Glu Glu Gln Arg Ser Gly Leu
305                 310                 315                 320

ATC TAC CTA ACC AAC CAC ATC AAC CCG CAT GCA CGC AAT GGG CTG GCT       1230
Ile Tyr Leu Thr Asn His Ile Asn Pro His Ala Arg Asn Gly Leu Ala
        325                 330                 335

CTC AAG GAG GAG CAG CGC GCC TAC GAG GTG CTG AGG GCG GCC TCA GAG       1278
Leu Lys Glu Glu Gln Arg Ala Tyr Glu Val Leu Arg Ala Ala Ser Glu
        340                 345                 350
```

FIG.2F

```
AAC TCG CAG GAT GCC TTC CGT GTG GTC AGC ACG AGT GGC GAG CAG CTG       1326
Asn Ser Gln Asp Ala Phe Arg Val Val Ser Thr Ser Gly Glu Gln Leu
            355                 360                 365

AAG GTG TAC AAG TGC GAA CAC TGC CGC GTG CTC TTC CTG GAT CAC GTC       1374
Lys Val Tyr Lys Cys Glu His Cys Arg Val Leu Phe Leu Asp His Val
    370                 375                 380

ATG TAT ACC ATT CAC ATG GGC TGC CAT GGC TGC CAT GGC TTT CGG GAT       1422
Met Tyr Thr Ile His Met Gly Cys His Gly Cys His Gly Phe Arg Asp
385                 390                 395                 400

CCC TTT GAG TGT AAC ATG TGT GGT TAT CAC AGC CAG GAC AGG TAC GAG       1470
Pro Phe Glu Cys Asn Met Cys Gly Tyr His Ser Gln Asp Arg Tyr Glu
                405                 410                 415
```

FIG. 2G

```
TTC TCA TCC CAT ATC ACG CGG GGG GAG CAT CGT TAC CAC CTG AGC    1515
Phe Ser Ser His Ile Thr Arg Gly Glu His Arg Tyr His Leu Ser
            420                     425                 430

TAAACCCAGC CAGGCCCCAC TGAAGCACAA AGATAGCTGG TTATGCCTCC TTCCCGGCAG   1575

CTGGACCCCAC AGCGGACAAT GTGGGAGTGG ATTTGCAGGC AGCATTTGTT CTTTTATGTT  1635

GGTTGTTTGG CGTTTCATTT GCGTTGGAAG ATAAGTTTTT AATGTTAGTG ACAGGATTGC   1695

ATTGCATCAG CAACATTCAC AACATCCATC CTTCTAGCCA GTTTTGTTCA CTGGTAGCTG   1755

AGGTTTCCCG GATATGTGGC TTCCTAACAC TCT                               1788
```

(SEQ.ID.NO:2)

FIG.3A

```
AAT GTT AAA GTA GAG ACT CAG AGT GAT GAA GAG AAT GGG CGT GCC TGT   48
Asn Val Lys Val Glu Thr Gln Ser Asp Glu Glu Asn Gly Arg Ala Cys
 1               5                  10                  15

GAA ATG AAT GGG GAA GAA TGT GCG GAG GAT TTA CGA ATG CTT GAT GCC   96
Glu Met Asn Gly Glu Glu Cys Ala Glu Asp Leu Arg Met Leu Asp Ala
                20                  25                  30

TCG GGA GAG AAA ATG AAT GGC TCC CAC AGG GAC CAA GGC AGC TCG GCT  144
Ser Gly Glu Lys Met Asn Gly Ser His Arg Asp Gln Gly Ser Ser Ala
        35                  40                  45

TTG TCG GGA GTT GGA GGC ATT CGA CTT CCT AAC GGA AAA CTA AAG TGT  192
Leu Ser Gly Val Gly Gly Ile Arg Leu Pro Asn Gly Lys Leu Lys Cys
    50                  55                  60

GAT ATC TGT GGG ATC ATT TGC ATC GGG CCC AAT GTG CTC ATG GTT CAC  240
Asp Ile Cys Gly Ile Ile Cys Ile Gly Pro Asn Val Leu Met Val His
65                  70                  75                  80
```

FIG. 3B

```
AAA AGA AGC CAC ACT GGA GAA CGG CCC TTC CAG TGC AAT CAG TGC GGG    288
Lys Arg Ser His Thr Gly Glu Arg Pro Phe Gln Cys Asn Gln Cys Gly
             85                      90                      95

GCC TCA TTC ACC CAG AAG GGC AAC CTG CTC CGG CAC ATC AAG CTG CAT    336
Ala Ser Phe Thr Gln Lys Gly Asn Leu Leu Arg His Ile Lys Leu His
            100                     105                     110

TCC GGG GAG AAG CCC TTC AAA TGC CAC CTC TGC AAC TAC GCC TGC CGC    384
Ser Gly Glu Lys Pro Phe Lys Cys His Leu Cys Asn Tyr Ala Cys Arg
            115                     120                     125

CGG AGG GAC GCC CTC ACT GGC CAC CTG AGG ACG CAC TCC GTT GGT AAA    432
Arg Arg Asp Ala Leu Thr Gly His Leu Arg Thr His Ser Val Gly Lys
            130                     135                     140

CCT CAC AAA TGT GGA TAT TGT GGC CGA AGC TAT AAA CAG CGA ACG TCT    480
Pro His Lys Cys Gly Tyr Cys Gly Arg Ser Tyr Lys Gln Arg Thr Ser
    145                     150                     155         160
```

FIG.3C

```
TTA GAG GAA CAT AAA GAG CGC TGC CAC AAC TAC TTG GAA AGC ATG GGC    528
Leu Glu Glu His Lys Glu Arg Cys His Asn Tyr Leu Glu Ser Met Gly
                165                 170                 175

CTT CCG GGC ACA CTG TAC CCA GTC ATT AAA GAA GAA ACT AAG CAC AGT    576
Leu Pro Gly Thr Leu Tyr Pro Val Ile Lys Glu Glu Thr Lys His Ser
            180                 185                 190

GAA ATG GCA GAA GAC CTG TGC AAG ATA GGA TCA GAG AGA TCT CTC GTG    624
Glu Met Ala Glu Asp Leu Cys Lys Ile Gly Ser Glu Arg Ser Leu Val
                195                 200                 205

CTG GAC AGA CTA GCA AGT AAT GTC GCC AAA CGT AAG AGC TCT ATG CCT    672
Leu Asp Arg Leu Ala Ser Asn Val Ala Lys Arg Lys Ser Ser Met Pro
            210                 215                 220

CAG AAA TTT CTT GGG GAC AAG GGC CTG TCC GAC ACG CCC TAC GAC AGT    720
Gln Lys Phe Leu Gly Asp Lys Gly Leu Ser Asp Thr Pro Tyr Asp Ser
225                 230                 235                 240
```

FIG.3D

```
GCC ACG TAC GAG AAG GAG AAC GAA ATG ATG AAG TCC CAC GTG ATG GAC
Ala Thr Tyr Glu Lys Glu Asn Glu Met Met Lys Ser His Val Met Asp    768
            245                 250                 255

CAA GCC ATC AAC AAC GCC ATC AAC TAC CTG GGG GCC GAG TCC CTG CGC
Gln Ala Ile Asn Asn Ala Ile Asn Tyr Leu Gly Ala Glu Ser Leu Arg    816
            260                 265                 270

CCG CTG GTG CAG ACG CCC CCG GGC GGT TCC GAG GTG GTC CCG GTC ATC
Pro Leu Val Gln Thr Pro Pro Gly Gly Ser Glu Val Val Pro Val Ile    864
            275                 280                 285

AGC CCG ATG TAC CAG CTG CAC AGG CGC TCG GAG GGC ACC CCG CGC TCC
Ser Pro Met Tyr Gln Leu His Arg Arg Ser Glu Gly Thr Pro Arg Ser    912
            290                 295                 300

AAC CAC TCG GCC CAG GAC AGC GCC GTG GAG TAC CTG CTG CTC TCC
Asn His Ser Ala Gln Asp Ser Ala Val Glu Tyr Leu Leu Leu Ser        960
            305                 310                 315        320
```

FIG. 3E

```
AAG GCC AAG TTG GTG CCC TCG GAG CGC GAG GCG TCC CCG AGC AAC AGC    1008
Lys Ala Lys Leu Val Pro Ser Glu Arg Glu Ala Ser Pro Ser Asn Ser
325                 330                 335

TGC CAA GAC TCC ACG GAC ACC GAG AGC AAC AAC GAG AGC CAG CGC AGC    1056
Cys Gln Asp Ser Thr Asp Thr Glu Ser Asn Asn Glu Ser Gln Arg Ser
        340                 345                 350

GGT CTT ATC TAC CTG ACC AAC CAC ATC GCC CGA CGC CAA CGC GCG GTG    1104
Gly Leu Ile Tyr Leu Thr Asn His Ile Ala Arg Arg Gln Arg Ala Val
355                 360                 365

TCG CTC AAG GAG GAG CAC CGC GCC TAC GAC CTG CTG CGC GCC GCC TCC    1152
Ser Leu Lys Glu Glu His Arg Ala Tyr Asp Leu Leu Arg Ala Ala Ser
370                 375                 380

GAG AAC TCG CAG GAC GCG CTC CGC GTG GTC AGC ACC AGC GGG GAG CAG    1200
Glu Asn Ser Gln Asp Ala Leu Arg Val Val Ser Thr Ser Gly Glu Gln
385                 390                 395                 400
```

FIG.3F

```
ATG AAG GTG TAC AAG TGC GAA CAC TGC CGG GTG CTC TTC CTG GAT CAC    1248
Met Lys Val Tyr Lys Cys Glu His Cys Arg Val Leu Phe Leu Asp His
            405                     410                     415

GTC ATG TAC ACC ATC CAC ATG GGC TGC CAC GGC TTC CGT GAT CCT TTT    1296
Val Met Tyr Thr Ile His Met Gly Cys His Gly Phe Arg Asp Pro Phe
        420                     425                     430

GAG TGC AAC ATG TGC GGC TAC CAC AGC CAG GAC CGG TAC GAG TTC TCG    1344
Glu Cys Asn Met Cys Gly Tyr His Ser Gln Asp Arg Tyr Glu Phe Ser
        435                     440                     445

TCG CAC ATA ACG CGA GGG GAG CAC CGC TTC CAC ATG AGC TAA            1386
Ser His Ile Thr Arg Gly Glu His Arg Phe His Met Ser
        450                     455                     460
```

(SEQ.ID.NO: 3)

FIG. 9A

```
              ↓Ex3
mIk-1   Ala Ser Asn Val Lys Val Glu Thr Gln Ser Asp Glu Glu Asn
hIk-1   Ala Ser Asn Val Lys Val Glu Thr Gln Ser Asp Glu Glu Asn

Gly Arg Ala Cys Glu Met Asn Gly Glu Cys Ala Glu Asp Leu Arg
        Gly Arg Ala Cys Glu Met Asn Gly Glu Cys Ala Glu Asp Leu Arg

Met Leu Asp Ala Ser Gly Glu Lys Met Asn Gly Ser His Arg Asp Gln
        Met Leu Asp Ala Ser Gly Glu Lys Met Asn Gly Ser His Arg Asp Gln

Gly Ser Ser Ala Leu Ser Gly Val Gly Gly Ile Arg Leu Pro Asn Gly
        Gly Ser Ser Ala Leu Ser Gly Val Gly Gly Ile Arg Leu Pro Asn Gly

Lys Leu Lys Cys Asp Ile Cys Gly Ile Val Cys Ile Gly Pro Asn Val
        Lys Leu Lys Cys Asp Ile Cys Gly Ile Ile Cys Ile Gly Pro Asn Val
                                                    ↓Ex4
        Leu Met Val His Lys Arg Ser His Thr Gly Glu Arg Pro Phe Gln Cys
        Leu Met Val His Lys Arg Ser His Thr Gly Glu Arg Pro Phe Gln Cys
```

FIG.9B

```
Asn Gln Ser Gly Ala Ser Phe Thr Gln Lys Gly Asn Leu Leu Arg His
Asn Gln Cys Gly Ala Ser Phe Thr Gln Lys Gly Asn Leu Leu Arg His

Ile Lys Leu His Ser Gly Glu Lys Pro Phe Lys Cys His Leu Cys Asn
Ile Lys Leu His Ser Gly Glu Lys Pro Phe Lys Cys His Leu Cys Asn

Tyr Ala Cys Arg Arg Arg Asp Ala Leu Thr Gly His Leu Arg Thr His
Tyr Ala Cys Arg Arg Arg Asp Ala Leu Thr Gly His Leu Arg Thr His
                ↓Ex5
Ser Val Gly Lys Pro His Lys Cys Gly Tyr Cys Gly Arg Ser Tyr Lys
Ser Val Gly Lys Pro His Lys Cys Gly Tyr Cys Gly Arg Ser Tyr Lys

Gln Arg Ser Ser Leu Glu Glu His Lys Glu Arg Cys His Asn Tyr Leu
Gln Arg Thr Ser Leu Glu Glu His Lys Glu Arg Cys His Asn Tyr Leu
                                                    ↓Ex6
Glu Ser Met Gly Leu Pro Gly  *  Val Cys Pro Val Ile Lys Glu Glu
Glu Ser Met Gly Leu Pro Gly Thr Leu Tyr Pro Val Ile Lys Glu Glu
```

FIG. 9C

```
Thr Asn His Asn Glu Met Ala Glu Asp Leu Cys Lys Ile Gly Ala Glu
Thr Lys His Ser Glu Met Ala Glu Asp Leu Cys Lys Ile Gly Ser Glu

Arg Ser Leu Val Leu Asp Arg Leu Ala Ser Asn Val Ala Lys Arg Lys
Arg Ser Leu Val Leu Asp Arg Leu Ala Ser Asn Val Ala Lys Arg Lys
                                          ↓Ex7
Ser Ser Met Pro Gln Lys Phe Leu Gly Asp Lys Cys Leu Ser Asp Met
Ser Ser Met Pro Gln Lys Phe Leu Gly Asp Lys Gly Leu Ser Asp Thr

Pro Tyr Asp Ser Ala Asn Tyr Glu Lys Glu  *  Asp Met Met Thr Ser
Pro Tyr Asp Ser Ala Thr Tyr Glu Lys Glu Asn Glu Met Met Lys Ser

His Val Met Asp Gln Ala Ile Asn Asn Ala Ile Asn Tyr Leu Gly Ala
His Val Met Asp Gln Ala Ile Asn Asn Ala Ile Asn Tyr Leu Gly Ala
```

FIG.9D

```
Glu Ser Leu Arg Pro Leu Val Gln Thr Pro Pro Gly Ser Ser Glu Val
Glu Ser Leu Arg Pro Leu Val Gln Thr Pro Pro Gly Gly Ser Glu Val

Val Pro Val Ile Ser Ser Met Tyr Gln Leu His Lys Pro Pro Ser Asp
Val Pro Val Ile Ser Pro Met Tyr Gln Leu His Arg  *  Arg Ser Glu

Gly Pro Pro Arg Ser Asn His Ser Ala Gln Asp  *  Ala Val Asp Asn
Gly Thr Pro Arg Ser Asn His Ser Ala Gln Asp Ser Ala Val Glu Tyr

Leu Leu Leu Ser Lys Ala Lys Ser Val Ser Glu Arg Glu Ala
Leu Leu Leu Ser Lys Ala Lys Ser Leu Val Pro Ser Glu Arg Glu Ala

Ser Pro Ser Asn Ser Cys Gln Asp Ser Thr Asp Thr Glu Ser Asn Ala
Ser Pro Ser Asn Ser Cys Gln Asp Ser Thr Asp Thr Glu Ser Asn Asn
```

FIG.9E

```
Glu Glu Gln Arg Ser Gly Leu Ile Tyr Leu Ile Thr Asn His Ile Asn Pro
Glu Glu Gln Arg Ser Gly Leu Ile Tyr Leu Ile Thr Asn His Ile Ala Arg

His Ala Arg Asn Gly Leu Ala Leu Lys Glu Glu Gln Arg Ala Tyr Glu
Arg Ala Gln Arg  *  Val Ser Leu Lys Glu Glu His Arg Ala Tyr Asp

Val Leu Arg Ala Ala Ser Glu Asn Ser Gln Asp Ala Phe Arg Val Val
Leu Leu Arg Ala Ala Ser Glu Asn Ser Gln Asp Ala Leu Arg Val Val

Ser Thr Ser Gly Glu Gln Leu Lys Val Tyr Lys Cys Glu His Cys Arg
Ser Thr Ser Gly Glu Gln Met Lys Val Tyr Lys Cys Glu His Cys Arg

Val Leu Phe Leu Asp His Val Met Tyr Thr Ile His Met Gly Cys His
Val Leu Phe Leu Asp His Val Met Tyr Thr Ile His Met  *   *   *
```

FIG.9F

```
Gly Cys His Gly Phe Arg Asp Pro Phe Glu Cys Asn Met Cys Gly Tyr
Gly Cys His Gly Phe Arg Asp Pro Phe Glu Cys Asn Met Cys Gly Tyr

His Ser Gln Asp Arg Tyr Glu Phe Ser Ser His Ile Thr Arg Gly Glu
His Ser Gln Asp Arg Tyr Glu Phe Ser Ser His Ile Thr Arg Gly Glu

His Arg Tyr His Leu Ser       (SEQ.ID.NO: 5)
His Arg Phe His Met Ser       (SEQ.ID.NO: 3)
```

IKAROS POLYPEPTIDES

This application is a divisional application of Ser. No. 08/238,212 filed on May 2, 1994, abandoned, which in turn is a continuation-in-part application of Ser. No. 08/121,438 filed on Sep. 14, 1993, abandoned; which in turn is a continuation in part application of Ser. No. 07/946,233 filed on Sep. 14, 1992, abandoned. The contents of all of the aforementioned application(s) are hereby incorporated by reference.

BACKGROUND OF THE INVENTION

The invention relates to the Ikaros gene and to the differentiation and generation of T cells.

The generation of the T cell repertoire from a progenitor stem cell proceeds through a differentiation pathway in which the later intrathymic steps are well documented while the early extrathymic events are only poorly characterized. One of the earliest definitive T cell differentiation markers is the CD3δ gene of the CD3/TCR complex.

SUMMARY OF THE INVENTION

The Ikaros gene, a gene active in the early differentiation of lymphocytes, e.g. T cells and B cells, has been discovered. The gene encodes a family of unique zinc finger proteins, the Ikaros proteins. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID No. 5, and amino acid residues 229–461 of the human Ikaros protein represented by SEQ ID No. 3) but differ in the 5' region. The Ikaros family includes all naturally occurring splicing variants which arise from transcription and processing of the Ikaros gene. Five such isoforms are described herein. The Ikaros family also includes other isoforms, including those generated by mutagenesis and/or by in vitro exon shuffling. The naturally occurring Ikaros proteins can bind and activate (to differing extents) the enhancer of the CD3δ gene, and are expressed primarily if not solely in T cells in the adult. The expression pattern of this transcription factor during embryonic development suggests that Ikaros proteins play a role as a genetic switch regulating entry into the T cell lineage. The Ikaros gene is also expressed in the proximal corpus striatum during early embryogenesis in mice.

In general, the invention features, nucleic acid, e.g., DNA, preferably a purified DNA, including (or consisting essentially of) a sequence which encodes a peptide including (or consisting essentially of) one or more Ikaros exons. In preferred embodiments: the Ikaros exon is any of E1/2, E3, E4, E5, E6, or E7; the purified DNA does not encode exon E7.

In other preferred embodiments: the encoded peptide further includes a second Ikaros exon; the second exon is any of E1/2, E3, E4, E5, E6, or E7; the first exon is E7 and the second exon is any of E1/2, E3, E4, E5, E6.

In other preferred embodiments: the encoded peptide further includes a third Ikaros exon; the third exon is any of E1/2, E3, E4, E5, E6, or E7; the first exon is E7, said second exon is E3, and the third exon is E1/2; the peptide is Ikaros isoform 5.

In other preferred embodiments: the encoded peptide further includes a fourth Ikaros exon; the fourth exon is any of E1/2, E3, E4, E5, E6, or E7; the first exon is E7, the second exon is E6, the third exon is E4, and the fourth exon is E1/2; the first exon is E7, the second exon is E4, the third exon is E3, and the fourth exon is E1/2; the peptide is Ikaros isoform 3 or 4.

In other preferred embodiments: the encoded peptide further includes a fifth Ikaros exon; the fifth exon is any of E1/2, E3, E4, E5, E6, or E7; the first exon is E7, the second exon is E6, the third exon is E5, the fourth exon is E4, and the fifth exon is E1/2; the peptide is Ikaros isoform 2.

In preferred embodiments: the encoded peptide further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1.

In preferred embodiments: the sequence of the encoded Ikaros exon is essentially the same as that of a naturally occurring Ikaros exon, or a fragment thereof having Ikaros activity; the DNA sequence which encodes the Ikaros exon is at least 85%, more preferably at least 90%, yet more preferably at least 95%, and most preferably at least 98 or 99% homologous with DNA encoding a naturally occurring Ikaros exon, or a fragment thereof having Ikaros activity, e.g., Ikaros exon encoded by DNA from any of SEQ ID NOS: 2–8; the sequence which encodes an Ikaros exon hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon of any of SEQ ID NOS:2–8, or SEQ ID NO: 153; the amino acid sequence of the encoded Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the encoded Ikaros exon is essentially equal in length to a naturally occurring Ikaros exon, or a fragment thereof having Ikaros activity; the amino acid sequence of the encoded Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:2, SEQ ID NO:3, SEQ ID NO:4, SEQ ID NO:5, SEQ ID NO:6, SEQ ID NO:7, or SEQ ID NO: 8; the encoded Ikaros exon amino acid sequence is the same, or essentially the same, as that of a naturally occurring Ikaros exon, or a fragment of the sequence thereof, e.g., an Ikaros exon described in any of SEQ ID NOS:2–8, and the peptide has Ikaros peptide activity.

In preferred embodiments the Ikaros encoding DNA includes at least two exons and: the DNA can be represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the encoded polypeptide includes at least one exon containing a zinc finger domain; the encoded polypeptide includes at least one exon selected from E3, E4 or E5.

In other embodiments, the Ikaros encoding DNA includes a sequence represented by the general formula {Ex$_1$-

$Ex_2 \ldots Ex_n$} wherein each of $Ex_1$ through $Ex_n$ represents any of the Ikaros Exons 1/2, 3, 4, 5, 6 or 7, and n is an integer from zero to 10, more preferably an integer from zero to 5, In preferred embodiments: the polypeptide is a combination of 2 or more Ikaros exons, the combination of which may or may not naturally occur; the polypeptide includes at least two of said exons and is represented by the formula $Ex_1$-$Ex_2$; the polypeptide includes at least three of said exons and is represented by the formula $Ex_1$-$Ex_2$-$Ex_3$; the polypeptide includes at least four of said exons and is represented by the formula $Ex_1$-$Ex_2$-$Ex_3$-$Ex_4$; the polypeptide includes at least five of said exons and is represented by the formula $Ex_1$-$Ex_2$-$Ex_3$-$Ex_4$-$Ex_5$; the polypeptide includes at least six of said exons and is represented by the formula $Ex_1$-$Ex_2$-$Ex_3$-$Ex_4$-$Ex_5$-$Ex_6$; the polypeptide includes at least one exon containing a zinc finger domain; the polypeptide includes at least one exon selected from E3, E4 or E5.

In preferred embodiments: the exons in the encoded peptide are arranged in the same relative linear order as found in a naturally occurring isoform, e.g., Ikaros isoform 1, e.g., in a peptide having the exons E3 and E7, E3 is located N-terminal to E7; the linear order of the encoded exons is different from that found in a naturally occurring isoform, e.g., in Ikaros isoform 1, e.g., in a peptide having exons E3, E5, and E7, the direction N-terminal to C-terminal end, is E5, E3, E7; the exons in the encoded peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, or 5; e.g. the Ikaros isoform is generated by in vitro exon shuffling.

In another aspect, the invention features, a peptide, preferably a substantially pure peptide, including (or consisting essentially of) one or more Ikaros exons. In preferred embodiments: the Ikaros exon is E1/2, E3, E4, E5, E6, or E7; the peptide does not include exon E7.

In other preferred embodiments: the peptide further includes a second Ikaros exon; the second exon is any of E1/2, E3, E4, E5, E6, or E7; the first exon is E7 and the second exon is any of E1/2, E3, E4, E5, E6.

In other preferred embodiments: the peptide further includes a third Ikaros exon; the third exon is any of E1/2, E3, E4, E5, E6, or E7; the first exon is E7, the second exon is E3, and the third exon is E1/2; the peptide is Ikaros isoform 5.

In other preferred embodiments: the peptide further includes a fourth Ikaros exon; the fourth exon is any of E1/2, E3, E4, E5, E6, or E7; the first exon is E7, the second exon is E4, the third exon is E3, and the fourth exon is E1/2; the first exon is E7, the second exon is E4, the third exon is E3, and the fourth exon is E1/2; the peptide is Ikaros isoform 3 or 4.

In other preferred embodiments: the peptide further includes a fifth Ikaros exon; the fifth exon is any of E1/2, E3, E4, E5, E6, or E7; the first exon is E7, the second exon is E6, the third exon is E5, the fourth exon is E4, and the fifth exon is E1/2; the peptide is Ikaros Isoform 2.

In other preferred embodiments: the peptide further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1.

In preferred embodiments: the sequence of the Ikaros exon is essentially the same as that of a naturally occurring Ikaros exon, or a fragment thereof having Ikaros activity; the amino acid sequence of the Ikaros exon is such that a nucleic acid sequence which encodes it is at least 85%, more preferably at least 90%, yet more preferably at least 95%, and most preferably at least 98 or 99% homologous with a naturally occurring Ikaros exon, or a fragment thereof having Ikaros activity, e.g., Ikaros having an amino acid sequence represented in any of SEQ ID NOS:2–8 or SEQ ID NO:153; the amino acid sequence of the Ikaros exon is such that a nucleic acid sequence which encodes it hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon represented in any of SEQ ID NOS:2–8 the amino acid sequence of the Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the Ikaros exon is essentially equal in length to a naturally occurring Ikaros exon; the amino acid sequence of the Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:2, SEQ ID NO:3, SEQ ID NO:4, SEQ ID NO:5, SEQ ID NO: 6, SEQ ID NO:7, or SEQ ID NO:8; the Ikaros exon amino acid sequence is the same, or essentially the same, as that of a naturally occurring Ikaros exon, or a fragment of the sequence thereof, e.g., an Ikaros exon described in any of SEQ ID NOS:2–8; and the peptide has Ikaros peptide activity; the peptide has Ikaros antagonist activity.

In preferred embodiments: the Ikaros protein comprises a polypeptide represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the polypeptide includes at least one exon containing a zinc finger domain; the polypeptide includes at least one exon selected from E3, E4 or E5.

In preferred embodiments: the exons in the peptide are arranged in the same relative linear order as found in a naturally occurring isoform, e.g., in Ikaros isoform 1, e.g., in a peptide having the exons E3 and E7, E3 is located N-terminal to E7; the linear order of the exons is different from that found in a naturally occurring isoform, e.g., in Ikaros isoform 1, e.g., in a peptide having exons E3, E5, and E7, the direction N-terminal to C-terminal end, is E5, E3, E7; the exons in the peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, or 5; e.g. the Ikaros protein is an isoform generated by in vitro exon shuffling.

Another aspect the invention features a DNA, preferably a purified DNA, which includes (or consists essentially of) a DNA sequence encoding an Ikaros peptide, e.g., an Ikaros peptide having Ikaros activity, e.g., Ikaros isoform 1, 2, 3, 4, or 5, or an Ikaros peptide which is an antagonist of an Ikaros activity. In preferred embodiments: the sequence of the encoded Ikaros peptide is essentially the same as the sequence of a naturally occurring Ikaros peptide, or a fragment thereof having Ikaros activity; the DNA sequence is at least 85%, more preferably at least 90%, yet more preferably at least 95%, and most preferably at least 98 or 99% homologous with DNA encoding a naturally occurring Ikaros peptide, or a fragment thereof having Ikaros activity; e.g., with DNA from any of SEQ ID NOS:2–8; the amino acid sequence of the encoded peptide is such that it can be encoded by a nucleic acid which hybridizes under high or low stringency conditions to a nucleic acid which encodes a peptide with the same, or essentially the same, amino acid sequence as the peptide of any of SEQ ID NOS:2–8 or SEQ ID NO:153; the encoded peptide is at least 30, more preferably at least 40, more preferably at least 50, and most preferably at least 60, 80, 100, or 200 amino acid residues in length; the encoded peptide is at least 50% more preferably at least 60%, more preferably 70%, more preferably 80%, more preferably 90%, and most preferably 95% as long as a naturally occurring Ikaros peptide, or a fragment thereof having Ikaros activity; the encoded peptide is essentially the same length as a naturally occurring Ikaros peptide, or a fragment thereof having Ikaros activity; the encoded peptide is at least 80%, more preferably at least 85%, yet more preferably at least 90%, yet more preferably at least 95%, and a most preferably at least 98 or 99% homologous with an amino acid sequence which is the same, or essentially the same, as a naturally occurring Ikaros peptide, or a fragment thereof having Ikaros activity, e.g., the peptide sequence of any of SEQ ID NOS:2–8 or SEQ ID NO:153; and, the amino acid sequence of the peptide is essentially the same as the sequence of a naturally occurring Ikaros peptide, or a fragment thereof having Ikaros activity, e.g., the sequence, described in any of SEQ ID NOS:2–8 or SEQ ID NO: 153.

Another aspect, the invention features a DNA, preferably a purified DNA, which includes (or consists essentially of) a sequence encoding a peptide of 20 or more amino acids in length, the peptide having at least 90% homology with an amino acid sequence which is the same as the amino acid sequence of any of SEQ ID NOS:2–8, or SEQ ID NO:153. In preferred embodiments: the purified DNA encodes a peptide which is at least 30, more preferably at least 40, more preferably at least 50, and most preferably at least 60, 80, 100, or 200, amino acid residues in length; the encoded peptide is at least 50% more preferably at least 60%, more preferably 70%, more preferably 80%, more preferably 90%, and most preferably 95% as long as a naturally occurring Ikaros peptide, or fragment thereof having Ikaros activity; the encoded peptide is essentially the same length as a naturally occurring Ikaros peptide; a peptide which is at least 80, more preferably at least 85, yet more preferably at least 90, yet more preferably at least 95, and most preferably at least 98 or 99% homologous with an amino acid sequence which is the same, or essentially the same, as a naturally occurring Ikaros peptide, or a fragment thereof having Ikaros activity, e.g., as the amino acid sequence of any of SEQ ID NOS:2–8, SEQ ID NO:153; and, a peptide having one of either an Ikaros activity or an Ikaros antagonist activity.

In another aspect, the invention features, a DNA, preferably a purified DNA, which includes (or consists essentially of) a DNA sequence which hybridizes under high or low stringency to a nucleic acid which encodes a peptide with the same, or essentially the same, amino acid sequence as a naturally occurring Ikaros peptide, e.g., the peptide of any of SEQ ID NOS:2–8, or SEQ ID NO:153. In preferred embodiments: the DNA sequence is at least 85%, more preferably at least 90%, yet more preferably at least 95%, and most preferably at least 98 or 99% homologous with DNA encoding a naturally occurring Ikaros peptide, or a fragment thereof having Ikaros activity, e.g., with DNA from of any of SEQ ID NOS:2–8; the purified DNA encodes a peptide at least 30, more preferably at least 40, more preferably at least 50, and most preferably at least 60, 80, 100, or 200 amino acid residues in length; the encoded peptide is at least 50% more preferably at least 60%, more preferably 70%, more preferably 80%, more preferably 90%, and most preferably 95% as long as a naturally occurring Ikaros peptide, or fragment thereof having Ikaros activity; the encoded peptide is essentially the same length as a naturally occurring Ikaros peptide; the purified DNA encodes a peptide at least 80, more preferably at least 85, yet more preferably at least 90, yet more preferably at least 95, and most preferably at least 98 or 99% homologous with an amino acid sequence which is the same, or essentially the same, as a naturally occurring Ikaros peptide, e.g., the amino acid sequence of any of SEQ ID NOS:2–8 or SEQ ID NO:153; and, the purified DNA encodes a peptide having essentially the same amino acid sequence, or a fragment of the amino acid sequence, described in SEQ ID NOS:2–8 or SEQ ID NO:153.

In another aspect, the invention includes a vector which includes DNA of the invention, preferably a purified DNA of the invention, which encodes a peptide of the invention.

The invention also includes: a cell, e.g., a cultured cell or a stem cell, containing purified Ikaros-protein-encoding-DNA; a cell capable of expressing an Ikaros protein; a cell capable of giving rise to a transgenic animal or to a homogeneous population of hemopoietic cells, e.g., lymphoid cells, e.g., T cells; an essentially homogeneous population of cells, each of which includes purified Ikaros-protein-encoding-DNA; and a method for manufacture of a peptide of the invention including culturing a cell which includes a DNA, preferably a purified DNA, of the invention in a medium to express the peptide.

In another aspect, the invention features a peptide of the invention, preferably a substantially pure peptide of the invention, e.g.: a peptide having Ikaros activity, e.g., Ikaros isoform 1, 2, 3, 4, or 5; a peptide having Ikaros antagonistic activity, e.g. able to inhibit at least one biological activity of a naturally occurring Ikaros, e.g. any of isoforms or 1,2,3,4 or 5. In preferred embodiments: the sequence of the encoded Ikaros peptide is essentially the same as the sequence of a naturally occurring Ikaros peptide, or a fragment thereof having Ikaros activity; the sequence of the peptide is such that it is encoded by a DNA sequence at least 85%, more preferably at least 90%, yet more preferably at least 95%, and most preferably at least 98 or 99% homologous with DNA encoding a naturally occurring Ikaros peptide, or a fragment thereof having Ikaros activity; e.g., with DNA from any of SEQ ID NOS:2–8; the amino acid sequence of the peptide having Ikaros activity or Ikaros antagonistic activity is such that it can be encoded by a nucleic acid which hybridizes under high or low stringency conditions to a nucleic acid which encodes a peptide with the same, or essentially the same, amino acid sequence as the peptide of any of SEQ ID NOS:2–8, or SEQ ID NO:153; the peptide is at least 30, more preferably at least 40, more preferably at least 50, and most preferably at least 60, 80, 100, or 200 amino acid residues in length; the peptide is at least 50% more preferably at least 60%, more preferably 70%, more preferably 80%, more preferably 90%, and most preferably 95% as long as a naturally occurring Ikaros peptide, or fragment thereof having Ikaros activity; the peptide is essentially the same length as a naturally occurring Ikaros peptide, or a fragment thereof having Ikaros activity; the peptide is at least 80%, more preferably at least 85%, yet more preferably at least 90%, yet more preferably at least 95%, and a most preferably at least 98 or 99% homologous with an amino acid sequence which is the same, or essentially the same, as a naturally occurring Ikaros peptide, or a fragment thereof having Ikaros activity, e.g., the peptide sequence of any of SEQ ID NOS:2–8, or SEQ ID NO: 153; and, the amino acid sequence of the peptide is essentially the same as the sequence of a naturally occurring Ikaros peptide, or a fragment thereof having Ikaros activity, e.g., the sequence, described in SEQ ID NOS:2–8.

In preferred embodiments a peptide of the invention, preferably a purified peptide of the invention, is produced by expression of a DNA of the invention, preferably a purified DNA of the invention.

In another aspect, the present invention features recombinant Ikaros proteins which are encoded by genes derived from vertebrate organisms (e.g. a mammal, e.g. a human, a mouse or a pig) and which is capable of functioning in one of either role of an agonist or an antagonist of at least one biological activity of a naturally occurring Ikaros protein. The term "recombinant protein" refers to a Ikaros protein of the present invention which is produced by recombinant DNA techniques, wherein generally DNA encoding the Ikaros protein is inserted into a suitable expression vector which is in turn used to transform a host cell to produce the heterologous protein. Moreover, the phrase "derived from", with respect to a recombinant gene encoding the recombinant Ikaros, is meant to include within the meaning of "recombinant protein" those proteins having an amino acid sequence of a naturally occurring Ikaros isoform, or an amino acid sequence similar thereto which is generated by, for example, mutations including substitutions and deletions of a naturally occurring Ikaros isoform. Recombinant proteins preferred by the present invention, in addition to native vertebrate Ikaros proteins, are at least 85%, more preferably at least 90%, yet more preferably at least 95%, and most preferably at least 98 or 99% homologous with an amino acid sequence selected from the group consisting of any of SEQ ID NOS: 2–8, e.g. a protein represented by the general formula of SEQ ID NO:153.

In particular, recombinant Ikaros protein, as used herein, includes a protein of the same or similar sequence as a naturally occurring Ikaros protein (e.g. a protein having an amino acid sequence found in any of SEQ ID NOS: 2–8) but lacking amino acid sequences at either or both of its N-terminal and C-terminal ends. Examples of such proteins include, but are not limited to, Ikaros isoforms which lack either exon 1, or exon 7, or both. In other exemplary embodiments, the recombinant proteins are truncation mutants. In preferred embodiments, the truncation mutants comprise at least 50–60 amino acid residues, more preferably 90–100 amino acid residues, and most preferably at least 150 amino acid residues of an Ikaros protein, or variant thereof, while retaining the activity of either an Ikaros agonist or an Ikaros antagonist.

The present invention further pertains to recombinant Ikaros proteins which are encoded by genes derived from a vertebrate organism and which have amino acid sequences evolutionarily related to naturally occurring Ikaros protein. Such recombinant Ikaros proteins preferably are capable of functioning in one of either role of an agonist of antagonist of at least one biological activity of a vertebrate Ikaros. The term "evolutionarily related to", with respect to amino acid sequences of the present recombinant Ikaros proteins, refers to vertebrate Ikaros proteins having amino acid sequences which have arisen naturally. The term "evolutionarily related to" also refers to mutational variants of naturally occurring Ikaros proteins which are derived, for example, by combinatorial mutagenesis or in vitro exon shuffling. In an illustrative embodiment the recombinant Ikaros protein is an isoform encoded by a recombinant Ikaros gene generated through permutation of an exon order relative to a naturally occurring Ikaros protein, e.g. of SEQ ID NOS:2–8, e.g. of any exons 1/2, 3, 4, 5, 6, 7, e.g. wherein two different exons are permuted in sequential order relative to a naturally occurring Ikaros isoforms, e.g. when an Ikaros exon is present two or more times in the recombinant Ikaros gene.

The invention also includes substantially pure preparation of an antibody, preferably a monoclonal antibody directed against an Ikaros protein; a therapeutic composition including an Ikaros protein and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering a therapeutically-effective amount of an Ikaros peptide to the animal.

In another aspect, the invention features a method for treating an animal, e.g., a human, a mouse, a transgenic animal, or an animal model for an immune system disorder, e.g., a T or B cell related disorder, e.g., a nude mouse or a SCID mouse including administering to the animal cells selected, e.g., selected in vitro, for the expression of a product of the Ikaros gene, e.g., hematopoietic stem cells, e.g., cells transformed with Ikaros-peptide-encoding DNA, e.g., hematopoietic stem cells transformed with Ikaros-peptide-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering to the animal a nucleic acid encoding an Ikaros peptide and expressing the nucleic acid.

In another aspect, the invention features a method of evaluating the effect of a treatment, e.g., a treatment designed to promote or inhibit hematopoiesis, including carrying out the treatment and evaluating the effect of the treatment on the expression of the Ikaros gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including examining the subject for the expression of the Ikaros gene, non-wild type expression or mis-expression being indicative of risk.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including providing a nucleic acid sample from the subject and determining if the structure of an Ikaros gene allele of the subject differs from wild type.

In preferred embodiments: the determination includes determining if an Ikaros gene allele of the subject has a gross chromosomal rearrangement; the determination includes sequencing the subject's Ikaros gene.

In another aspect, the invention features, a method of evaluating an animal or cell model for an immune disorder, e.g., a T cell related disorder, e.g., a disorder characterized by a shortage of T or B cells, including determining if the Ikaros gene in the animal or cell model is expressed at a predetermined level or if the Ikaros gene is mis-expressed. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an Ikaros gene or Ikaros protein encoding DNA. In preferred embodiments: the Ikaros gene or DNA includes a deletion, e.g. a deletion of all or part of one or more Ikaros exons, e.g., a deletion of all or part of exon E7 or a deletion of all or part of exons E3 or E4, or is otherwise mis-expressed; the Ikaros gene encodes an Ikaros protein which is a competitive antagonist of a naturally occurring Ikaros protein.

In another aspect, the invention features a method of expressing a heterologous gene, e.g., in a cell e.g., a stem cell, including placing the gene under the control of an Ikaros-responsive control element, and contacting the Ikaros-responsive control element with an Ikaros protein.

In preferred embodiments: the Ikaros-responsive control element includes an enhancer, e.g., an δA element, an NFKB element, or one of the Ikaros binding sequences, e.g., one of the consensus sequences, disclosed herein; the Ikaros-responsive control element includes the regulatory region of the CD3δ gene; the heterologous gene and the Ikaros-responsive control element are carried on a vector; the method further includes the step of transforming a cell with a vector which includes a heterologous gene under the control of an Ikaros-responsive control agent; the heterologous gene is expressed in a cell which normally includes or expresses an Ikaros protein.

In another aspect, the invention features a method of expressing a gene under the control of an Ikaros-responsive control element in a cell including administering an Ikaros protein to the cell.

In preferred embodiments: the method further includes transforming the cell with DNA which encodes an Ikaros protein to supply an Ikaros protein; the gene is a heterologous gene.

In another aspect, the invention features a method for treating an animal, e.g., a human, a mouse, a transgenic animal, or an animal model for a disorder of the nervous system, e.g., a disorder of the corpus striatum, e.g., Alzheimer's disease, immune system disorder, including administering a therapeutically effective amount of an Ikaros protein to the animal.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal cells selected, e.g., selected in vitro, for the expression of a product of the Ikaros gene, e.g., hematopoietic stem cells, e.g., cells transformed with Ikaros-protein-encoding DNA, e.g., hematopoietic stem cells transformed with Ikaros-protein-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered: the cells are taken from an animal which is of the same species as is the animal to which they are administered.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal a nucleic acid encoding an Ikaros peptide and expressing the nucleic acid.

In another aspect, the invention features a method of evaluating the effect of a treatment for a disorder of the nervous system, e.g., a disorder of the corpus striatum, e.g., Alzheimer's disease, including administering the treatment and evaluating the effect of the treatment on the expression of the Ikaros gene.

In preferred embodiments the treatment is administered: to an animal, e.g., a human, a mouse, a transgenic animal, or an animal model for a disorder of the nervous system, e.g., a disorder of the corpus striatum, e.g., Alzheimer's disease, or a cell, e.g., a cultured stem cell.

In another aspect, the invention features a method for determining if a subject, e.g., a human, is at risk for a disorder related to mis-expression of the Ikaros gene, e.g., a disorder of the nervous system, e.g., a disorder of the corpus striatum, e.g., Alzheimer's disease, including examining the subject for the expression of the Ikaros gene, non-wild type expression or mis-expression being indicative of risk.

In another aspect, the invention features a method for determining if a subject, e.g., a human, is at risk for a disorder related to mis-expression of the Ikaros gene, e.g., a disorder of the nervous system, e.g., a disorder of the corpus striatum, e.g., Alzheimer's disease, including providing a nucleic acid sample from the subject and determining if the structure of an Ikaros gene allele of the subject differs from wild type.

In preferred embodiments: the determination includes determining if an Ikaros gene allele of the subject has a gross chromosomal rearrangement; the determination includes sequencing the subject's Ikaros gene.

In another aspect, the invention features, a method of evaluating an animal or cell model for a disorder of the nervous system, e.g., a disorder of the corpus striatum, e.g., Alzheimer's disease, including determining if the Ikaros gene in the animal or cell model is expressed at a predetermined level or if the Ikaros gene is mis-expressed.

In preferred embodiments: the predetermined level is lower than the level in a wild type or normal animal; the predetermined level is higher than the level in a wild type or normal animal.

In another aspect, the invention features, a method of inhibiting an interaction, e.g., binding, between a protein, e.g., a first Ikaros isoform, and a DNA sequence, e.g., a DNA sequence under the control of a δA sequence, an NKFB sequence, a sequence which corresponds to an Ikaros binding oligonucleotide described herein, or a site present in the control region of a lymphocyte restricted gene, e.g., TCR-α, -β, or -δ, CD3 -δ, -ε, -65 genes, the SL3 gene, or the HIV LTR gene. The methods includes contacting the DNA sequence with an effective amount of a second Ikaros isoform, or with a DNA binding fragment encoding an Ikaros isoform, e.g., of the second Ikaros isoform, e.g. of an Ikaros antagonist isoform.

In preferred embodiments: the fragment is deleted for or part of an Ikaros exon, e.g., for all or part of E1/2, E3, E4, E5, E6, or E7; the antagonist contains one or more point mutations relative to a naturally occurring Ikaros isoform; the antagonist comprises at least two different exons which are sequentially oriented, in the antagonist, in a permuted (e.g. non wild-type) fashion relative to naturally occurring Ikaros isoforms (e.g. any of SEQ. NOS: 2–8); the antagonist comprises at least two of the same Ikaros exon.

In another aspect, the invention features, a method of inhibiting an interaction, e.g., binding, between a protein, e.g., a first Ikaros isoform, and a DNA sequence, e.g., a δA sequence, an NKFB sequence, a sequence which corresponds to an Ikaros binding oligonucleotide described herein, or a site present in the control region of a lymphocyte restricted gene, e.g., TCR-α, -β, or -δ, CD3 -δ, -ε, -γ genes, the SL3 gene, or the HIV LTR gene. The methods includes contacting the protein with an effective amount of an Ikaros binding oligonucleotide. In preferred embodiments the oligonucleotide includes a sequence chosen from, IK-BS1, IK-BS2, IK-BS3, IK-BS4, IK-BS5, IK-BS6, IK-BS7, IK-BS8, or IK-BS9.

In preferred embodiments: the oligonucleotide preferentially binds to a first Ikaros isoform; the oligonucleotide preferentially binds to a second Ikaros isoform.

In another aspect the invention includes an Ikaros binding oligonucleotide, e.g., IK-BS1, IK-BS2, IK-BS3, IK-BS4, IK-BS5, IK-BS6, IK-BS7, IK-BS8, or IK-BS9. In preferred embodiments the oligonucleotide contains at least two, three, four, or five copies of one of the Ikaros binding oligonucleotide sequences disclosed herein.

In another aspect, the invention features a method of attenuating the binding of a first Ikaros isoform to target DNA. The method includes contacting the target DNA with an effective amount of a second Ikaros isoform, or with a DNA binding fragment of said second isoform. The second Ikaros isoform can be, for example, an antagonists isoform of Ikaros, e.g. an Ikaros isoform generated point mutation, e.g. an Ikaros isoform generated by in vitro exon shuffling.

Heterologous gene, as used herein, is a gene which is not normally under the control of an Ikaros responsive control element.

An Ikaros-responsive control element, as used herein is a region of DNA which, when present upstream or downstream from a gene, results in regulation, e.g., increased transcription of the gene in the presence of an Ikaros protein.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inserted by artifice into a cell and becomes a part of the genome of the animal which develops in whole or part from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at a prenatal, e.g., an embryonic stage.

An enhancer region is defined as a cis-acting DNA sequence capable of increasing transcription from a promoter that is located either upstream or downstream of the enhancer region. Such DNA sequences are well known to those skilled in the art of eukaryotic gene expression.

A substantially pure preparation of a peptide is a preparation which is substantially free of one or more of the peptides with which it naturally occurs in a cell. A substantially pure preparation of a non-naturally occurring peptide is one which is at least 10% by weight of the peptide of interest. In a preferred embodiment, a substantially pure preparation further lacks any nucleic acids, such as oligonucleotides, which bind to the subject Ikaros protein.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of the tissue specificity of expression, e.g., increased or decreased expression (as compared with wild type) in a predetermined cell type or tissue type; a pattern of expression that differs from wild type in terms of the size, amino acid sequence, post-translational modification, or a biological activity of an Ikaros gene product; a pattern of expression that differs from wild type in terms of the effect of an environmental stimulus or extracellullar stimulus on expression of the gene, e.g., a pattern of increased or decreased expression (as compared with wild type) in the presence of an increase or decrease in the strength of the stimulus; or a pattern of isoform expression which differs from wildtype.

The terms peptide, protein, and polypeptide are used interchangeably herein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity. "Ikaros antagonists", as used herein, refers to Ikaros isoforms arising naturally or by mutagenesis (including in vitro shuffling) which can inhibit at least one biological activity of a naturally occurring Ikaros protein. In preferred embodiments, the Ikaros antagonist is an inhibitor of: Ikaros-mediated transcriptional activation, e.g. it is a competitive inhibitor of Ikaros binding to Ikaros responsive elements, such as IK-BS1, IK-BS2, IK-BS4, IK-BS5, IK-BS6, IK-BS7, IK-BS8, or IK-BS9; or it is an inhibitor of protein-protein interations of transcriptional complexes formed with naturally occurring Ikaros isoforms.

As used herein, the term "exon", refers to those gene (e.g. DNA) sequences which are transcribed and processed to form mature messenger RNA (mRNA) encoding an Ikaros protein, or portion thereof, e.g. Ikaros coding sequences, and which, at the chromosomal level, are interrupted by intron sequences. Exemplary exons of the subject Ikaros proteins and genes include: with reference to SEQ ID NO:5 (mIk-1), the nucleotide sequence encoding exon 1/2 (E1/2) corresponding to Met-1 through Met-53; the nucleotide sequence encoding exon 3 (E3) corresponding to Ala-54 through Thr-140; the nucleotide sequence encoding exon 4(E4) corresponding to Gly-141 through Ser-196; the nucleotide sequence encoding exon 5 (E5) corresponding to Val-197 through Pro-237; the nucleotide sequence encoding exon 6 (6) corresponding to Val-238 through Leu-282; the nucleotide sequence encoding exon 7 (E7) corresponding to Gly-283 through Ser-518; with reference to SEQ ID NO:3 (hIk-1), the nucleotide sequence encoding exon 3 (E3) corresponding to Asn-1 through Thr-85; the nucleotide sequence encoding exon 4 (E4) corresponding to Gly-86 through Ser-141; the nucleotide sequence encoding exon 5 (E5) corresponding to Val-142 through Pro-183; the nucleotide sequence encoding exon 6 (6) corresponding to Val-184 through Leu-228; the nucleotide sequence encoding exon 7 (E7) corresponding to Gly-229 through Ser-461. The term "intron" refers to a DNA sequence present in a given Ikaros gene which is not translated into protein and is generally found between exons. The term "gene" refers to a region of chromosomal DNA which contains DNA sequences encoding an Ikaros protein, including both exon and intron sequences. A "recombinant gene" refers to nucleic acid encoding an Ikaros protein and comprising Ikaros exon sequence, though it may optionally include intron sequences which are either derived from a chromosomal Ikaros gene or from an unrelated chromosomal gene. An exemplary recombinant gene is a nucleic acids having a sequence represented by any of SEQ ID NOS:2–8 or 153.

The term "Ikaros responsive element" or "IK-RE", refers to nucleic acid sequences which, when placed in proximity of a gene, act as transcriptional regulatory elements which control the level of transcription of the gene in an Ikaros protein-dependent manner. Exemplary IK-RE, as described below, include IK-BS 1, IK-BS2, IK-BS4, IK-BS5, IK-BS6, IK-BS7, IK-BS8, or IK-BS9.

The invention is useful for identifying T cells; identifying cells which can develop into T cells; and generally, in the investigation of hemopoiesis, e.g., in the differentiation of progenitor stem cells into T cells. The role of the Ikaros gene and its products can be studied, e.g., in cells, e.g., cultured cells, transformed with the Ikaros gene or fragments thereof, or in transgenic animals. The invention is also useful for: promoting the expression of markers of cell lineage, e.g., CD3δ genes; enhancing the ability of a cell, e.g., a stem cell, to develop into a T cell; screening individuals at risk for genetic T cell disorders, e.g., leukemia; and treating immune disorders (e.g., immunodeficiencies, e.g., AIDS, or chemical, drug, or radiation induced immunodeficiencies, or cancers, e.g., leukemia) characterized by a shortage of T cells; for investigating the structure and expression of the Ikaros gene or iso forms of the gene product; for investigating species or tissue differences in the expression of the Ikaros gene or its isoforms; for investigating the structure and function of DNA binding proteins; for studying the structure and function of zinc finger containing proteins; for the construction of transgenic animals; for inhibiting the binding of Ikaros to a target molecule; for studying the relative affinities of Ikaros isoforms for target DNA; and for searching for or manipulating the expression of genes under the control of Ikaros isoforms.

Other features and advantages of the invention will be apparent from the following description and from the claims.

DETAILED DESCRIPTION

The drawings are first briefly described.

Drawings

FIG. 2A through FIG. 2G is a map of the DNA sequence of a murine Ikaros cDNA and the desired amino acid sequence encoded thereby (SEQ ID NO:2).

FIG. 3A through FIG. 3F is a partial sequence of a human Ikaros cDNA (SEQ ID NO:3).

Figure 5:
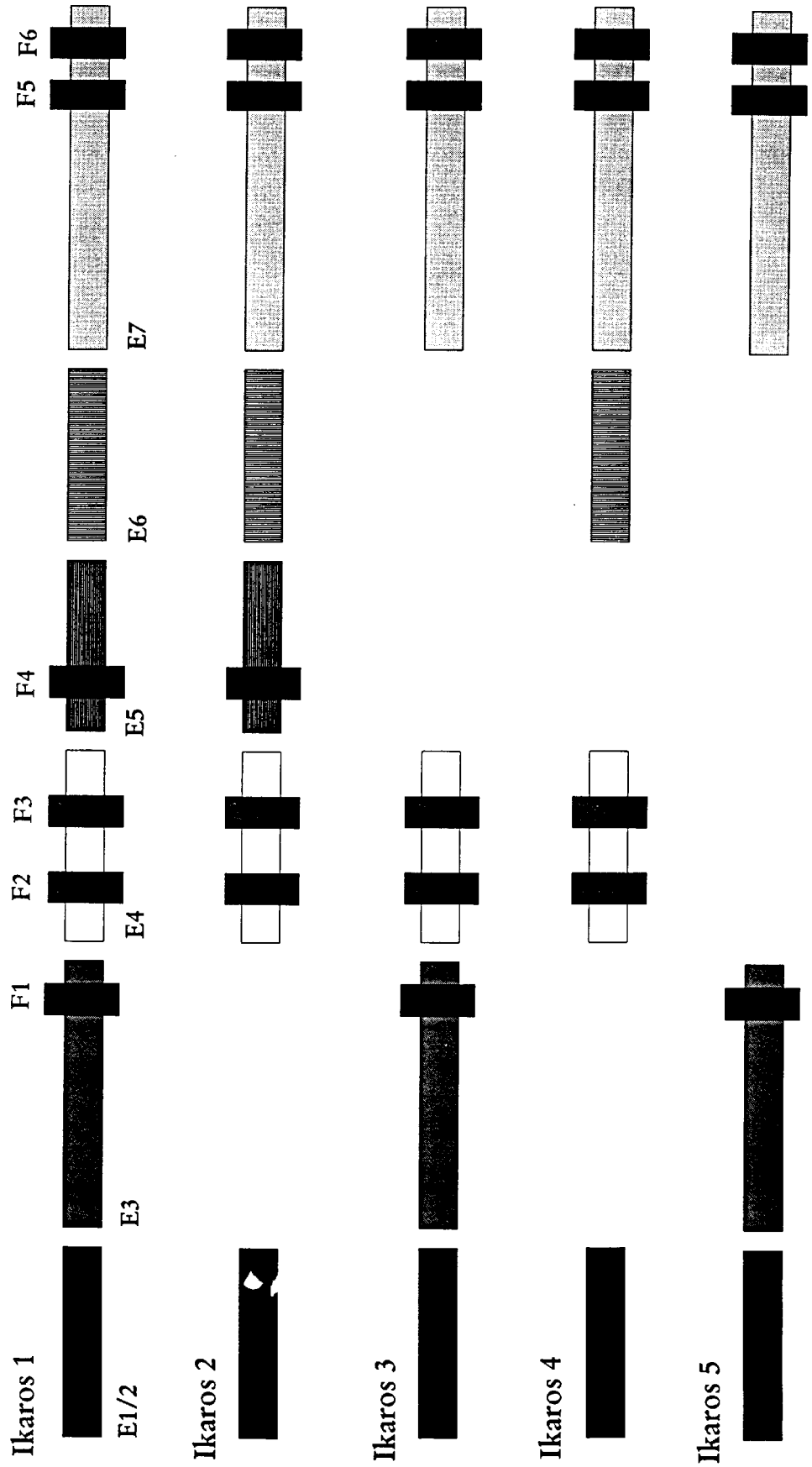

FIG. 5 is a diagram of exon usage in the Ikaros 1–5 cDNAs. Exon numbers are indicated at the bottom left hand corner of each box (Ex). Zinc finger modules are shown on top of the encoding exons (Fx).

Figure 6:
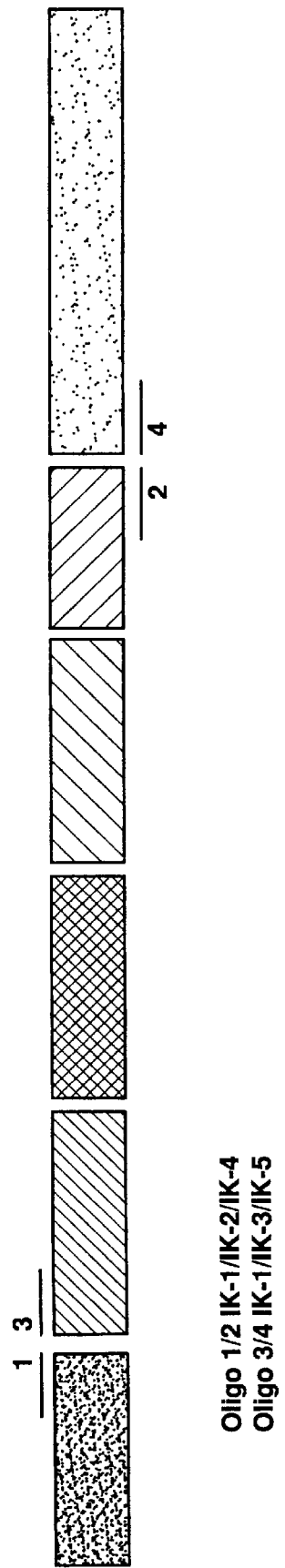

FIG. 6 is a depiction of the exon organization at the Ikaros locus indicating primer sets 1/2 and 3/4 used for amplification of the respective isoforms.

Figure 7:
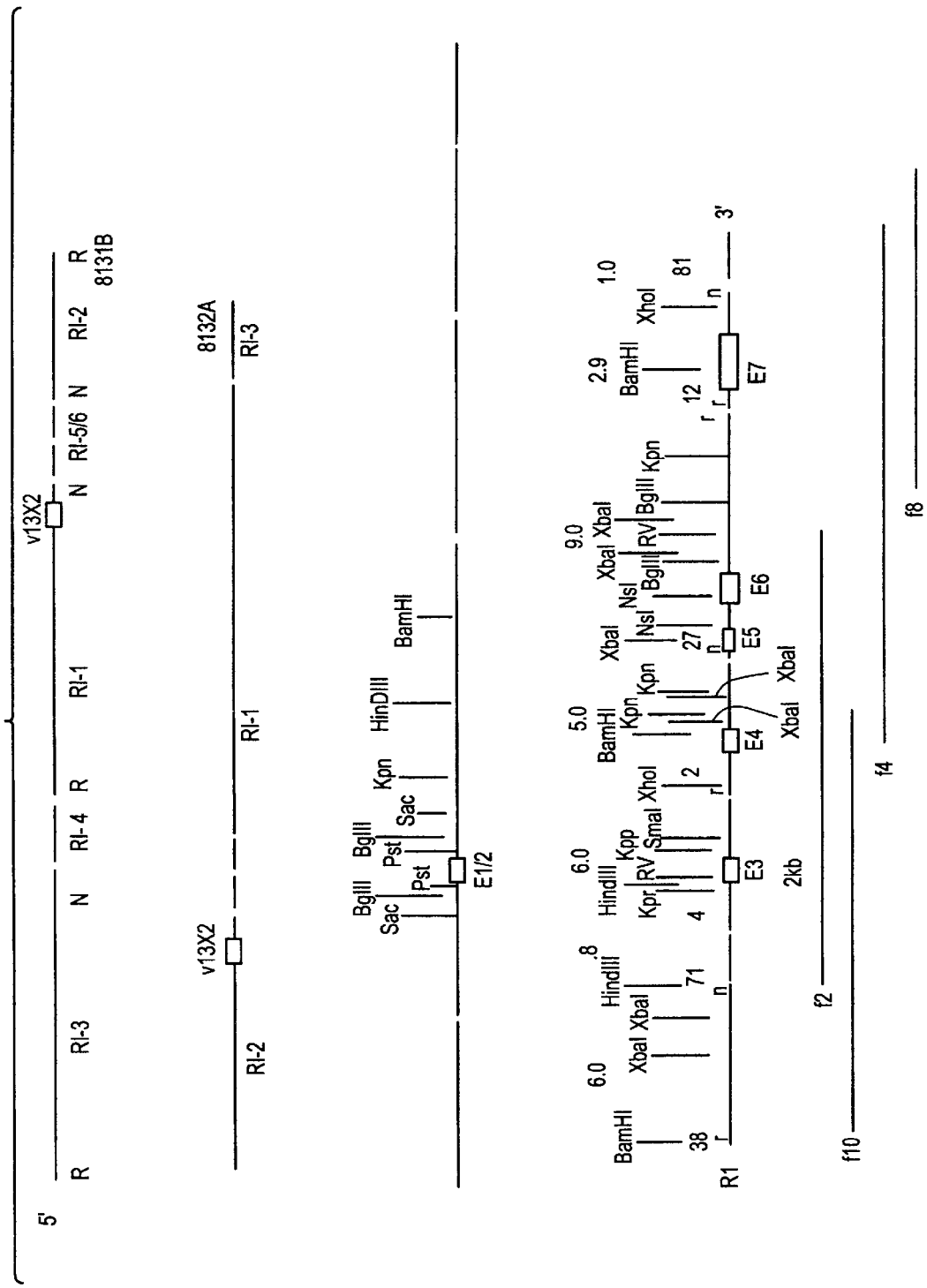

FIG. 7 is a map of the genomic organization of the mouse Ikaros gene. The entire gene is 80–90 kB in length. Intronic or uncharacterized DNA is indicated as a line between 5' and 3'. Exons are indicated as boxes. Lines numbered f2, f10, f4, and f8 indicate phage inserts corresponding to the sequence immediately above. Restriction sites are indicated by the usual abbreviations.

Figure 8:
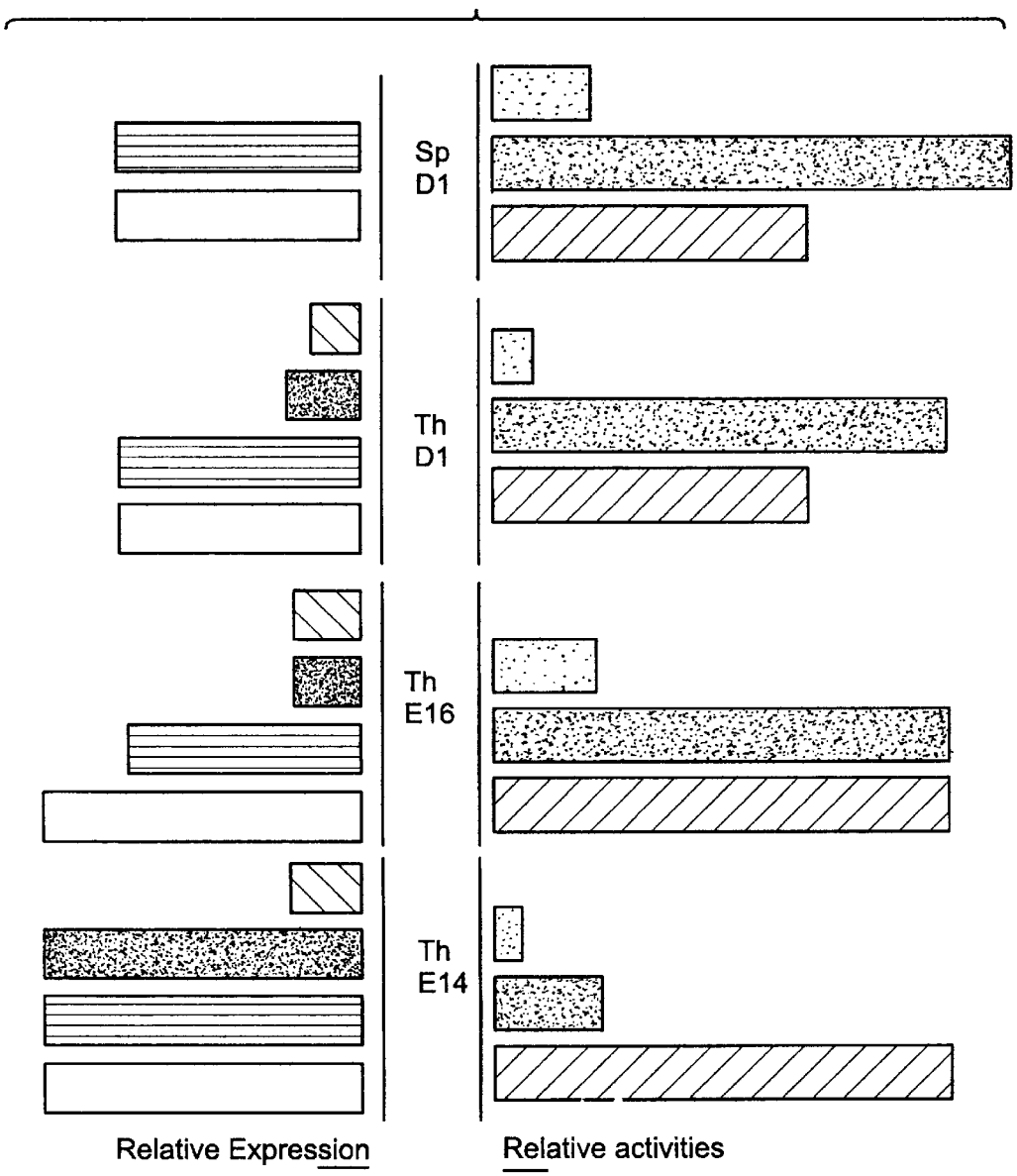

FIG. 8 is a model of Ikaros isoform control of differential gene expressions. Th=thymus; Sp=spleen; Ex=day of embryonic development; Dx =day of postnatal life. The left hand column represents the relative expression of an isoform at a given developmental stage. Open bar=mIk-1; Horizontal stripes=mIk-2; Diagonal stripes=mIk-3; and solid bar=mIk-4. The right hand side shows the resulting reactivity of Ikaros binding sites at a given developmental stage. Light bars=low affinity sites (sites at which isoforms 1, 2, 3 and 4 bind with similar affinities); Dark bars=high affinity inverted or direct repeat containing sites (e.g., NFKB sites, Ik1-4 bind with high affinity); Diagonal bars=single high affinity sites (sites where Ik1 and Ik2 bind but Ik3 and Ik4 don't bind (and therefore won't attenuate the binding of mIk-1 and mIk-2).

FIGS. 9A through 9F is an amino acid sequence alignment of Exon 3–Exon 7 of the mouse Ik-1 isoform (SEQ ID NO:5) and the human Ik-1 isoform (SEQ ID NO:3).

Ikaros: A master regulator of hemopoietic differentiation

A hemopoietic stem cell in the appropriate microenvironment will commit and differentiate into one of many cell lineages. Signal transduction molecules and transcription factors operating at distinct check points in this developmental pathway will specify the cell fate of these early progenitors. Such molecules are viewed as master regulators in development but also serve as markers for the ill defined stages of early hemopoiesis.

Studies on the transcriptional mechanisms that underlie gene expression in T and B cells have identified several transcriptional factors involved in lymphocyte differentiation. However, some of these genes appear to play a role in several developmental systems as determined by their non restricted pattern of expression in the adult and in the developing embryo. The HMG box DNA binding proteins TCF and LEF restricted to T cells and early lymphocytes in the adult are widely expressed in the developing embryo. The T cell specific GATA-3 transcription factor is also expressed outside the hemopoietic system in the early embryo. The ets family members Ets-1 and Elf-1 are widely distributed as well. In addition, the binding affinity and transcription potential of most of these proteins is controlled by other tissue restricted molecules. The ets proteins interact with additional factors for high affinity binding to their cognate sequences. TCFI, LEF and ets-1 must interact with other lymphoid restricted accessory proteins to activate transcription.

In search of a lymphoid restricted transcriptional enhancer, in control of gene expression in early T cells, the Ikaros gene family was isolated, which encode zinc finger DNA binding proteins. In the early embryo, the Ikaros gene is expressed in the hemopoietic liver but from mid to late gestation becomes restricted to the thymus. The only other embryonic site with Ikaros mRNA is a small area in the corpus striatum. In the adult, the Ikaros mRNA is detected only in the thymus and in the spleen (Georgopoulos et al. 1992). The Ikaros gene functions as a transcriptional enhancer when ectopically expressed in non lymphoid cells.

The Ikaros gene plays an important role in early lymphocyte and T cell differentiation. The Ikaros gene is abundantly expressed at early embryonic hemopoietic sites is later on restricted in the developing thymus. The thymus together with the spleen are the prime sites of expression in the adult. This highly enriched expression of the Ikaros gene was also found in early and mature primary T cells and cell lines. This restricted pattern of expression of the Ikaros gene at sites where embryonic and adult T cell progenitors originate together with the ability of the encoded protein to activate transcription from the regulatory domain of an early T cell differentiation antigen supported a determining role in T cell specification.

Differential splicing at the Ikaros genomic locus generates at least five transcripts (Ik-1, Ik-2, Ik-3, Ik-4 and Ik-5) that encode proteins with distinct DNA binding domains. A high level of conservation was found between the human and mouse homologs of the Ikaros gene. The human and mouse Ikaros proteins exhibit nearly 100% identity at their N-terminal zinc finger domain (F1) which was shown to determine the DNA binding specificity of these proteins. In the mouse, differential splicing allows for the distinct combinations of zinc finger modules present in the Ik-1, Ik-2 Ik-3 and Ik-4 isoforms. This differential usage of zinc finger modules in the mouse isoforms establishes the basis of their distinct DNA binding properties and abilities to activate transcription. Differential splicing of the exons encoding the zinc finger DNA binding modules is also manifested in the human Ikaros gene and generates at least two isoforms homologues of the mouse Ik-1 and Ik-4.

These Ikaros protein isoforms (IK-1, IK-2, IK-3, IK-4, IK-5) have overlapping but also distinct DNA binding specificity dictated by the differential usage of zinc finger modules at their N-terminus. In the mouse isoforms (hereinafter designated "mIk), and presumably in the human isoforms (hereinafter designated "hIk"), the core binding site for four of the Ikaros proteins is the GGGA motif but outside this sequence their specificity differs dramatically. The mIK-3 protein shows strong preferences for bases at both the 5' and 3' flanking sequences which restricts the number of sites it can bind to. The mIk-1 protein also exhibits strong preference for some of these flanking bases and can bind to wider range of sequences. The mIk-2 protein, the most promiscuous of the three proteins, can bind to sites with just the GGGAa/t motif. Finally, the mIk-4 protein with similar sequences specificity to mIk-1 binds with high affinity only when a second site is in close proximity suggesting cooperative site occupancy by this protein. Given the identity between the human and mouse Ik-1 and Ik-4 DNA binding domains, the human isoforms are expected to bind similar sequences to their mouse homologues and regulate transcription in a similar fashion. This extreme species conservation between these two functionally diverse Ikaros isoforms support an important role for these proteins in lymphocyte transcription. The C-terminal domain shared by all of the mouse and human Ikaros isoforms is also highly conserved. This portion of the Ikaros proteins contains conserved acidic motifs implicated as transcription activation domains.

A number of binding sites for the Ikaros proteins were identified by sequence homology, in the enhancers of the T cell receptor -δ, -β and -α and the CD3- δ,-ε and -γ genes, in the HIV-LTR, the IL2-Rα promoter and a variety of other lymphocyte restricted genes. Single and composite binding sites for the Ikaros proteins were found in the TCR-α, -β and -δ enhancers, and occupancy of these sites by the Ikaros proteins may underlie their temporal activation during T cell development. A number of well described NF-κB binding sites present in the promoter and enhancers of genes whose expression is modulated during lymphocyte differentiation and activation also represent composite high affinity binding sites for the Ik-1, Ik-2 and Ik-4 isoforms. In some cell types, such as in the terminally differentiated immunoglobulin secreting plasma cell, where Ikaros isoforms are expressed at minimal amounts, members of the NF-κB/rel family probably play a primary role in the activity of these NF-κB sites. However, in early B lymphocytes and in the activated T cell, functionally diverse Ikaros isoforms present in abundance may be involved in the transcriptional control of some of these NF-κB sites. Within the nucleus of a differentiating T or an early B cell, the Ikaros isoforms may compete for binding with the non-activating members of the NF-κB complex (e.g., p50$_2$, Bours et al. (1993) *Cell* 72:729–739; and Franzoso et al. (1993) *EMBO J* 12:3893–3901) as well as with the NF-κB complex in the activated T cell. Understanding the interaction between Ikaros proteins and other factors and their subcellular localization in the resting and activated T cell may help us determine their role in the activity of NF-κB sites. Thus, gene regulation of at least the IL2α Receptor during T cell differentiation and activation may be controlled by the intricate interplay of NFkB and Ikaros transcription factors interacting on common grounds.

The embryonic expression pattern and activation potential of the Ikaros isoforms are also markedly distinct. The stronger transcriptional activators, Ik-1 and Ik-2, are found in abundance in the early fetal liver, in the maturing thymus and in a small area in the developing brain, whereas the weak activators, e.g. Ik-3 and Ik-4, are present at significantly lower levels in these tissues during these times. Consequently, Ik-1 and Ik-2 are expected to play a primary role in transcription from sites that can bind all four of the Ikaros proteins. However, in the early embryonic thymus and in the late mid-gestation hemopoietic liver the weak activator Ik-4 is expressed at similar mRNA levels to the Ik-1 and Ik-2 isoforms. The Ik4 weak activator can bind only to composite sites while Ik-1 and Ik-2 can bind to a range of single and composite sites. The Ik-1 and Ik-2 proteins recruited to composite sites (a fraction of the total protein), during early to mid gestation, will have to compete for binding with the Ik-4 isoform, solely recruited to these sites. Consequently the activity of these composite sites may be primarily controlled by the Ik-4 isoform, a weak transcription activator. Modulation of Ik-4 expression in the developing thymocyte, in combination with steady levels of the Ik-1 and Ik-2 expression may determine the temporal and stage specific expression of T cell differentiation antigens. Low affinity binding sites for these proteins may also become transcriptionally active in the late stages of T cell development when the most potent activators, Ik-1 and Ik-2, accumulate. In the fly embryo the NF-κB/rel homologue Dorsal, a maternal morphogen, engages in interactions with transcriptional factors binding to adjacent sites. These protein-protein interactions determine the activation level and threshold response from low and high affinity binding sites (Jiang et al. (1993) *Cell* 72:741–752). The transcriptional activity of the Ikaros proteins may be further regulated by such mechanisms in the developing lymphocyte. In addition, the activity of the Ikaros proteins may be under postranslational control operating during both lymphocyte differentiation and activation. FIG. 8 provides a model in which the relative concentrations of Ikaros isoforms at different developmental stages confer different reactivites on the various sites.

The transcriptional activity of the mIk-3 and mIk-4 proteins may be further regulated by T cell restricted signals mediating postranslational modifications or by protein-protein interactions. The mIk-4 protein binds NFkB motif in a cooperative fashion and may therefore interact in situ with other members of the Ikaros or of the NFkB family. These protein-protein-DNA complexes may dictate a differential transcriptional outcome.

The differential expression of the Ikaros isoforms during T cell ontogeny, their overlapping but also unique binding specificities and their diverse transcriptional potential may be responsible for the orderly activation of stage specific T cell differentiation markers. Multiple layers of gene expression in developing lymphocytes may be under the control of these Ikaros proteins. Synergistic interactions and/or competition between members of the Ikaros family and other transcription factors in these cells on qualitatively similar and distinct target sites could dictate the complex and ever changing gene expression in the differentiating and activated lymphocyte. This functional dissection of the Ikaros gene strongly suggest it functions as a master gene in lymphocytes, and an important genetic switch for early hemopoiesis and both B and T cell development.

The Ikaros gene maps to the proximal arm of human chromosome 7 between p11.2 and p13 next to Erbb In the mouse the Ikaros gene maps to the proximal arm of chromosome 11 tightly linked to Erbb. Other genes linked to the Ikaros locus in the mouse are the Leukemia inhibitory factor (Lif) and the oncogene Rel a member of the NFK-B family. All three of the genes linked to the Ikaros gene in the mouse appear to play an important role in the development of the hemopoietic system. The tight linkage between the Erbb and the Ikaros genes on syntenic loci in the mouse and human may be related to their genetic structure and regulation. Nevertheless, no known mutations were mapped to the Ikaros locus in the mouse However, this does not preclude the importance of the Ikaros gene for the lymphopoietic system Naturally occurring mutations that affect development of the immune system may not be readily obtained in mice since such mutant animals may only thrive under special care conditions.

That the Ikaros gene is a fundamentally important regulator of lymphocyte development is substantiated by analysis of its human homologue. The overall conservation of the Ikaros proteins between mice and men at the genetic level and protein level but also their restricted pattern of expression in the developing lymphocyte, e.g. in maturing T cells, e.g. in maturing B cell, strongly support their participation in the same regulatory pathway across species.

Mutational Analysis of the δ Element of the CD3δ Enhancer

One approach useful for characterizing early events in T cell differentiation is to study the regulation of transcription of T cell restricted antigens. The transcriptional control of one of the earliest and definitive T cell differentiation markers, the CD3δ gene of the CD3/TCR complex was chosen for study. In order to identify a transcription factor expressed at or earlier than T cell commitment which can function as a genetic switch regulating entry into the T cell lineage, a T cell specific enhancer mediating expression of this gene was characterized. This enhancer is comprised of two functionally distinct elements δA and δB with activity restricted in T cells. Mutational analysis of the δA element has further identified two transcriptionally active binding sites, a CRE (Cyclic AMP response)-like element and a G rich sequence motif both of which are required for full activity of the δA element and the CD3 enhancer, see FIG. 1.

Figure 1A:
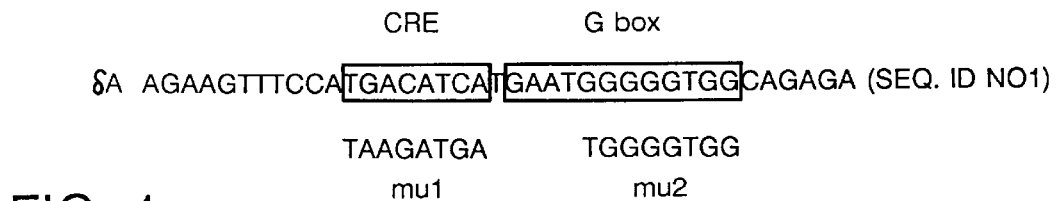
FIG. 1A is a map of the δA element of the CD3 enhancer (SEQ ID NO:1).

FIG. 1 depicts the functional dissection of the δA element of the CD3δ enhancer. FIG. 1A shows the binding sites in the δ element (SEQ ID NO:1). The boxed sequences represent the CRE-like and the G rich motif both important for activity of the δA element. Mutations introduced in the δA element are shown below the sequence.

Figure 1B:
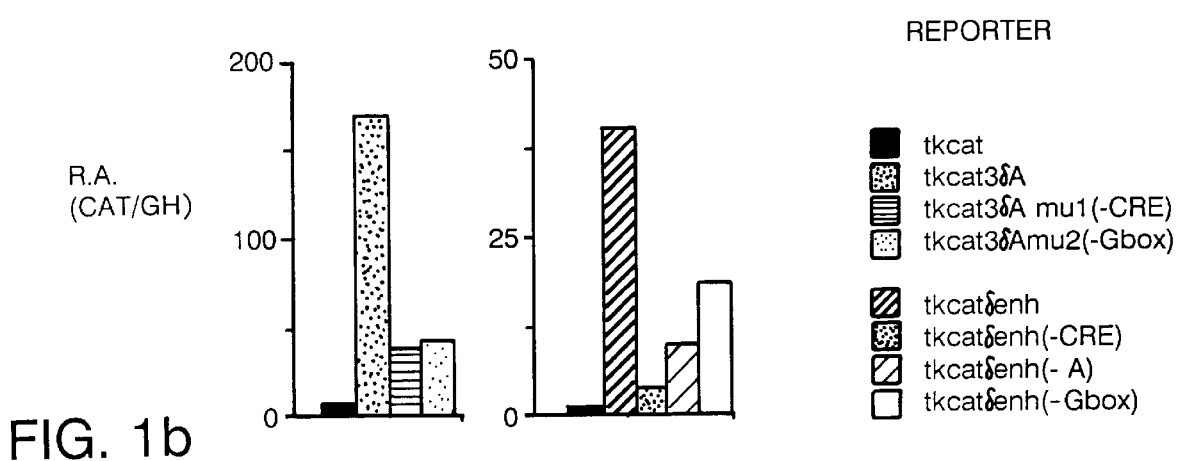
FIG. 1B is a graph of the contribution of the CRE and the G box to the activity of the element as analyzed by expression of tkCAT reporter gene under the control of various element sequences.
Figure 1C:
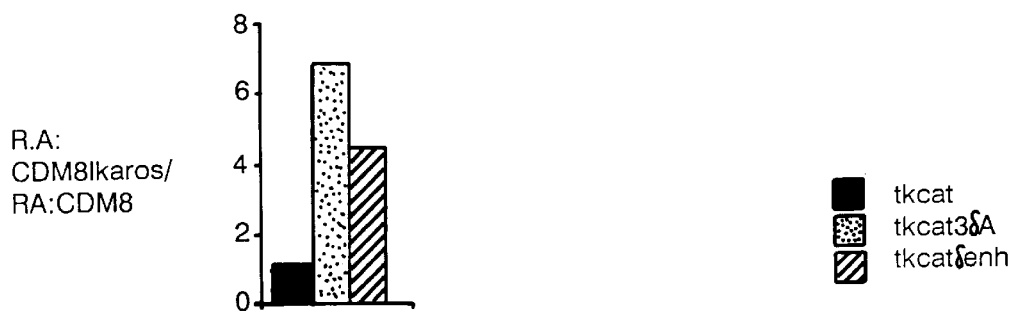
FIG. 1C is a graph of the effect of Ikaros expression on the activity of the δ element in non-T cells.

FIG. 1B shows the contribution of the CRE and the G box to the activity of the δA element and the CD3δ enhancer as analyzed by transient expression assays in the T cell line EL4. The activity of the tkCAT reporter gene under the control of wild type δA, δAmu1 and δAmu2 as reiterated elements or in the context of the CD3δ enhancer was determined as described in Georgopoulos et al. (1992) *Mol Cell Biol* 12:747. Reporter gene activation (R.A.) was expressed as the ratio of Chloramphenicol Acetyl Transferase (CAT) to Growth Hormone (GH) activity estimated for each transfection assay. FIG. 1C shows that the expression of the Ikaros gene (mIk-2)in non T cells upregulates the activity of the δA element. The CDM8 and CDM8:Ikaros recombinant I express ion vectors were cotransfected with the tkcat 3δA, tkcat 3δAmuI, tkcat 3δAmu2 and tkcat δenhancer reporter genes in CV1 (kidney epithelial) cells as described in Georgopoulos et al. (1992). The ratio of reporter activation (R.A.=CAT/GH) in the presence and absence of Ikaros expression was estimated. Three isoforms of the ubiquitously expressed CRE-Binding Protein were cloned from T cells for their ability to interact with the CRE-like binding site of the δA element, see Georgopoulos et al. (I1992). Although dominant negative mutants of this protein down regulate the activity of this enhancer element in T cells, expression of this transcription factor in all hemopoietic and non hemopoietic cells argues against it being the switch that activates the CD3δ enhancer in the early prothymocyte progenitor. A variant of the δA element (δAmuI-CRE) was used to screen a T cell expression library as described in Georgopoulos et al. (1992). As described below, a T cell restricted cDNA was cloned encoding for a novel zinc finger protein (Ikaros) that binds to the G box of the A element.

Cloning the mouse Ikaros Gene

A T cell expression cDNA library from the mature T cell line E14 was constructed into the A ZAP phage vector.

A multimerized oligonucleotide encoding sequence (SEQ ID NO:154) from one of the protein binding sites of the CD38 enhancer was used as a radiolabelled probe to screen this expression library for the T cell specific proteins that bind and mediate enhancer function by the southwestern protocol of Singh and McKnight. Four gene encoding DNA binding proteins were isolated. One, the Ikaros gene, encoded a T cell specific protein.

The Sequence of mouse Ikaros

The sequence of the Ikaros gene was determined using the Sanger dideoxyl sequencing protocol. The derived amino acid sequence was determined using the MAP program of GCG (available from the University of Wisconsin) and Strider sequence analysis programs. FIG. 2 provides the sequence of a mouse Ikaros cDNA (mIk-2) and the derived amino acid sequence encoded thereby (SEQ ID NO:2). Sequence information for other isoforms of mouse Ikaros proteins (and cDNAs) are provided in SEQ ID NO:4 (mIk-3), SEQ ID NO:5 (mIk-1), SEQ ID NO:6 (mIk-4), and SEQ ID NO:7 (mIk-5).

A mouse Ikaros Protein

The Ikaros protein shown in FIG. 2 (mIk-2) is comprised of 431 amino acids with five $CX_2CX_{12}HX_3H$ zinc finger motifs organized in two separate clusters. (See also FIG. 5.) The first cluster of three fingers is located 59 amino acids from the initiating methionine, while the second cluster is found at the C terminus of the protein 245 amino acids downstream from the first. Two of the finger modules of this protein deviate from the consensus amino acid composition of the Cys-His family of zinc fingers; finger 3 in the first cluster and finger 5 at the C terminus have four amino acids between the histidine residues. This arrangement of zinc fingers in two widely separated regions is reminiscent of that of the Drosophila segmentation gap gene Hunchback. Similarity searches in the protein data base revealed a 43% identity between the second finger cluster of Ikaros and Hunchback at the C terminus of these molecules. This similarity at the C terminus of these proteins and the similar arrangement of their finger domains raises the possibility that these proteins are evolutionary related and belong to a subfamily of zinc finger proteins conserved across species.

Ikaros isoforms

Figure 4:
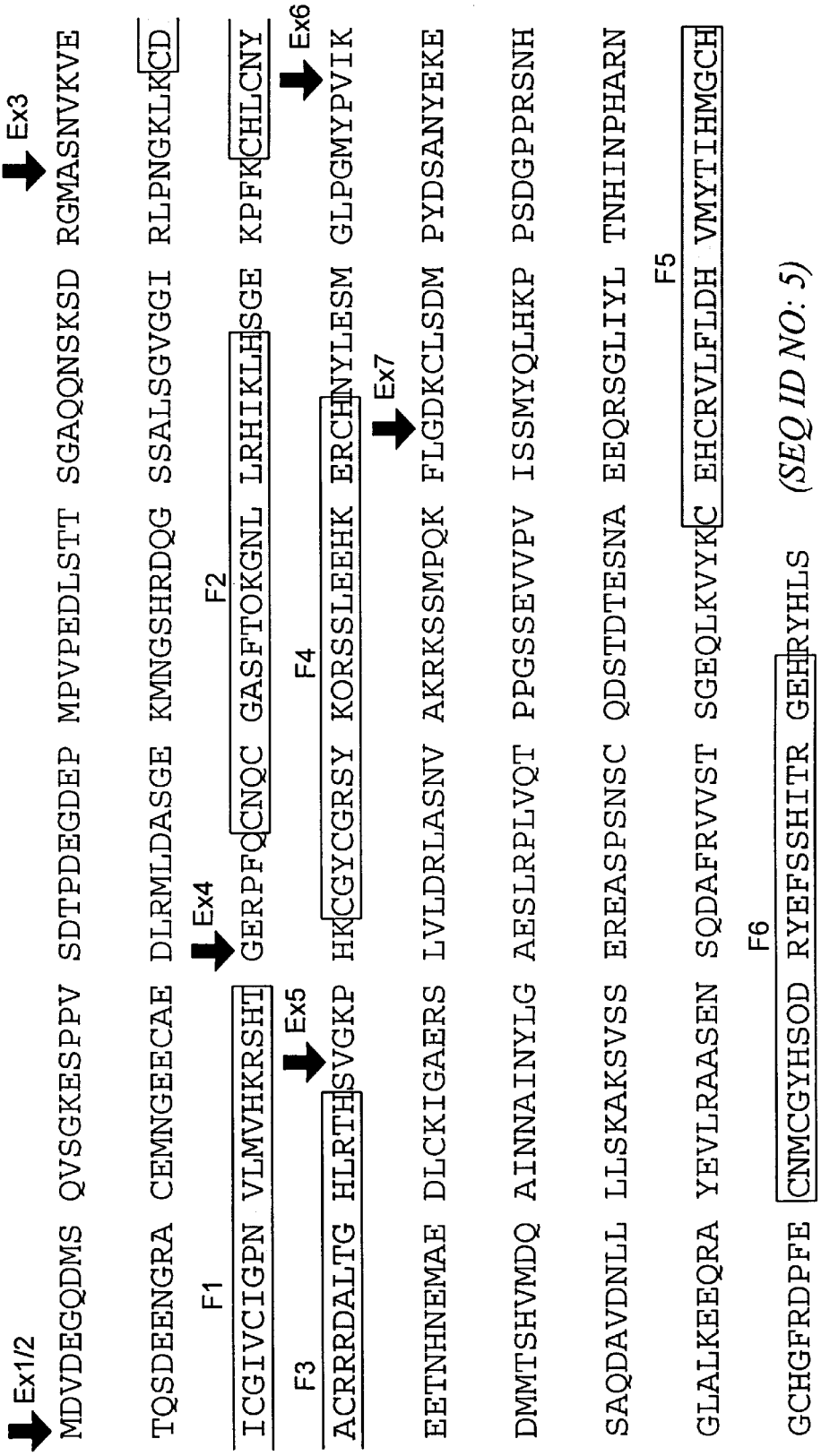
FIG. 4 is a depiction of the partial amino acid composition of the IK-1 cDNA, including Ex3, Ex4, Ex5, Ex6, and Ex7 (SEQ ID NO:5).

In addition to the cDNA corresponding to mIk-2, four other cDNAs produced by differential splicing at the Ikaros genomic locus were cloned. These isoform encoding cDNAs were identified using a 300 bp fragment from the 3' of the previously characterized Ikaros cDNA (mIk-2, FIG. 1). As shown in FIG. 4 and 5, each isoform is derived from three or more of six exons, referred to as E1/2, E3, E4, E5, E6 and E7. All five cDNAs share exons E1/2 and E7 encoding respectively for the N-53 and C-terminal 236 amino acid domains. These five cDNAs consist of different combinations of exons E3–6 encoding the N-terminal zinc finger domain. The mIk-1 cDNA (SEQ ID NO: 5) encodes a 57.5 kD protein with four zinc fingers at its N-terminus and two at its C-terminus and has the strongest similarity to the Drosophila segmentation protein Hunchback (Zinc fingers are indicated as F1, F2+F3, F4, and F5+F6 in FIG. 5). The mIk-2 (SEQ ID NO:2) and mIk-3 (SEQ ID NO: 4) cDNAs encode 48 kd proteins with overlapping but different combinations of zinc fingers. The mIk-3 isoform contains fingers 1, 2, 3 while mIk-2 contains fingers 2, 3 and 4. The 43.5 kD mIk-4 protein (SEQ ID NO: 6) has two fingers at its N-terminus also present in mIk-1 and mIk-2. The mIk-5 cDNA (SEQ ID NO: 7) encodes a 42 kd protein with only one N-terminal finger shared by mIk-1and mIk-3 (FIG. 1). This differential usage of the zinc finger modules by the Ikaros proteins support an overlapping but differential DNA binding specificity.

cDNA cloning of isoforms was performed as follows. A cDNA library made from the T cell line EL4 in λZAP was screened at high stringency with a 300 bp fragment from the 3' of the previously described Ikaros cDNA (isoform2). Positive clones were characterized by sequencing using an antisense primer from the 5' of exon 7.

Mouse Ikaros Expression

Tissue Specific Expression of the Ikaros Gene

The Ikaros gene is expressed in T cells and their progeny. In the adult mouse, Ikaros mRNA is restricted to the thymus and the spleen with expression in the thymus being about 3 fold higher than the spleen. Spleen cells preparations depleted of T cells expressed very low levels of this message. Examination of Ikaros expression in cell lines confirm the view that the Ikaros gene is expressed in T cells and their progeny. Ikaros mRNA was detected in a number of T lymphoma cell lines. The T cell line EL4 expressed the highest levels while DO11.10, BW5147 and SL12.1 lymphomas showed moderate to low expression. No expression or very low levels were detected in cell lines representing other hemopoietic lineages including the bone marrow derived progenitor cells FDCPI that exhibit myeloid morphology and differentiation potential, the mast cell line RBL, the macrophage line J774 (detected expression is 25 fold lower than that in thymocytes) and MEL cells which were induced to differentiate into erythroid cells. Nevertheless, moderate levels of Ikaros mRNA were detected in the B cell lymphoma A20 and in the proerythroleukemia cell line MEL. Immortalization of these cell lines and their leukemic phenotype may account for aberrant expression of this nuclear factor which does not appear to be expressed at significant levels in normal B cells (spleen T cell depleted population, or in erythroid progenitors in vivo (from in situ data). Alternatively expression of this thymocyte restricted factor in these cell lines may reflect the existence of an early progenitor with the ability to differentiate into the lymphoid or the erythroid lineage.

Tissue distribution of the Ikaros gene was determined by Northern hybridization of total RNAs prepared from: the T lymphoma cell lines EL4, BW5147, DO11.10, SL12.1; the B cell lymphoma A 20; the tissues of thymus, spleen, kidney, brain and heart isolated from an adult mouse; spleen thymocytes (total and polyA-RNA); bone marrow derived stem cell progenitors FDCPI; macrophage cell line J774; mast cell line RBL; undifferentiated MEL and 58 hr DMSO induced MEL cells; and finally T depleted spleen cells (TDSC). A 320 bp fragment (bp 1230–1550) from the 3' end of the Ikaros mIk-2 cDNA was used as a probe.

Temporal Regulation of the Expression of the Ikaros Gene

To determine when in hemopoiesis the Ikaros gene becomes activated its expression was studied in situ in the developing mouse embryo. Hemopoiesis begins at day seven in the yolk sac of the mouse embryo with the generation of a large population of primitive erythroblasts. The Ikaros mRNA is not detected in the yolk sac at day 8 in contrast to the erythroid specific transcription factor GATA-1 which is expressed at this time in development. In the embryo proper, expression of Ikaros is first detected in the early liver rudiment at the onset of its hemopoietic function (day- 9½–10½). At this time, pluripotent stem cells as well as more restricted progenitors are found in the liver which can successfully reconstitute irradiated animals with the whole spectrum of hemopoietic lineages. Expression of the Ikaros gene remains strong in the liver up to day fourteen and begins to decline thereafter although the liver is the major site of hemopoiesis through mid gestation and remains active through birth. The declining expression of the Ikaros gene in the fetal liver at mid gestation is consistent with changes in the hemopoietic profiles from pluripotent stem cells to more committed erythroid progenitors.

The second site of Ikaros expression is in the thymic rudiment around day 12 when lymphopoietic stem cells are first colonizing this organ. A group of expressing cells is detected at the center of the thymic rudiment surrounded by non expressing cells in the periphery. Expression in the developing thymus becomes quite prominent by day 16 and persists throughout embryogenesis to the adult organism. At these developmental stages expression of Ikaros mRNA is detected throughout the thymus with levels in the medulla sections being slightly more elevated than these in the cortex.

Ikaros expression is first detected in the spleen during late gestation at low levels compared to those of the thymus (day 19). Although the spleen is active in erythropoiesis and myelopoiesis from mid-gestation, its population with mature T cells from the thymus takes place late in embryogenesis and correlates with the late expression of the Ikaros gene. No expression of Ikaros message is detected in the bone marrow of the long bones or the spinal column at day 19 in contrast to the myeloid specific factor Spyl and to the erythroid factor GATA-1. The pattern of expression of the Ikaros gene detected in distinct hemopoietic sites throughout embryonic development is consistent with its restriction to T cells and their progenitors. The only other site in the mouse embryo that exhibited Ikaros expression was a restricted area in the brain which gives rise to the proximal corpus striatum (day 12 through 19).

Embryos were harvested from time pregnant CD 1 mice (Charles River) and were fixed in 4% paraformaldehyde for 2 hours to 2 days depending on size. A series of dehydration steps was performed in alcohols followed by xylenes before paraplast embedding. Sections were prepared and treated according to published protocols. Sense and antisense P-UTP RNA probes 300 bp in size were made from the 3' untranslated region of the Ikaros cDNA and were used to hybridize to selected slides at 48° C. overnight. After high stringency washings slides were dehydrated and dipped in diluted photographic emulsion (NBT2) for 3 weeks. Dipped slides were developed, stained with Giemsa and analyzed by bright and dark field microscopy.

Expression of Ikaros Isoforms

The pattern of Ikaros isoforms expression in the developing embryo was studied. Two sets of primers were used to amplify the five cDNAs as distinct sized bands from embryonic and postnatal tissues (FIG. 6). A third set of primers complementary to the β-actin cDNA was used to normalize the amount of cDNA used n the reaction. Primers 1/2 amplified a 720, a 457 and a 335 bp fragment from the mIk-1, mIk-2 and mIk-4 cDNAs. Primers 3/4 amplified a 715, a 458 and a 293 bp fragment from the mIk-l, mIk-3 and mIk-5 cDNAs. A 650bp band detected is an artifact of mIk-1 and mIk-2 coamplification representing mIk-1/mIk-2 and mIk-1/mIk-3 hybrid molecules. It is present at significant levels at the later amplification cycles when the primers to mIk-1, mIk-2 and mIk-3 ratio is decreased. This band is also detected when we coamplify mIk-1, mIk-2 and mIk-3 DNA templates. The identity of the above described bands were also confirmed by cloning and sequencing. It is noteworthy that the 650 bp species was never cloned as a novel of cDNA.

During embryonic development all five Ikaros mRNAs were expressed in hemopoietic centers and in the brain at relatively different levels. The mIk-1 and mIk-2 mRNA were abundantly expressed in the early fetal liver, the maturing thymus, and the postnatal spleen. The mIk-4 isoform was expressed at low levels compared to mIk-1 and mIk-2 in the early fetal liver and in the maturing thymus (liver E14, thymus E16 and D1). However it was expressed at comparable amounts to mIk-1 and mIk-2 in the early thymus and mid-gestation liver (Table 1, thymus E14, liver E16). This equalization was due to a decrease in the expression of the latter two mRNAs rather than an increase in the expression of the mIk-4 transcript. In the embryonic day 14 thymus, the mIk-4 isoform was expressed at similar if not higher levels than the mIk-1 and mIk-2 mRNAs, but its expression declined during mid-gestation. The pattern of expression of mIk-1, mIk-2, and mIk-4 mRNAs detected in the day 16 embryonic thymus persisted past birth in this organ, in contrast to liver expression which was switched off in the neonate. mIk-1 and mIk-2, but not mIk-4, mRNAs were readily detectable in the spleen of the neonate. The mIk-3 and mIk-5 isoforms were expressed but at significantly lower levels than mIk-1 and mIk-2 throughout development (Table 1). Finally, the mIk-5 transcript present at very low amounts in the developing lymphocyte was readily seen after a higher number of amplification cycles.

All five isoforms were expressed in the embryonic brain. The mIk-1 was the most abundant mRNA, mIk-2 and mIk-4 were present at similar but lower levels, while mIk-3 and mIk-5 were the least expressed. The expression of Ikaros isoforms in the brain was decreased from mid gestation to day 1, and likely reflects it restriction to a discrete cellular compartment in this organ.

The expression pattern of the Ikaros isoforms detected in the late embryonic thymus persisted past birth while the declining liver expression was switched off. The neonatal spleen expressed only mIk-1 and mIk-2 mRNAs at significant amounts. Low concentration of mIk-1 were still detected in the neonatal brain. These data agree and further supplement our previous in situ hybridization studies performed using an RNA probe made from the 3' of the Ikaros gene shared by all identified Ikaros splicing products.

TABLE 1

A summary of the embryonic expression patterns for the mIk-1–5 transcripts.

|  |  | mIk-1 | mIk-2 | mIk-3 | mIk-4 | mIk-5 |
|---|---|---|---|---|---|---|
| Liver | E14 | +++++ | ++++ | ++ | ++/− | − |
|  | E16 | +++ | ++ | +/− | ++/− | − |
|  | D1 | + | − | − | − | − |
| Thymus | E14 | +++ | +++ | +/− | +++ | − |
|  | E16 | ++++ | +++ | +/− | + | +/− |
|  | D1 | +++ | +++ | − | + | + |
| Brain | E14 | ++ | + | +/− | + | + |
|  | E16 | ++ | + | +/− | + | + |
|  | D1 | + | − | − | − | − |
| Spleen | D1 | +++ | +++ | − | − | − |

Embryonic tissues were obtained from embryos harvested from of time pregnant mothers (E14, E16, D1, obtained from TACONIC) and total RNA was prepared. 2–5 μgs of total RNA prepared from the thymus, liver, brain and spleen at different stages of embryonic development were used for cDNA synthesis with random hexamers and Superscript RNaseH. 1/10th of cDNA made was used in PCR amplification with the 1/20, 3/4 and actin A/B set of primers. PCR reactions were denatured at 95° C. for 5 minutes, polymerase was added at 80° C., and then were amplified for 25 cycles at 94° C. for 45", 63° C. for 1' and 72° C. for 1'. PCR amplification for the actin cDNAs were performed for 30 cycles. Products were separated on 2% Seakam FMC agarose, bands were excised, cloned (TA cloning kit, Clonteck) and sequenced to verify their identity.

Ikaros stimulates the transcription from the δA element

Initial Transcriptional Studies

The ability of an Ikaros protein that can bind to the δA element to also activate transcription from this binding site was examined. The tkCAT reporter gene under the control of either a reiterated δA binding site (±CRE/-G) or under the control of the CD3δ enhancer was cotransfected with a recombinant vector expressing the Ikaros gene in the kidney epithelial cell line CV1. Expression of the Ikaros gene in non T cells strongly stimulated transcription from the G box of a reiterated δA element and in the context of the CD3δ enhancer (see FIG. 1C). Activity of the δA and δAmu1(-CRE) elements was stimulated by eight and seven fold respectively while expression of the CD3δ enhancer was stimulated by five fold. Since the CD3δ enhancer is comprised of at least two regulatory elements, expression of all the transcription factors that bind to these sites is necessary for its full activation potential. Expression of the Ikaros gene did not significantly stimulate the activity of the thymidine kinase promoter or of the δAmu2(-Gbox) element (see FIG. 1C). These data confirms our hypothesis that the Ikaros gene can control activity of the T cell specific δA element of the CD3δ enhancer and suggests that it can mediate expression of at least the CD3δ gene in T cells.

The expression pattern of the Ikaros protein, and its ability to modulate the activity of the CD3δ enhancer, is consistent with a role in mediating gene expression in T cells in the embryo and in the adult. Its early expression in fetal liver hemopoietic stem cells suggests that it may be expressed in early prothymocyte progenitors and raiser the possibility that it is responsible for commitment of a pluripotent stem cell to the T cell lineage.

Binding Site Selections for the Ikaros 1–3 Isoforms

To investigate the possibility that differential usage of zinc finger modules by the five Ikaros isoforms contributes to their DNA binding a specificity, we cloned high affinity binding sites for three of these proteins. The mIk-1, mIk-2 and mIk-3 proteins were selected since they contain either all four (mIk-1) or two distinct combination of three (mIk-2 and mIk-3) from the pool of the N-terminal four fingers (FIG. 5). We expected these proteins to overlap in specificity with mIk-4 and mIk-5 proteins which contain only two or one of these putative DNA binding modules. In addition, GST fusion proteins derived from the mIk-1, mIk-2 and mIk-3 isoforms lacking the C-terminal portion encoded by exon-7 (e.g. lacking the zinc fingers F5 and F6) were constructed, as well as truncated mIk-1 (containing F1, F2, F3 and F4), mIk-2 (containing F2, F3 and F4) and mIk-3 (containing F1, F2 and F3).

After five rounds of binding site selections from a pool of random oligonucleotides the mIk-1-, mIk-2- and mIk-3 selected oligomers were cloned, sequenced and aligned to a shared motif (Tables 2, 3 and 4 in the tables, bold face type indicates conserved sequence).

TABLE 2

| Ik1-1 | aggcgaTTTTGGGAATTTCacacc | (SEQ ID NO:9) |
|---|---|---|
| Ik1-2 | aggcCATGGGAATGAAGGAacacc | (SEQ ID NO:10) |
| Ik1-3 | ggtgtAAATTGGGAATGCTGtgcct | (SEQ ID NO:11) |
| Ik1-4 | aggcATGGGAATGTCTGGAacacc | (SEQ ID NO:12) |
| Ik1-5 | aggcATTAAAATGGGAATAacacc | (SEQ ID NO:13) |
| IkI-6 | ggtgtAGGAATGCGGTAATTgcct | (SEQ ID NO:14) |
| Ik1-7 | ggtgtGGGAATAACTGGGATgcct | (SEQ ID NO:15) |
| Ik1-8 | ggtgtGGGAATGTCACTTCAgcct | (SEQ ID NO:16) |
| Ik1-9 | ggtgtGGGAATACTGAGTATGCCTgcct | (SEQ ID NO:17) |
| Ik1-10 | aggcAAATTTGGGAATACTacacc | (SEQ ID NO:18) |
| Ik1-11 | ggtgtGTGGGAACATGGGATgcct | (SEQ ID NO:19) |
| Ik1-12 | aggcCTATTTCCCTTGGGAacacc | (SEQ ID NO:20) |
| Ik1-13 | ggtgtGGAACATCGTGGGAAGCCgcct | (SEQ ID NO:21) |
| Ik1-14 | aggcGCTTGGGAAATTCCAacacc | (SEQ ID NO:22) |
| Ik1-15 | aggcATTCCTAAACCGGGAacacc | (SEQ ID NO:23) |
| Ik1-16 | aggcACAATTCCTTCGGGAacacc | (SEQ ID NO:24) |
| Ik1-17 | ggtgtCGGGCTTCGGGAATAgcct | (SEQ ID NO:25) |
| Ik1-18 | gtgtTCCAAACTCGGGAATgcct | (SEQ ID NO:26) |
| Ik1-19 | ggtgtGGAATCGGGAATTTAgcct | (SEQ ID NO:27) |
| Ik1-20 | aggcTTATCGGGAAAACTTacacc | (SEQ ID NO:28) |
| Ik1-21 | gtgtTCCAAACGGGGGAATgcct | (SEQ ID NO:29) |
| IkJ-22 | ggtgtGCAATTCCAAGGAATgcct | (SEQ ID NO:30) |
| Ik1-23 | aggcGCCATTCCAAGGATAacacc | (SEQ ID NO:31) |
| Ik1-24 | aggcTAATCTTGGAATTCCacacc | (SEQ ID NO:32) |

|  | A | N | T | T | G | G | G | A | A | T | A/G | C/T | C/T |
|---|---|---|---|---|---|---|---|---|---|---|---|---|---|
|  | −3 | −1 | −2 | 1 | 2 | 3 | 4 | 5 | 6 | 7 | 8 | 9 | 10 |
| G | 7 | 0 | 7 | 1 | 22 | 24 | 24 | 0 | 0 | 2 | 8 | 2 | 3 |
| A | 7 | 6 | 3 | 2 | 2 | 0 | 0 | 24 | 22 | 3 | 11 | 3 | 3 |
| T | 5 | 9 | 11 | 15 | 0 | 0 | 0 | 0 | 2 | 15 | 3 | 6 | 4 |
| C | 5 | 9 | 3 | 6 | 0 | 0 | 0 | 0 | 0 | 4 | 2 | 13 | 14 |

TABLE 3

| IK2-1 | ggtgtACGGTTGGGAATGCGgcct | (SEQ ID NO:36) |
|---|---|---|
| IK2-2 | ggtgtAGGAATGGGAATACAgcct | (SEQ ID NO:37) |
| IK2-3 | ggtgtTGGGATTGGGAATGTgcct | (SEQ ID NO:38) |
| IK2-4 | ggtgtCGGGAATTATTTTAGgcct | (SEQ ID NO:39) |
| IK2-5 | ggtgtAAAAATGGGAACAAAgcct | (SEQ ID NO:40) |
| IK2-6 | ggtgtGGGAAAGATATAGCCgcct | (SEQ ID NO:41) |
| IK2-7 | ggtgtTTAACCAATTGGGAAgcct | (SEQ ID NO:42) |
| IK2-8 | ggtgtTCCGGTATTTGGGAAgcct | (SEQ ID NO:43) |
| IK2-9 | ggtgtGGGATAACTTGGGAAgcct | (SEQ ID NO:44) |
| IK2-10 | aggcGGGAAAACCCATAGGacacc | (SEQ ID NO:45) |
| IK2-11 | ggtAATCCGTCGGGAACAgcctA | (SEQ ID NO:46) |
| IK2-12 | ggcTTTAGATCAGGGAACacacc | (SEQ ID NO:47) |
| IK2-13 | gtATCCTGGTAGGAATCgcct | (SEQ ID NO:48) |
| IK2-14 | aggcTATCCCAGGAATTTGacacc | (SEQ ID NO:49) |
| IK2-15 | aggcAAATTGTTCAGGAACACacacc | (SEQ ID NO:50) |
| IK2-16 | ggtgtCCATAAGGAACAATAgcct | (SEQ ID NO:51) |
| IK2-17 | aggcAGACCCAAGGAAGCCacacc | (SEQ ID NO:52) |
| IK2-18 | aggcTATCCCAGGAATTTGacacc | (SEQ ID NO:53) |
| IK2-19 | aggAGAATCCTATGGGATacacc | (SEQ ID NO:54) |

TABLE 3-continued

| | | |
|---|---|---|
| IK2-20 | ggtgtTCATTGGGATAGCATgcct | (SEQ ID NO:55) |
| IK2-21 | ggtgtTGGGATTTCTGGATAgcct | (SEQ ID NO:56) |
| IK2-22 | aggcGTTTGGGATGTATTTacacc | (SEQ ID NO:57) |
| IK2-23 | ggtgtGGGATCGCCATATTC | (SEQ ID NO:58) |
| IK2-24 | ggtgtGGGATTGCTTTATTT | (SEQ ID NO:59) |
| IK2-25 | ggtgtGGGATTGGGACTAAAgccta | (SEQ ID NO:60) |
| IK2-26 | ggtgtGGGATTGGGACTAAAgcct | (SEQ ID NO:61) |
| IK2-27 | ggtgtAAGGACAATGGGATAgcct | (SEQ ID NO:62) |
| IK2-28 | ggtgtCAGGATTTGGGACACgcct | (SEQ ID NO:63) |
| IK2-29 | ggtgtGGGACTCAAAGAGGC | (SEQ ID NO:64) |
| IK2-30 | ggtgtCCTCCAGCGGGATAAgcct | (SEQ ID NO:65) |
| IK2-31 | aggcATCCGGGATAATAAAacacc | (SEQ ID NO:66) |
| IK2-32 | ggtgtTCTTCGGGATGGCTTgcct | (SEQ ID NO:67) |
| IK2-33 | aggcTTCACCGGGAGCACGacacc | (SEQ ID NO:68) |
| IK2-34 | ggtgtAGATCCCAGGGATTTgcct | (SEQ ID NO:69) |
| IK2-35 | ggtgtAGGTAGGGACATCCCgcct | (SEQ ID NO:70) |
| IK2-36 | ggtgtGAGAAATAAGGGATAgcct | (SEQ ID NO:71) |

| | N | N | T | T | G | G | G | A | A/T | N | N | C |
|---|---|---|---|---|---|---|---|---|---|---|---|---|
| | -3 | -2 | -1 | 1 | 2 | 3 | 4 | 5 | 6 | 7 | 8 | 9 |
| G | 12 | 7 | 7 | 0 | 30 | 36 | 36 | 0 | 1 | 6 | 9 | 5 |
| A | 9 | 11 | 5 | 6 | 6 | 0 | 0 | 36 | 18 | 10 | 12 | 9 |
| T | 5 | 13 | 17 | 20 | 0 | 0 | 0 | 0 | 12 | 13 | 7 | 4 |
| C | 10 | 5 | 7 | 10 | 0 | 0 | 0 | 0 | 5 | 7 | 8 | 18 |

TABLE 4

| | | |
|---|---|---|
| IK3-1 | aggcTTTTGGGAATACCAGacacc | (SEQ ID NO:75) |
| IK3-2 | aggcTTGGGATTGGGAATacacc | (SEQ ID NO:76) |
| IK3-3 | ggtgTTCCTGGGAATGTTCGgccta | (SEQ ID NO:77) |
| IK3-4 | aggcGTGGGAATATCAGGacacc | (SEQ ID NO:78) |
| IK3-5 | aggcTGGGAATGCTGGGAAacacc | (SEQ ID NO:79) |
| IK3-6 | ggtgTTGGGAATGCTGGAATgccta | (SEQ ID NO:80) |
| IK3-7 | ggtgTAATTGGGAATTTTTAgccta | (SEQ ID NO:81) |
| IK3-8 | ggtgTGGGAAAAGTGGGAATgccta | (SEQ ID NO:82) |
| IK3-9 | ggtgTTCCTGGGAATGCCAAgccta | (SEQ ID NO:83) |
| IK3-10 | aggcTACAGAATACTGGGAacacc | (SEQ ID NO:84) |
| IK3-11 | aggcTAAAAATTCCTGGGAacacc | (SEQ ID NO:85) |
| IK3-12 | aggcATTCCCGTTTTGGGAacacc | (SEQ ID NO:86) |
| IK3-13 | aggcATTCCCGTTTTGGGAacacc | (SEQ ID NO:87) |
| IK3-14 | ggtgTATCCCGGGAATACCGgccta | (SEQ ID NO:88) |
| IK3-15 | aggcTAAGGAATACCGGGAacacc | (SEQ ID NO:89) |
| IK3-16 | aggcTCTGGAATATCGGGAacacc | (SEQ ID NO:90) |
| IK3-17 | ggtgTAAATCGGGAATTCCgccta | (SEQ ID NO:91) |
| IK2-18 | aggcCGGGAATACCGGAAAacacc | (SEQ ID NO:92) |
| IK2-19 | aggcAAAACATTACAGGGAacacc | (SEQ ID NO:93) |
| IK2-20 | aggcAGGGAATATGGGATacacc | (SEQ ID NO:94) |
| IK3-21 | ggtgTAGGAATTCTAGGAATgccta | (SEQ ID NO:95) |
| IK3-22 | aggcATTCCAAGGAATTTacacc | (SEQ ID NO:96) |
| IK3-23 | ggtgTAAGGAATACTGGAATgccta | (SEQ ID NO:97) |
| IK2-24 | ggcAGAATTCCAAGGAATacacc | (SEQ ID NO:98) |
| IK3-25 | aggcCAAGGAATATCAGGAcacc | (SEQ ID NO:99) |

| | T | N | A/C or T | T | G | G | A | A | T | A/G | C/T | C/T |
|---|---|---|---|---|---|---|---|---|---|---|---|---|
| | -3 | -2 | -1 | 1 | 2 | 3 | 4 | 5 | 6 | 7 | 8 | 9 | 10 |
| G | 7 | 5 | 3 | 0 | 20 | 25 | 25 | 0 | 0 | 0 | 5 | 0 | 0 |
| A | 3 | 8 | 0 | 6 | 5 | 0 | 0 | 25 | 25 | 0 | 16 | 1 | 1 |
| T | 15 | 4 | 9 | 14 | 0 | 0 | 0 | 0 | 0 | 18 | 4 | 6 | 7 |
| C | 0 | 8 | 13 | 5 | 0 | 0 | 0 | 0 | 0 | 7 | 0 | 18 | 17 |

TABLE 5

| | | | |
|---|---|---|---|
| TCEα enhancer | | | |
| | m | TGGAGGGAAGTGGGBAAACTTTT | (SEQ ID NO:103) |
| | | TGGAAGTGGGAGGC | (SEQ ID NO:104) |
| | | GAGGAGAAAGGTCTCCTAC | (SEQ ID NO:105) |
| TCRβ enhancer | | | |
| | h | AACAGGGAAACA | (SEQ ID NO:106) |
| | m | GTCAGGGAAACAGG | (SEQ ID NO:107) |
| | h | AAGGTGGGAAGTAA | (SEQ ID NO:108) |
| | h | GGTAGGAATBGG | (SEQ ID NO:109) |
| | m | GGAGGGGGAAGAA | (SEQ ID NO:110) |
| | m | AGTGGGGAAAABTCT | (SEQ ID NO:111) |
| | m | GGTCAGGGAAACAA | (SEQ ID NO:112) |
| | m | TGGGGGAAGGGGTGGAAG | (SEQ ID NO:113) |
| | m | TTTTGGGAACC | (SEQ ID NO:114) |
| | m | AAAGGGGAACCC | (SEQ ID NO:115) |
| | h/m | TGGAGGGAG | (SEQ ID NO:116) |
| promoter | | | |
| | m | AGGGGAAA | (SEQ ID NO:117) |
| | | TTTGGGAATT | (SEQ ID NO:118) |
| | | TGAGAGGAAGAGGAGA | (SEQ ID NO:119) |
| | | CAGGAATT | (SEQ ID NO:120) |
| TCR-δ enhancer | | | |
| | δE5/m | AAGGAAACCAAAACAGGGGAAG | (SEQ ID NO:121) |
| | δE3/m | TTGGAAACCT | (SEQ ID NO:122) |
| CD3-δ enhancer | | | |
| | δA/h | GTTTCCATGACATCATGAATGGGACT | (SEQ ID NO:123) |
| | /m | GTTTCCATGATGTCATGAATGGGGT | (SEQ ID NO:124) |
| | | TTCTTGGGGATTG | (SEQ ID NO:125) |
| CD3-γδ promoter | | | |
| | m | GGAGGAACT | (SEQ ID NO:126) |
| | m | TTTGGGATG | (SEQ ID NO:127) |
| | m | TTCTAGGAAGTAAGGGAATTT | (SEQ ID NO:128) |
| | m | GTGGGAAGA | (SEQ ID NO:129) |
| | m | TAGGAATTCT | (SEQ ID NO:130) |
| | m | TAAGGAAAGG | (SEQ ID NO:131) |
| | m | TTTCCAAGTGGGAATC | (SEQ ID NO:132) |
| CD3-ε enhancer | | | |
| | m | TGGGACAAGATTTCCA | (SEQ ID NO:33) |
| | m | TGGGGAAGTGAAGGAGGGAGG | (SEQ ID NO:34) |

TABLE 5-continued

|  |  |  |  |
|---|---|---|---|
|  | m | GAGGGGGATC | (SEQ ID NO:35) |
| CD4 promoter |  |  |  |
|  | m | TGGGGAAGTT | (SEQ ID NO:133) |
| CD 2 promoter |  |  |  |
|  | m | TTGGGAAGGAT | (SEQ ID NO:134) |
|  | m | AAGGAACA | (SEQ ID NO:135) |
| IL2-R α promoter/NFkB |  |  |  |
|  | h | CAGGGGAATCTCCCTCTCCAT | (SEQ ID NO:136) |
| IL2 enhancer |  |  |  |
| PuBp |  | AAGAGGAAAA | (SEQ ID NO:137) |
| PuBd(NFAT-1) |  | AGGAGGAAAA | (SEQ ID NO:148) |
| β-IFN(PRDII)/NFkB |  |  |  |
|  |  | GGGAAATTCC | (SEQ ID NO:138) |
| MHC classII/NFkB |  |  |  |
|  | m | GGGGAATCC | (SEQ ID NO:139) |
| TDT-promoter/LYF |  |  |  |
|  |  | TGGGAG | (SEQ ID NO:140) |
| mb-1 promoter/EBF |  |  |  |
|  |  | CAAGGGAAT | (SEQ ID NO:72) |
| HIV LTR |  |  |  |
|  |  | CAGGGAAGTA | (SEQ ID NO:141) |
|  |  | CAAGGGACTTTCCGCTGGGGACTTT |  |
|  |  | CCAGGGAGGGCG | (SEQ ID NO:142) |

A consensus recognition sequence for each of these proteins was derived. The mIk-1, mIk-2 and mIk-3 core motifs were, respectively;

N-N-[T/a/c]-T-G-G-G-A-A-T-[A/g/t]-[C/t]-[C/t] (SEQ ID NO:155)

N-N-[T/c]-[T/c]-G-G-G-A-[A/T]-N-N-C (SEQ ID NO:156) and

T-N-[C/t]-T-G-G-G-A-A-T-[A/t/g]-[C/t]-[C/t] (SEQ ID NO:157).

The mIk-1 and mIk-3 sequences shared the seven base pair core T-G-G-G-A-A-T (SEQ ID NO:149). The mIk-3 protein showed strong reference for particular nucleotides both at the 5' and 3' flanking positions of this motif while the mIk-1 protein did not select for any particular bases at these positions. The mIk-2 consensus shared five bases with the mIk-1 and mIk-3 heptanucleotide and exhibited great degeneracy outside this sequence. This may permit for the mIk-2 protein to bind with high affinity to a wider range of recognition sequences. Another feature of the oligonucleotides selected by the mIk-3 protein is that 85% of them contained a second consensus (as underlined in Table 2). In contrast, only 50% and 38% of the oligonucleotides selected by mIk-1 and mIk-2 respectively had the potential for a second binding site (as underlined in Table 1 and 3). Such double recognition sequences were also selected by the truncated Ikaros proteins (which lack the C-terminal finger domain) suggesting the interaction between their N-terminal finger domain and these sequences. This may suggest differences in the affinity of mIk-1, mIk-2 and mIk-3 for the selected core motif. Double recognition sequences may allow for an increase in the apparent binding affinity of these proteins for these sites.

The N-terminal truncated forms of mIk-1, mIk-2 and mIk-3, after 4, 6 and 7 rounds of selections respectively, bound to a significant amount of the selected pool of oligonucleotides. Analysis of a limited number of cloned oligonucleotides revealed a core consensus similar to the one selected by their full length counterparts. In contrast, the truncated proteins comprising the C-terminal two zinc fingers (F5 and F6) did not appear to bind to any significant proportion of the oligonucleotide pool and to select for any specific sequence.

Binding site selections were performed as follows. A pool of random oligomers was designed with 25 base pairs of defined sequence at the 5' an 3' (including BamHI and EcoRI restriction sites) and 15 bases of random sequence in the middle. In the first round of selections Ikaros-GST fusions attached to gluathione agarose beads (20 μls bead volume) were used in binding assays together with 500,000 cpm of end labeled random primers. After a 20 minute binding reaction on ice the beads were spun down gently and washed twice to three times with ten fold excess of ice cold 1×binding buffer. Bound primers were eluted in 0.1% SDS 10 mMTris pH 7.5 recovered radioactivity was determined and then were phenol extracted and precipitated in the presence of 10 μgs of glycogen. ⅕th of recovered DNA was reamplified with primers complementary to the defined 5' and 3' sequences with α-$P^{32}$ dCTP included in the reaction to generate a homogeneously labeled pool of selected oligomers. All probes were gel purified. In higher rounds decreasing amounts of selected oligomers were used in the binding reactions in order to enrich for higher affinity sites (2000,000/100,000 cpm). Five rounds of selections were performed. At the end of the last round of the eluted DNAs were amplified, digested with EcoRI and BamHI restriction enzymes, cloned in pGEM3Z and sequenced with normal and reverse primers. Sequences of selected primers were aligned to a shared motif present in al DNAs.

Fusion protein and DNA binding studies were performed as follows. The coding region of the Ikaros isoforms were PCR amplified with Vent polymerase from their respective cDNAs using primers and cloned into the BamHI/EcoRI sites of pGEXIII. Recombinant plasmids were analyzed by sequencing. Overnight cultures of the appropriate recombinant pGEX vectors were diluted by ten fold and grown at 37° C. for 90 minutes before a 3 hours induction with 2 mM IPTG at 26° C. Crude bacterial lysates were produced as previously described (Georgopoulos 1992). Ikaros-GST fusions were partially purified on glutathione agarose beads, eluted in buffer D containing 20 mM free glutathione and 0.5M NaCl at 4° C. for 1 hour. Eluted proteins were checked by SDS-Page there concentrations was estimated by the Lowry method and appropriate dilutions were used for DNA binding studies. DNA binding assays were performed. Binding reactions contained 50,000 cpm of labeled oligonucleotides (0.5–1 ng), 100 ngs of the fusion proteins, 0.1 μgs of dI/dC and the binding buffer was supplemented with 20 μM of $ZnCl_2$. Binding reactions for methylation interference assays were scaled up ten times and were performed as previously described (Georgopoulos 1990).

Binding Specificity of Ikaros Isoform mIk-1–5

The binding specificity of the five Ikaros proteins for a single recognition site derived from the selected consensus was tested in a gel retardation assay. A 24 bp oligonucleotide (IK-BS1, T-C-A-G-C-T-T-T-T-G-G-G-A-A-T-A-C-C-C-T-G-T-C-A) (SEQ ID NO:101) designed to accommodate high affinity binding of the three selecting proteins was tested in a gel retardation assay against equal amounts of the five Ikaros isoforms produced in bacteria as GST fusions. The Ikaros proteins interacted with the IK-BS1 site differentially. The mIk-1 isoform bound this sequence with the highest affinity followed by mIk-2 and mIk-3. in fact, scanning densitometry determined that the relative amounts of mIk-2 and mIk-3 complexes on the IK-BS1 DNA were 3.4 and 1.7 fold lower than that of the mIk-1 complex. Neither the mIk-4 or mIk-5 proteins bound this sequence. Apparently, the presence of only two or one zinc fingers at the N-terminus of mIk-5 and mIk-4 were not sufficient for their stable interaction with this site.

Given the number of potential double recognition sites selected by the Ikaros proteins, an oligonucleotide containing an inverted repeat of their core consensus was tested (IK-BS4) TCAGCTTTTGGGAATGTATTCCCTGTCA (SEQ ID NO: 73). Four of the five Ikaros proteins, including mIk-4, bound to this sequence with high affinity. In contrast to widely distinct binding affinities for a single recognition sequence, those isoforms appeared to interact similarly with this double recognition site. Significantly, the relative abundance of the mIk-2 protein complex on the palidromic IK-BS4 sequence was 6.3 fold higher than on the IK-BS1 single recognition site and its mobility was slower and indicative of a potential higher order complex. In addition, the mIk-4 protein which did not bind to IK-BS1, bound to the palindromic sequence with high affinity. This strongly suggests cooperative binding of mIk4 and possibly mIk-2 proteins respectively, on proximal binding sites. The relative affinities of mIk-1 and mIk-3 were also enhanced, but to a lesser extent (2.3 and 3.5 fold respectively). Interestingly, the mobility of the mIk-1 complex was similar on both single and double recognition sequences. This may reflect stable dimer formation of this protein in solution or, alternatively, the conformation of the mIk-1 protein may prevent double occupancy of sites in proximity.

To determine whether the high affinity binding of the mIk-2 and mIk-4 proteins on IK-BS4 was due to an increase in the local concentration of binding sites or whether this was mediated by protein-protein interactions, the spacing between the two half sites was decreased to allow only for single site occupancy. The mIk-1, mIk-2 and mIk-3 proteins bound with similar affinities to the single site in the IK-BS6 oligomer which contains two inverted and partially overlapping core motifs, as they did to the IK-BS 1 oligonucleotide. (IK-BS6) TCAGCTTTTGGGAATTCCCTGTCA (SEQ ID NO: 74). The mIk-4 protein did not bind to IK-BS6, strongly implicating its cooperative binding on proximal and appropriately spaced binding sites.

The Ikaros heptanucleotide core motif displays strong sequence similarities with a subset of NF-κB sites,e.g., NF-κ sites in IL-2Rα, H2-K$^b$ β-interferon promoters. The NF-κB recognition sequence is an imperfect palindrome with a certain degree of base pair variation in the middle of the motif. These sequences bind with high affinity homo- and heterodimeric complexes formed between members of the NF-κB/rel family. The IK-BS2 oligonucleotide (TCAGCTTTTGGGAATCTCCTGTCA, SEQ ID NO: 100) which contains an Ikaros consensus sequence in the context of the IL2-Rα promoter NF-κB site was tested for binding the Ikaros proteins. The mIk-1 and mIk-2 proteins bound to the IK-BS2 with affinities similar to those shown for the selected IK-BS1 oligonucleotide. However, binding of the mIk-3 isoform to this site was greatly reduced, probably due to a non-conservative base pair substitution at position 8 of its consensus motif. Interestingly, the mIk-4 protein, which bound only to the palindromic sequence in the IK-BS4 oligonucleotide, also bound to the IK-BS2 oligonucleotide. This is probably due to the presence of a related motif on the bottom strand of this oligonucleotide which creates an imperfect palindrome. A higher order binding complex was again observed between the mIk-2 protein and the IK-BS2 oligonucleotide.

The IK-BS7 oligonucleotide (TCAGCTTTTGAGAATACCCTGTCA) (SEQ ID NO:158), with a base pair substitution within the core consensus was tested for its ability to interact with the Ikaros proteins. A single base pair change at position 3 of the consensus, which substituted an adenine for the conserved guanine abrogated binding of the Ikaros proteins, underscoring the importance of this conserved residue. Substitution of a thymidine for an adenine at position 6 (e.g., to generate IK-BS3, TCAGCTTTTGGGATTACCCTGTCA, SEQ ID NO: 159) in the selected consensus prevented binding of the mIk-3 and mIk-4 proteins and decreased the relative affinity of the mIk-1 isoform by 2–3 fold. However there was no effect on the binding of the mIk-2 protein that selected for either bases at this position with a similar frequency. Non-conservative substitutions at the 3' of the mIk-1/-3 decanucleotide consensus (IK-BS9, TCAGCTTTTGGGAAAAACCTGTCA, SEQ ID NO: 160) abolished mIk-3 and mIk-4 binding, reduced the affinity of the mIk-1 protein but did not significantly affect the mIk-2-DNA interactions. Nevertheless, substitutions of four guanines for the thymidines at the 5' of the core consensus had a negative effect on the binding of all of Ikaros proteins (IK-BS5, TCAGCGGGGGGGAATACCCTGTCA, SEQ ID NO:152).

Of the Ikaros isoforms, only mIk-5 with a single N-terminal zinc finger did not bind to any of the tested oligomers including the ones that contained a double recognition site. However, the C-terminal finger domain was shown to be able to bind to the δA element of the CD3δ enhancer in a sequence specific manner. Consequently, we tested binding of the Ikaros isoforms to the δA motif (GTTTCCATGACATCATGATGGGGT, SEQ ID NO: 161). Two sequence specific binding complexes were formed with the mIk-1, mIk-2 and mIk-3 proteins that differed substantially in their relative abundance. Only the faster migrating complex was detected with the mIk-4 and mIk-5 proteins. Formation of this complex on the δA element may involve the C-terminal finger domain present in all of the Ikaros proteins. The mIk-5 isoform in particular with only one finger at its N-terminal domain may primarily utilize these C-terminal fingers for sequence specific DNA binding. However, these C-terminal zinc fingers were not able to select for any sequence motif in the binding site selections described previously. This may be due to low affinity protein-DNA interactions which do not stand up to the stringency of the selection assays and may also reflect a complexity in the DNA binding site not accommodated by the size of the random sequence in selecting oligonucleotides.

Since the Ikaros proteins belong to the Cys$_2$-His$_2$ zinc finger family of DNA binding proteins, the role of these N-terminal zinc fingers in determining sequence specificity can be predicted. The $Cys_2$-$His_2$ zinc finger proteins make base pair contacts by aligning their finger modules along the major grove of their recognition site in an anti-parallel fashion (Pavletich and Pabo (1991) *Science* 252:809–818), and in a protein with multiple zinc fingers, each module is capable from zero to a maximum of five base contacts (Pavletich et al. (1993) *Science* 261:1701–1707). The mIk-1 and mIk-3 proteins, with four (F1+F2+F3+F4) and three (F1+F2+F3) N-terminal fingers respectively, each selected the ten base pair consensus T-G-G-G-A-A-T-A-C-C (SEQ ID No. 162). mIk-3, with one finger less (–F4) than mIk-1, made more DNA contacts and displayed a stricter DNA specificity (T-N-C/t-T-G-G-G-A-A-T-A-C-C for Ik-3 (SEQ ID No. 157) versus N-N-T-T-G-G-G-A-A-T-A/g-C-C for Ik-1, (SEQ ID No. 155)). However, mIk-1 bound to this recognition site with higher affinity. This suggests that finger -4, expected to make the most 5' base pair contacts, is not directly involved in DNA binding. Nevertheless, this finger module may dictate the specificity and affinity of the N-terminal DNA binding domain by affecting its protein conformation. The mIk-2 protein, with three N-terminal fingers (F2+F3+F4), selected the six base pair motif T-G-G-G-A-A/t (SEQ ID No. 156) contained within the selected consensus for mIk-1 and mIk-3. However the mIk-4 isoform, with the same two N-terminal fingers (F2+F3) as mIk-2 but lacking finger -4, did not bind to single recognition sites, and interacted only with appropriately spaced double recognition sequences in a cooperative fashion. The N-terminal zinc finger domain of the Ikaros proteins and its role in dictating their DNA binding specificities and affinities is reminiscent of a similar domain in the Evi-1 gene. The Evi-1 protein is comprised of seven N-terminal and three C-terminal zinc fingers and is involved in regulating differentiation in the myeloid lineage. The first three zinc finger motifs in this protein do not bind DNA but they determine the overall DNA binding specificity of the N-terminal domain (Delwel et al. (1993) *Mol Cell Biol* 7:4291–4300). The differential usage of zinc fingers by the Ikaros proteins is also reminiscent of the Drosophila chorion transcription factor CF2 which, by alternate splicing, encodes proteins with distinct combinations of $Cys_2$-$His_2$ zinc finger motifs. These zinc finger containing proteins, in a similar fashion to the Ikaros isoforms, display overlapping yet overall distinct DNA binding specificities (Gogos et al. (1992) *Science* 257:1951–1955; and Hsu et al. (1992) *Science* 257:1946–1950). In conclusion, the DNA binding specifically and affinity of an Ikaros protein with two or more fingers at its N-terminal part, is primarily dictated by these N-terminal fingers.

Chemical Footprinting of Ikaros Isoforms mIk-1–4 on their cognate sites

The protein/DNA interactions of mIk-1–4 were further established by chemical footprinting. The IK-BS2 oligonucleotide (TCAGCTTTTGGGAATCTCCTGTCA) (SEQ ID NO:102) that binds with high affinity to the four isoforms was used in a methylation interference assay. On the positive strand all four proteins gave similar footprints, indicating similar contacts. Methylation of the three guanines at positions 2, 3 and 4 of the consensus interfered 100% with the binding of all four proteins. The mIk-2 protein made additional major grove contacts with the guanine at position -5 and with the adenine at position 5. Methylation of adenines at position 5 and 6 enhanced binding of mIk-3 and mIk-2 respectively. However, on the negative strand, the four proteins made dramatically different contacts. The most extended footprint was that of mIk-4 which covered the purines from positions 8 through 12, while mIk-3 made contacts with bases at positions 7 through 10. The mIk-1 and mIk-2 proteins made only one full contact with the guanine at position 10, while mIk-1 also made partial contact with the purines at positions 7 through 9.

Of the three proteins used in the selections, mIk-3, with the strictest consensus, made the most base pair contacts on the negative strand. The overall foot print made by this protein suggests extensive interactions between fingers -1, -2, and -3 with eight of the tem bases of its recognition site. On the same recognition site, the mIk-2 protein, the most promiscuous of the three, made only six base pair contacts suggesting limited interaction between finger -4 and DNA. Surprisingly, the mIk-1 protein, containing fingers -1, -2, -3 and -4, made less full base pair contacts than the mIk-3 protein with fingers -1, -2 and -3. This suggests that the additional finger -4 present in mIk-1 may influence the ability of the other fingers and especially of finger -1 to interact with DNA, perhaps by dictating a different overall protein conformation. Finally the extensive and qualitatively distinct footprint made by mIk-4 further support the cooperative occupancy of close proximity recognition sites by this isoform of Ikaros. These methylation interference data demonstrate that the four Ikaros proteins make qualitative distinct DNA contacts and underling their ability to bind DNA differentially.

Transcriptional activation by the IK proteins.

The ability of the Ikaros proteins to activate transcription from a promoter juxtaposed to tandem copies of low and high affinity binding sites was tested in transient expression assays in NTH-3T3 fibroblasts. In one set of experiments, reporter genes (e.g. tkCAT expression constructs) under the control of four copies of the IK-BS 1, IK-BS2 or IK-BS9 sites were cotransfected together with plasmids expressing each of the four Ikaros cDNAs mIk-1, mIk-2, mIk-3 and mIk-4 in NIH-3T3 fibroblast cells. Expression of mIk-1 increased the activity of the tkCAT gene under the control of the high affinity binding sites, IK-BS1 and IK-BS2, by 11 and 19 fold respectively, but stimulated the activity of this reporter gene under the control of the low affinity binding site IK-BS9 by only 3.3 fold. Expression of the mIk-2 protein increased the activity of the IK-BS2 reporter gene by 11 fold, but only stimulated the activity of the IK-BS1 and IK-BS9 reporter genes by 2–3 fold. However, the affinity of mIk-2 for the binding sites in the three reporter plasmids is similar. It is noteworthy that a higher oder mIk-2 binding complex was only detected on the IK-BS2 oligonucleotide.

Binding site composition also appeared to play a role in the ability of the mIk-1 isoform to activate transcription. Although the mIk-1 protein can bind the IK-BS1 and IK-BS2 sites with similar affinities, and to the IK-BS9 site with only a two fold difference, its ability to stimulate transcription from these sites was markedly different. Expression of the mIk-1 isoform stimulated the activity of the IK-BS2 reporter to a 6 fold higher level than than of the IK-BS9 reporter.

Transcriptional stimulation of these reporter constructs by the mIk-3 and mIk-4 proteins was markedly lower. Expression of either mIk-3 or mIk-4 stimulated transcription only by -2 to -3 fold even from constructs containing high affinity binding sites for these isoforms. This effect was not due to differences in protein stability or expression in these assays, since a similar number of transfected cells with comparable levels of immunoreactive material were detected upon immunohistochemical analysis of transfected fibroblasts.

Difference in the transcriptional activity of mIk-1, mIk-2, mIk-3 and mIk-4 proteins combined with overlapping sequence specificities may be the key in regulating the activity of a number of control elements involved in lymphocyte specific gene expression. For example, mIk-4, a very weak transcriptional activator, could effectively compete with the mIk-1 and mlk-2 proteins on composite binding sites (e.g. on the IL2-Rα/NFκB site) during early T cell development when it and these isoforms are expressed at similar levels.

Thus, either naturally occurring isoforms, or those produced by mutagenesis, may function to attenuate transcription from binding sites that also accommodate such isoforms as mIk-1 and mIk-2.

The mIk-1 and mIk-2 proteins were not able to activate transcription from a mutant binding site which did not bind any of these factors demonstrating that their activation potential is sequence specific.

Since the sequence composition for an Ikaros high affinity binding site is identical to the NFκB motifs present in the IL2-Receptor α and the β-interferon promoters its transcriptional activity in a mature T cell line in the absence and in the presence of mitogenic stimulation was examined. The human Jurkat T cell line was chosen for the following reasons. First the activity of NFκB recognition sequences that closely match the selected Ikaros binding sites have been extensively studied in this cell line and secondly because it is determined, as described herein, that the human Ikaros gene is highly conserved to the mouse gene in both amino acid composition and splicing variants. In contrast to previous reports, high levels of transcriptional activity from this multimerized site were detected which were not further stimulated upon mitogenic treatment. This activity was decreased by five fold when Ikaros antisense expression vectors were cotransfected together with this reporter gene. No such effect was detected when reporter genes driven by the RSV or SL3 LTRs were used in a parallel experiment suggesting that transcriptional inhibition by the Ikaros antisense RNA is specific to this site.

Transcriptional activation from a reiterated NFκB variant in NIH3T3 fibroblasts upon expression of Ikaros 1–4 isoforms was determined as follows. The stimulation of CAT activity in the presence of the Ikaros proteins was evaluated as the ratio of activity when cotransfected with a recombinant CDM8/CDM8 vector alone. This data represent an average of three/four experiments with each combination of transfected plasmids per experiment repeated twice. All transfections were normalized to GH levels as described in materials and methods.

Activity and repression of the reiterated NFκB like element in human T cells was determined as follows. The reporter gene under the control of IK-BS2 (FNKB like variant) or of RSV and SL3 LTRs was transfected in Jurat cells in the presence of CDM8 expressing Ikaros antisense plasmids. Fold induction relative to enhancerless plasmid and suppression in presence of antisense RNAs was determined.

Mammalian expression vector and transfection experiments were performed as follows. The five Ikaros isoforms were subcloned into the HindIII-Not I site of the CDM8 expression vector. The tkCAT reporter gene constructs, under the control of four sense copies of IKBS1 IKBS2, IKBS9, were cotransfected with the appropriate CDM8 expression vectors (e.g., for expressing a particular Ikaros isoform), in the NIH 3T3 fibroblasts and the mature T cell line Jurkat. Cells were harvested 36–48 hours later and analyzed for CAT activity and Growth hormone levels. Results determined as the average of ¾ independent experiments where each combination of reporter to expression plasmids was performed twice.

Target sites for the Ikaros proteins in lymphoid restricted regulatory domains.

Potential high affinity binding sites for the Ikaros proteins, e.g. containing the core motif G-G-G-A-A, were found in the enhancer and promoter regions of the regulatory domains of the members of the TCR antigen complex, i.e. the TCR-α, -β, and -δ, the CD3 -δ, -ε, and -γ genes, the SL3 and HIV LTR and in the regulatory domains of other T cell restricted antigens (Table 5). These sequences represent high affinity binding sites as determined by gel retardation assays. The multiplicity and often the proximity of potential high affinity binding sites in the regulatory domains of these genes was striking. Some of these sites can bind all four proteins while others interact only with mIk-2 and mIk-1 isoforms. High affinity binding sites for the Ikaros proteins were also found in the promoters of costimulatory T cell differentiation antigens CD4 and CD2, in the early pre-B cell differentiation antigen mb-1, and also in the NF-κB motifs present in the promoter of the IL2-Rα, in the PRDII element of the β-interferon gene, in the enhancer of the H-2K$^b$ gene and in the E-A$^d$ promoter. Four of the Ikaros proteins can bind with high affinity to these NF-κB sites.

Related sequences to the Ikaros motif were also found in the above described regulatory domains as well as to the Ikaros motif were also found in the above described regulatory domains as well as in the purine boxes of the IL2 gene, in the TDT gene, as well as in the NFkB variant sites of the HIV-LTR and in the early pre-B cell differentiation antigen mb-1 (Table 5). Single sites containing these related sequences bind substantially better to such sites present in proximity. This is clearly the case with the CD3 δA element which is comprised of two low affinity binding sites and possibly with other regulatory elements. The presence and proximity of low affinity binding sites may also influence the occupancy of the high affinity binding sites in these various regulatory domains and may dictate the sequential activation of the respective target genes during lymphocyte development.

As described above, to investigate the affinity of the Ikaros proteins for these sites, their ability to compete with the selected recognition sequences was studied. Base pair substitutions within and outside the seven base pair motif were introduced to match the sequence composition of some of these sites present in the lymphoid and T cell specific regulatory domains. Oligonucleotides with the appropriate base pair changes were used in competition experiments against the consensus motif (IKB-S1).

The IK-BS2 oligonucleotide, identical to the IL2-Rα NFkB motif, bound to the four proteins with a two fold higher affinity than a single copy of the consensus motif. We believe that this is due to the second low affinity binding site in the opposite strand.

The existence of low affinity binding sites in close proximity in a regulatory domain increases the relative affinity of the Ikaros proteins for these sites. This is clearly the case with δA and possibly with other elements. The occupancy of high affinity binding sites could also be affected by low affinity sites in the immediate region. The apparent binding constant of these proteins for these sites may raise to an even higher value and could dictate the order of target genes activated by the Ikaros enhancers in the developing lymphocyte.

Nuclear complexes forming over Ikaros recognition sites

The composition of T cell nuclear complexes formed over the recognition sites selected by the Ikaros proteins was examined. The IK-BS4 oligonucleotide, a high affinity binding site for four of the Ikaros binding forms, was tested with nuclear extracts made from the T cell line EL4. Two sequence specific nuclear complexes were formed as determined by competition with 100 fold molar excess of the IK-BS4 and IK-BS7 oligonucleotides. Both complexes were supershifted by two different antisera raised against the C- and N-terminal domains of the Ikaros protein respectively. The majority of the IK-BS4 binding complexes were supershifted by these antibodies, but some binding activity remained. Distinct nuclear factors with similar mobility properties to the Ikaros proteins may be responsible for this residual binding. The supershifted complexes were not formed in the absence of the EL4 nuclear proteins supporting a specific interaction between antibodies and protein-DNA complexes. These Ikaros antibodies did not interact with other proteins that can also bind with high affinity to this site (e.g. the p50 homodimer member of the NF-κB complex). In addition, antibodies raised against the other member of the NF-κB complex, the p65 protein, or against an unrelated protein, had no effect on these nuclear complexes. It is therefore suggested that the majority of the T cell nuclear complexes forming over high affinity Ikaros binding sites are comprised of proteins that belong to the Ikaros family.

Cloning of the human Ikaros gene

A DNA fragment derived from the shared 3' coding region of the mouse Ikaros cDNAs was used as a probe to screen for human Ikaros homologs. This DNA fragment, which encodes the C-terminal part of the Ikaros proteins, is believed to be essential for their activity and does not exhibit significant sequence similarities with other DNA binding proteins. A cDNA library from the human T cell line Jurkat was screened at high stringency and 9 partial cDNAs were isolated. The most full length cDNA and its deduced amino acid sequence is shown in FIG. 3 (SEQ ID NO:3). This cDNA encodes a protein homologous to the mouse Ik-1 isoform, the largest of the mouse Ikaros proteins comprised of all the translated exons. A high degree of conservation was detected between the human and the mouse Ik1 isoforms both at the DNA and the protein levels. The portion of the mouse Ik-1 that contains exons 3 through 7 display 89% and 91% identity to its human homologue at the DNA and protein levels respectively. However the N-terminal portion of the mouse Ik-1 isoform encoded by exons 1/2 was not found in any of the three human cDNAs. The cDNAs instead display distinct 5' ends. The lack of conservation in this part of the human and mouse Ikaros proteins suggest that each of their N-terminal portions are probably not functionally significant. The distinct 5' untranslated sequences present in these human cDNAs are reminiscent of the number of distinct 5' untranslated sequences present in mouse cDNA products of potential alternate promoter usage.

Of the human cDNAs isolated, only one contained the splicing junction between exons-4 and -6 found in the mouse Ik-4 isoform. The lower frequency of cloning of human Ik-4 relative to human Ik-1 cDNAs may reflect their relative concentrations in this T cell line. In the mouse, the Ik-1 isoform is found in excess relative to the Ik-4 isoform in the differentiating T cells (A. Molnar et al 1994).

Human Ikaros isoforms were cloned as follows: A human cDNA library made from the mature T cell line Jurkat (Stratagene) was screened with a 150 bp single stranded probe derived from the most 3' of the IK-1 mouse Ikaros cDNA. From the $8 \times 10^5$ recombinant phages screened, 9 positive clones were obtained. Filters with recombinant phage DNA were incubated overnight in hybridization buffer (7% SDS, 1% BSA, 0.25 Sodium-phosphate pH 6.5 and 0.5 mM EDTA) with $1 \times 10^6$ cpm/ml probe at 65° C.

Washes were performed twice in 2×SSC/1% SDS, 0.2×SSC/1% SDS and 0.2×SSC/01% SDS at 65° prior to autoradiography. Positive clones were purified and characterized by dideoxy sequencing.

Expression of the Ikaros gene in human tissues and cell lines.

Expression of the Ikaros gene was determined in human tissue and cell lines. Two major Ikaros RNA transcripts were detected only in polyA+ RNA from thymus, spleen, and peripheral leukocytes. Very low levels of Ikaros mRNA was also detected in the colon, and probably reflects the resident lymphocyte population in this tissue. The smaller (28S) of the two Ikaros mRNA forms correlates in size with the major Ikaros transcript detected in the mouse, while the larger form correlates in size with a low abundance transcript detected in the mouse upon overexposure of Northern blots. High levels of both of these mRNAs were expressed in the thymus, while the larger form predominated in the spleen. In peripheral leukocytes equal amounts of both transcripts were present, but at 2 fold lower level than in the thymus. These two mRNA species detected in the human may represent products of differential splicing with the larger species containing additional 5' and/or 3' non coding exons. In addition, they may be transcribed from distinct promoters and may be comprised of different combinations of 5' untranslated exons.

Northern Analysis was carried out as follows: Two Northern blots each containing 2 μgs of poly A+ RNA isolated from human heart, brain placenta, lung liver, skeletal muscle kidney and pancreas (Clontech human blot) and from spleen, thymus, prostate testis ovary small intestine colon and peripheral blood leukocytes (Clontech human blot II) were hybridized with a probe ($10^6$ cpm /ml in hybridization buffer) made from the 800 bp SacI-EcoRI fragment of hlk-1 cDNA. A northern blot containing 10 μgs of total RNA prepared from the T cell leukemic lines: CEM, Molt-4, from the acute myelogenous leukemia KG1, the acute monocytic leukemia THP-1, the U937 histiocytic lymphoma, 30 μgs of the T cell line HPB 1 and 2.5 μgs of human thymus The Ikaros protein isoforms are conserved between mouse and man The expression of the Ikaros protein isoforms was examined in human and mouse T cell nuclear extracts by Western blotting. Nuclear extracts from mouse and human fibroblast and epithelial cells were used to determine the specificity of the Ikaros antibody. A number of crossreacting proteins were detected in the nuclear extract from the mouse EL-4 T cell line. Since cDNAs that encode at least five size distinct Ikaros proteins were cloned from this cell line, the proteins detected with the Ikaros antibody are probably Ikaros isoforms expressed in this cell line. In the human T cell line Jurkat, the largest of these proteins was the most abundant form but other smaller proteins were detected at lower abundance. These human T cell nuclear proteins may represent the homologues of the mouse Ik-1, Ik-2, Ik-3 and Ik-4 isoforms in order of decreasing relative concentration. No crossreacting proteins were detected in the nuclear extracts from the CV1 and NIH-3T3 non expressing cell lines, thus confirming the specificity of the detecting antibody Western analysis of human and mouse nuclear extracts were carried out as follows: 20 μgs of protein, from nuclear extracts prepared from the Ikaros expressing mouse and human T cell lines EL4 and Jurkat, and from the Ikaros non-expressing mouse and monkey fibroblast and kidney epithelial lines NIH-3T3 and CV1, were run on 12% PAGE. Proteins were transferred to a nitrocellulose membrane and were analyzed with a 1:250 dilution of Ikaros antibody raised to the N-terminal portion of the mouse Ik-2 isoform containing exons 1, 3, 4, 5, and 6. The second step was performed using 1:3000 dilution of goat anti-rabbit antibody (BioRAD) conjugated to alkaline phosphatase. Antibody complexes were detected with BCIP and NBT substrates.

The Ikaros mouse genomic locus

Based on sequence analysis of variant cDNAs, the genomic locus is thought to include about 9–11 exons. Genomic DNAs encompassing most or all of the Ikaros exons present in the genome were isolated by screening a mouse genomic SV129 library made into the λDASH II phage vector using the various Ikaros cDNAs as probes. The Ikaros gene includes at least 80–90 kb of genomic sequence which was isolated as distinct but also overlapping genomic clones. Some of the Ikaros genomic clones are indicated in FIGS. 7. The exons are depicted as boxes while the introns as lines. The DNA sequence for: the 5' boundary (SEQ ID NO:143) and the 3' boundary (SEQ ID NO:144) of exon E5; the 5' boundary (SEQ ID NO:145) of exon E3; and the 5' boundary (SEQ ID NO:146) and the 3' boundary (SEQ ID NO:147) of exon E7, were determined.

The mouse Ikaros gene is located at the proximal arm of chromosome 11

The mouse chromosomal location of Ikaros was determined by interspecific backcross analysis using progeny derived from matings of [(C57BL/6J×F1 X C57BL/6J] mice. This interspecific backcross mapping panel has been typed for over 1300 loci that are well distributed among all the autosomes as well as the X chromosome. C57BL/6J and M spretus DNAs were digested with several enzymes and analyzed by Southern blot hybridization for informative restriction fragment length polymorphisms (RFLPS) using a mouse cDNA fragment as a probe. The 6.5 kb M. Spretus PstI restriction-fragment-length polymorphism (RFLP) was used to follow the segregation of the Ikaros locus in backcross mice. The mapping results indicated that Ikaros is located in the proximal region of mouse chromosome 11 linked to Lif, Erbb and Rel. Although 129 mice were analyzed for every marker, up to 157 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere- Lif - 6/167 - Ikaros - 3/146 - Erbb - 6/158 - Rel. The recombination frequencies [expressed as genetic distances in centiMorgans (cM) ± the standard error] are - Lif- 3.6±1.4 - Ikaros - 2.1±1.2 - Erbb - 3.8±1.5 - Rel.

The interspecific map of chromosome 11 was composed with a composite mouse linkage map that report s the map location of m any uncloned mouse mutations (compiled by M. T. Davisson, T. H. Roderick, A. L. Hillyard, and D. P. Doolittle and provided from GBASE, a computerized database maintained at The Jackson Laboratory, Bar Harbor, Me.). Ikaros mapped in a region of the composite map that lacks mouse mutations with a phenotype that might be expected for an alteration in this locus.

The proximal region of mouse chromosome 11 shares a region of homology with human chromosomes 22, 7 and 2. In particular Erbb has been placed on human 7p12. The tight linkage between Erbb and Ikaros in mouse suggests that Ikaros will reside on 7p as well.

Interspecific backcross progeny were generated by mating (C57BL/6J×M. spretus) F1 females and C57BL/6J males as described (Copeland and Jenkins, 1991). *Trends Genet* 7:113–118. A total of 205 F2 mice were used to map the Ikaros locus DNA isolation, restriction enzyme digestion, agarose gel electrophoresis, Southern blot transfer and hybridization were performed essentially as described (Jenkins et al. (1982) *J Virol* 43:26–36; and Jenkins et al (1982) *J Virol* 42:379–388). All blots were prepared with Zetabind nylon membrane (AMF-Cuno). The probe, a 350 bp mouse cDNA fragment was labeled with [$\alpha$-$^{32}$P] dCTP using a random prime labeling kit (Amersham); washing was done to a final stringency of 1.0×SSCP, 0.1% SDS, 65° C. A fragment of 8.4 kh was detected in PstI digested C57BL/6J DNA and a fragment of 6.5 kb was detected in PstI digested M. spretus DNA. The presence or absence of the 6.5 kb M. spretus-specific PstI fragment was followed in backcross mice.

A description of the probes and RFLPs for the loci linked to Ikaros including leukemia inhibitory factor (Lif), avian erythroblastosis oncogene B (Erbb) and reticuloendotheliosis oncogene (Rel) has been reported previously (Karl et al. (1993) *Mol Cell Biol* 10:342–301; Karl et al. (1992) *Genetics* 131:103–173; and Karl et al. (1992) *Science* 256:100–102) Recombination distances were calculated using the computer program SPRETUS MADNESS. Gene order was determined by minimizing the number of recombination events required to explain the allele distribution patterns.

The Ikaros gene maps between p11.2–p13 on human chromosome 7

The human chromosome assignment of the Ikaros gene was performed using DNAs prepared from a panel of somatic cell hybrids made between human and rodent. Primers designed after non-conserved sequences at the 3' end of the human cDNAs were used to distinguish between the human and rodent genes. A 375 bp fragment, as predicted from the human Ik-1 cDNA was amplified from human DNA used as a control and from DNA prepared from the cell hybrid 10791 which contains chromosome 7. The identity of the amplified band was confirmed using a probe derived from this region. To fine map the location of the Ikaros gene a panel of somatic cell hybrids which contained parts of chromosome 7 fused to the rodent genome were analyzed. A hybridizing 10 kb BglII genomic fragment was detected with human genomic DNA. A fragment of similar size was readily detected with DNA from the cell lines Ru Rag 4-13 and 1365 Rag12-9. The former cell line contained the proximal arm of chromosome 7 while the latter contained the distal and part of the proximal up to segment p13. DNA from Rag GN6, a cell line that contains the whole distal arm of chromosome 7 and the proximal arm up to segment p11.2, did not hybridize. Another cell line which contained part of the proximal arm of chromosome 7 from p- to the telomere did not hybridize. This mapping restricts the location of the Ikaros gene between p11.2 and p13, placing it proximate to the Erbb gene locus, as predicted from the mouse.

PCR analysis of somatic cell hybrid DNA prepared from human mouse hamster and human-rodent somatic cell hybrids were used for the chromosome assignment of the human Ikaros gene DNAs from the following cell lines were used in PCR reactions h/h human-hamster hybrid h/m: human-mouse hybrid, 1 to 24 respectively 07299-h/h, 1082613-h/h, 10253-h/h, 10115-h/h 10114-h/h, 10629-h/h 10791-h/h, 10156B-h/h,10611-h/h, 10926B-h/h, 10927A-h/h 10868-h/h, 10898-h/h 10479-h/m 11418-h/m 10567-h/m 10498-h/m 11010-h/h 10449-h/h 10478-h/m 10323-h/m 10888-h/h, 06318B-h/h 06317-h/h 25 human 26 mouse and 27: hamster DNAs were also used in control reactions 100 ngs of these DNAs were used in a PCR reaction together with 150 ngs of primers hIK-1 GGCTGCCACGGCTTC-CGTATCCT (SEQ ID No. 163) and hIk-2: AGCG- GTCTGGGGAAACATCTAGGA (SEQ ID No. 164) designed after non-conserved sequences at the 3 min. of the human cDNA. Amplification parameters were: 95° C. for 5 min., 80° C. for 10 min. (with addition of 2.5 units of Taq polymerase), followed by 30 cycles at 93° C. for 1 min., 65° C. for 1 min. and 72° C. for 40", with an additional cycle at 93° C. for 5 min., 65° C. for 2 min. and 72° C. for 7 min. The amplified 375 bp product corresponds to the predicted size from the human cDNA. Fragment identity was confirmed by Southern hybridization with a probe derived from this region.

Fine mapping on human chromosome was further obtained by preparing 7 DNAs from a chromosome 7 hybrid panel which was used either in PCR amplification reactions with the primers described above, or in Southern analysis. The human chromosome 7 content of the hybrid cell lines used were 1365 Rag 12-9: 7qter-p13; Rag GN6:7qter-pl 1.2; Ru Rag 4–13: 7cen-pter (Vortkamp et. al. (1991) *Genomics* 11:737–743). For Southern blot analysis, 5 $\mu$g of human DNA and 10 $\mu$gs of hybrid and mouse DNA digested with BglII were hybridized with a 375 bp fragment contained within the hIk-1 and hlk-2 primers.

Homologous recombination experiments in vitro and in vivo and knockout mice

To address the role of the lymphoid restricted transcription factor Ikaros in vivo we targeted mutations at the mouse Ikaros genomic locus in embryonic stem cells (E.S). Two targeting vectors carrying distinct deletions at the Ikaros genomic locus were transfected in the J1 E.S line derived from the SV129 mouse (En li, Cell 1992). Homologous recombination events in the E.S cells were scored by a double selection counter selection scheme; G418 and FIAU were used in the media to select for neomycin gene activity and for the absence of thymidine kinase gene activity. The neo gene is located in the middle of the construct while the tk gene is present at the 5' or 3' of the targeting vector and allows for selecting against non-homologous recombination events. E.S. cell lines carrying either mutation one or two were established by Southern analysis and were injected in the blastocysts of Balbe or C57 black mice. The chimeric blastocysts were reimplanted in pseudopregnant mice and gave rise to chimeric animals. Mice which were more than 70% chimeric for the SV129 strain as determined by coat color (agouti vs white or black background) were bred further. Germ line transmission was determined by coat color (agouti) and by Southern analysis of tail DNA. We are in the process of breeding these mice to obtain animals which are homozygous for these mutations.

Both of the targeted mutations are deletions. The first mutation deletes the last exon, E7, which is shared by al the Ikaros isoforms. This should generate proteins which can bind DNA but which cannot activate transcription. These proteins may function as dominant negative regulators of transcription since they can compete for DNA binding with wild type Ikaros proteins but cannot activate transcription. Mice heterozygous for this mutation may exhibit a decrease in the level of expression of genes that rely on the Ikaros proteins for their regulation. These mice may exhibit a less sever phenotype than the ones with total lack of expression of Ikaros proteins. Analysis of these animals may prove to be necessary if the phenotype on mice with total loss of function is severe.

The second mutation (a deletion of exon E3 and E4) should result in a total loss of function of the Ikaros gene. Mice homozygous for this mutation may have a severe impairment of the Ikaros gene. Mice homozygous for this mutation may have a severe impairment of their immune system as a result of altered expression of genes regulated by the Ikaros gene. Possible candidates for Ikaros regulation are TDT (recombination pathway) CD3 complex. TCR complex IL2 gene HIV LTR etc. Lymphoid cell lines derived from these mice can be used to delineate the regulatory pathway that leads to mature T and B cells but the mice themselves can be used to study the complex interaction between the different lineages in the hemopoietic pathway and design in vivo experiments to study and correct immunodeficiency syndromes. Finally, ES cell lines derived from these animals can be studied by in vivo differentiation into the hemopoietic/lymphopoietic lineage.

Use

The peptides of the invention m ay be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes or by transgenic modes.

Other Embodiments

Nucleic acid encoding all or part of the Ikaros gene can be used to transform cells. For example, the Ikaros gene, e.g., a mis-expressing or mutant form of the Ikaros gene, e.g., a deletion, or DNA encoding an Ikaros protein can be used to transform a cell and to produce a cell in which the cell's genomic Ikaros gene has been replaced by the transformed gene, producing, e.g., a cell deleted for the Ikaros gene. As described above, this approach can be used with cells capable of being grown in culture, e.g., cultured stem cells, to investigate the function of the Ikaros gene.

Analogously, nucleic acid encoding all or part of the Ikaros gene, e.g., a mis-expressing or mutant form of the gene, e.g., a deletion, can be used to transform a cell which subsequently gives rise to a transgenic animal. This approach can be used to create, e.g., a transgenic animal in which the Ikaros gene is, e.g., inactivated, e.g., by a deletion. Homozygous transgenic animals can be made by crosses between the offspring of a founder transgenic animal. Cell or tissue cultures can be derived from a transgenic animal. A subject at risk for a disorder characterized by an abnormality in T cell development or function, e.g., leukemia, can be detected by comparing the structure of the subject's Ikaros gene with the structure of a wild type Ikaros gene. Departure from the wild type structure by, e.g., frameshifts, critical point mutations, deletions, insertions, or translocations, are indicative of risk. The DNA sequence of the coding region of several exons as well as several intron exon boundaries are included herein. Other regions can be obtained or sequenced by methods known to those skilled in the art.

The invention includes any protein which is substantially homologous to an Ikaros protein, e.g., the Ikaros protein shown in SEQ ID NO:2, SEQ ID NO:3, or SEQ ID NO:5, or other isoforms. Also included are: allelic variations; natural mutants; induced mutants, e.g., in vitro deletions; proteins encoded by DNA that hybridizes under high or low (e.g., washing at 2×SSC at 40° C. with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference); and polypeptides or proteins specifically bound by antisera to an Ikaros protein, especially by antisera to the active site or binding domain of an Ikaros protein. The term also includes chimeric polypeptides that include an Ikaros protein.

DNA and peptide sequences of the invention can be, e.g., mouse, primate, e.g., human, or non-naturally occurring sequences.

The invention also includes any biologically active fragment or analog of an Ikaros protein. By "biologically active" is meant possessing any in vivo or in vitro activity which is characteristic of an Ikaros isoform, e.g., an isoform shown in (SEQ ID NO:2) or FIG. 3 (SEQ ID NO:3) or (SEQ ID NO:5), e.g., Ikaros activity as described above. Because the Ikaros proteins exhibit a range of physiological properties and because such properties may be attributable to different portions of the Ikaros protein molecule, a useful Ikaros protein fragment or Ikaros protein analog is one which exhibits a biological activity in any one (or more) of a variety of the Ikaros protein assays, for example, the ability to bind to or stimulate transcription from a δA element or an NKFB element, as described above. An Ikaros protein fragment or analog possesses, most preferably 90%, preferably 40%, or at least 10%, of the activity of a naturally occurring Ikaros isoform, e.g., of the Ikaros protein shown in (SEQ ID NO:2), (SEQ ID NO:3) or (SEQ ID NO:5), in any in vivo or in vitro Ikaros assay.

As described above, differential splicing of Ikaros transcripts generates at least five mRNAs that encode proteins with overlapping but distinct DNA binding specificity and affinity. The DNA binding specificity of the Ikaros proteins are apparently dictated primarily by the differential usage of exons encoding the N-terminal zinc fingers.

The present invention further pertains to recombinant Ikaros proteins which are encoded by genes derived from an animal and which have amino acid sequences evolutionarily related to an Ikaros protein represented by any of SEQ ID NOS: 2–8. Such recombinant Ikaros proteins preferably are capable of functioning in one of either role of an agonist of antagonist of at least one biological activity of a naturally-occurring Ikaros protein. The term "evolutionarily related to", with respect to either amino acid sequence or nucleic acid sequence, refers to Ikaros sequences which have arisen naturally, preferably in vertebrate organism, more preferably in mammals (e.g. humans, mice, pigs). The term also refers to nucleic acid sequences which, while derived from a naturally occurring Ikaros, have been altered by mutagenesis, as for example, combinatorial mutagenesis described below. Recombinant proteins evolutionarily related to the Ikaros proteins preferably at least 50% homologous, more preferably in the range of 60%–70% homologous and most preferably in the range of 80%–90% homologous with an amino acid sequence selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8. Polypeptides having a biological activity of a naturally-occurring Ikaros protein, or which can function antagonistically to naturally occurring Ikaros proteins, and having at least about 95%, more preferably at least about 98–99% homology with a sequence selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8 are also within the scope of the invention.

Isolated peptides having the activity of an Ikaros protein can be obtained by screening peptides recombinantly produced from the corresponding fragment of a nucleic acid selected from a group consisting of SEQ ID NO: 2, SEQ ID NO: 3, SEQ ID NO: 4, SEQ ID NO: 5, SEQ ID NO: 6, SEQ ID NO: 7 and SEQ ID NO: 8. In addition, fragments can be chemically synthesized using techniques known in the art such as conventional Merrifield solid phase f-Moc or t-Boc chemistry. For example, the subject Ikaros proteins may be arbitrarily divided into fragments of desired length with no overlap of the fragments, or preferably divided into overlapping fragments of a desired length. The fragments, whether produced recombinantly or by chemical synthesis, can be tested to identify those peptides having an Ikaros protein activity, such as by first measuring the ability of the fragment to bind to a particular DNA sequence as described above.

Moreover, it is possible to modify the structure of an Ikaros protein for such purposes as altering the biological activity, increasing solubility, improving bioavailability, enhancing therapeutic or prophylactic efficacy, or stability (e.g., shelf life ex vivo and resistance to proteolytic degradation in vivo). Such modified peptides are considered functional equivalents of peptides having an activity of an Ikaros protein as defined herein. A modified peptide can be produced in which the amino acid sequence has been altered, such as by amino acid substitution, deletion, or addition. In one embodiment, mutagenesis can give rise to Ikaros homologs which have intracellular half-lives dramatically different than the corresponding wild-type protein. For example, the altered protein can be rendered either more stable or less stable to proteolytic degradation or other cellular process which result in destruction of, or otherwise inactivation of, an Ikaros protein. Such Ikaros homologs, and the genes which encode them, can be utilized to alter the envelope of Ikaros expression by modulating the half-life of the protein. For instance, a short half-life can give rise to more transient Ikaros biological effects and, when part of an inducible expression system, can allow tighter control of Ikaros levels within the cell. Such modifications can also be used to generate Ikaros antagonists, which can be used, for example, to inhibit the biological consequences of wild-type Ikaros expression. Such Ikaros homologs can be especially useful to generate transgenic, and the antagonistic homologs can be especially useful where "knock-out" phenotypes are sought.

Thus, it will be apparent that variations of the Ikaros peptides and DNA molecules are also contemplated as being equivalent to those peptides and DNA molecules that are set forth in more detail above. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule, though such homologs can be screened for antagonistic activity as well. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methoinine. (see, for example, *Biochemistry,* 2nd ed, Ed. by L. Stryer, WH Freeman and Co.: 1981). Whether a change in the amino acid sequence of a peptide results in a functional Ikaros homolog can be readily determined by assessing the ability of the variant peptide to produce a response in cells in a fashion similar to the wild-type Ikaros. Likewise, the ability of an Ikaros homolog to function as an antagonist can be readily assessed from its ability to competitively inhibit the biological activity of a wild-type form of an Ikaros protein. Peptides in which more than one replacement has taken place can readily be tested in the same manner.

This invention further contemplates Ikaros homologs generated by a method used to create and screen sets of combinatorial mutants of Ikaros, as well as truncation mutants, and is especially useful for identifying potential variant sequences (e.g. homologs) that are functional in binding to a receptor for Ikaros. The purpose of screening such combinatorial libraries is to generate, for example, novel Ikaros homologs which can act as either agonists or antagonist, or alternatively, possess novel activities all together. To illustrate, Ikaros homologs can be engineered by the present method to provide more efficient binding to an Ikaros binding oligonucleotide which may be a part of an Ikaros-responsive element (IK-RE), yet still retain at least a portion of an activity associated with Ikaros. Alternatively, Ikaros homologs can be generated according to the present invention which retain the DNA binding ability of a naturally occurring Ikaros protein, but which competively inhibit the biological function of naturally occurring Ikaros proteins (e.g., is an antagonist).

In one aspect of this method, the amino acid sequences for a population of Ikaros homologs or other related proteins are aligned, preferably to promote the highest homology possible. Such a population of variants can include, for example, Ikaros homologs from one or more species, such as illustrated in FIG. 9 (alignment of human and mouse Ik-1 E3 through E7). Amino acids which appear at each position of the aligned sequences are selected to create a degenerate set of combinatorial sequences.

In a preferred embodiment, the combinatorial Ikaros library is produced by way of a degenerate library of genes encoding a library of polypeptides which each include at least a portion of potential Ikaros sequences. A mixture of synthetic oligonucleotides can be enzymatically ligated into gene sequences such that the degenerate set of potential Ikaros sequences are expressible as individual polypeptides, or alternatively, as a set of larger fusion proteins (e.g. for phage display) containing the set of Ikaros sequences therein.

As illustrated in FIG. 9, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (●), while insertional mutations in the variant relative to the reference sequence can be disregarded and left out of the sequence of the variant when aligned. For instance, FIG. 9 includes the alignment of several cloned forms of Ikaros from different species. Analysis of the alignment of the Ikaros clones shown in FIG. 9 can give rise to the generation of a degenerate library of polypeptides comprising potential Ikaros sequences, such as, to illustrate:

Xaa—Xaa—Ala—Ser—Asn—Val—Lys—Val—Glu—Thr—Gln—Ser—Asp—Glu—Glu—Asn—Gly—Arg—

Ala—Cys—Glu—Met—Asn—Gly—Glu—Glu—Cys—Ala—Glu—Asp—Leu—Arg—Met—Leu—Asp—Ala—

Ser—Gly—Glu—Lys—Met—Asn—Gly—Ser—His—Arg—Asp—Gln—Gly—Ser—Ser—Ala—Leu—Ser—

Gly—Val—Gly—Gly—Ile—Arg—Leu—Pro—Asn—Gly—Lys—Leu—Lys—Cys—Asp—Ile—Cys—Gly—

Ile—Xaa—Cys—Ile—Gly—Pro—Asn—Val—Leu—Met—Val—His—Lys—Arg—Ser—His—Thr—Gly—

Glu—Arg—Pro—Phe—Gln—Cys—Asn—Gln—Cys—Gly—Ala—Ser—Phe—Thr—Gln—Lys—Gly—Asn—

Leu—Leu—Arg—His—Ile—Lys—Leu—His—Ser—Gly—Glu—Lys—Pro—Phe—Lys—Cys—His—Leu—

Cys—Asn—Tyr—Ala—Cys—Arg—Arg—Arg—Asp—Ala—Leu—Thr—Gly—His—Leu—Arg—Thr—His—

Ser—Val—Gly—Lys—Pro—His—Lys—Cys—Gly—Tyr—Cys—Gly—Arg—Ser—Tyr—Lys—Gln—Arg—

Xaa—Ser—Leu—Glu—Glu—His—Lys—Glu—Arg—Cys—His—Asn—Tyr—Leu—Glu—Ser—Met—Gly—

Leu—Pro—Gly—Xaa—Xaa—Xaa—Pro—Val—Ile—Lys—Glu—Glu—Thr—Xaa—His—Xaa—Glu—Met—

Ala—Glu—Asp—Leu—Cys—Lys—Ile—Gly—Xaa—Glu—Arg—Ser—Leu—Val—Leu—Asp—Arg—Leu—

Ala—Ser—Asn—Val—Ala—Lys—Arg—Lys—Ser—Ser—Met—Pro—Gln—Lys—Phe—Leu—Gly—Asp—

Lys—Xaa—Leu—Ser—Asp—Xaa—Pro—Tyr—Asp—Ser—Ala—Xaa—Tyr—Glu—Lys—Glu—Xaa—Xaa—

Met—Met—Xaa—Ser—His—Val—Met—Asp—Xaa—Ala—Ile—Asn—Asn—Ala—Ile—Asn—Tyr—Leu—

-continued

Gly—Ala—Glu—Ser—Leu—Arg—Pro—Leu—Val—Gln—Thr—Pro—Pro—Gly—Xaa—Ser—Glu—Val—

Val—Pro—Val—Ile—Ser—Pro—Met—Tyr—Gln—Leu—His—Xaa—Xaa—Xaa—Ser—Xaa—Gly—Xaa—

Pro—Arg—Ser—Asn—His—Ser—Ala—Gln—Asp—Xaa—Ala—Val—Xaa—Xaa—Leu—Leu—Leu—Leu—

Ser—Lys—Ala—Lys—Xaa—Val—Xaa—Ser—Glu—Arg—Glu—Ala—Ser—Pro—Ser—Asn—Ser—Cys—

Gln—Asp—Ser—Thr—Asp—Thr—Glu—Ser—Asn—Xaa—Glu—Glu—Gln—Arg—Ser—Gly—Leu—Ile—

Tyr—Leu—Thr—Asn—His—Ile—Xaa—Xaa—Xaa—Ala—Xaa—Xaa—Xaa—Xaa—Xaa—Leu—Lys—Glu—

Glu—Xaa—Arg—Ala—Tyr—Xaa—Xaa—Leu—Arg—Ala—Ala—Ser—Glu—Asn—Ser—Gln—Asp—Ala—

Xaa—Arg—Val—Val—Ser—Thr—Ser—Gly—Glu—Gln—Xaa—Lys—Val—Tyr—Lys—Cys—Glu—His—

Cys—Arg—Val—Leu—Phe—Leu—Asp—His—Val—Met—Tyr—Thr—Ile—His—Met—Xaa—Xaa—Xaa—

Gly—Cys—His—Gly—Phe—Arg—Asp—Pro—Phe—Glu—Cys—Asn—Met—Cys—Gly—Tyr—His—Ser—

Gln—Asp—Arg—Tyr—Glu—Phe—Ser—Ser—His—Ile—Thr—Arg—Gly—Glu—His—Arg—Xaa—His—

Xaa—Ser— (SEQ ID NO:153)

Each of the degenerate positions Xaa can be generated to include just the amino acid residues which occur in either mIk-1 or hIk-1, or, alternatively, to include those amino acid plus others, e.g. all conservative mutations based on the actual sequences of mIk-1 and hIk-1, or completely random mutations, e.g. all 20 amino acids. For example, Xaa(3) (the third degenerate residue from the N-terminus) is either a valine or an isoleucine in the naturally occurring isoforms, but in a degenerate library derived by conserved mutations, Xaa(3) can represent Gly, Ala, Val, Ile, Leu, Ser or Thr. Likewise, in such a degenerate library, Xaa(5), which corresponds to a Thr in hlk-1 but which is not present in mIk-1, represents Gly, Ala, Val, Ile, Leu, Ser, Thr or an amino acid gap (e.g. not present). Furthermore, the degenerate library can be constructed such that the at least the codons for the last amino acid residue in each exon are degenerate to include a stop codon, such that the library also includes truncation mutations. For example, the codons for Thr-89, Ser-145, Pro-187, and Gly-232 (in SEQ ID NO:153) can be made degenerate to further provide stop codons (e.g. TAA) in some of the recombinant genes of the degenerate library.

In a preferred embodiment, the variegated library of Ikaros variants is generated by combinatorial mutagenesis at the nucleic acid level, and is encoded by a variegated gene library. There are many ways by which the library of potential Ikaros homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential Ikaros sequences. The synthesis of degenerate oligonucleotides is known in the art (see for example, Narang, S. A. (1983) *Tetrahedron* 39:3; Itakura et al. (1981) *Recombinant DNA, Proc 3rd Cleveland Sympos. Macromolecules,* ed. A. G. Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198,346, and 5,096,815).

In light of the present disclosue, other forms of mutagenesis generally applicable will be apparent to those skilled in the art in addition to the aforementioned rationale mutagenesis based on conserved versus non-conserved residues. For example, Ikaros homologs (both agonist and antagonist forms) can be generated and screened using, for example, alanine scanning mutagenesis and the like (Ruf et al. (1994) *Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of Ikaros homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Ikaros sequences created by combinatorial mutagenesis techniques.

In one embodiment, the candidate Ikaros gene products are displayed on the surface of a cell or viral particle, and the ability of particular cells or viral particles to bind an Ikaros-binding oligonucleotide (such as an Ik-BS described above) via this gene product is detected using an affinity selection metrices. For instance, the gene library can be cloned into the gene for a surface membrane protein of a bacterial cell, and the resulting fusion protein detected through bio-panning (Ladner et al., WO 88/06630; Fuchs et al. (1991) *Bio/Technology* 9:1370–1371; and Goward et al. (1992) *TIBS* 18:136–140). In a similar fashion, fluorescently labeled oligonucleotides which bind Ikaros can be used to search the library for useful Ikaros homologs. Cells can be visually inspected and separated under a fluorescence microscope, or, where the morphology of the cell permits, separated by a fluorescence-activated cell sorter.

In an alternate embodiment embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461).

In an illustrative embodiment, the recombinant phage antibody system (RPAS, Pharamacia Catalog number 27-9400-01) can be easily modified for use in expressing and screening Ikaros combinatorial libraries. For instance, the pCANTAB 5 phagemid of the RPAS kit contains the gene which encodes the phage gIII coat protein. The Ikaros combinatorial gene library can be cloned into the phagemid adjacent to the gIII signal sequence such that it will be expressed as a gIII fusion protein. After ligation, the phagemid is used to transform competent *E. coli* TGI cells. Transformed cells are subsequently infected with M13KO7 helper phage to rescue the phagemid and its candidate Ikaros gene insert. The resulting recombinant phage contain phagemid DNA encoding a specific candidate Ikaros, and display one or more copies of the corresponding fusion coat protein. The phage-displayed candidate Ikaros proteins which are capable of binding an Ik-RE are selected or enriched by bio-panning. For instance, as described by Rebar et al. (1994) *Science* 263:671–673, the phage library can be equilibrated with biotinylated target DNA and then applied to streptavidin-coated microtiter wells. After washing, the retained phage can be eluted, such as in high salt buffer, amplified in *E.coli,* and purified. Successive rounds of reinfection of *E. coli,* and panning will greatly enrich for Ikaros homologs, which can then be screened for further biological activities in order to differentiate agonists and antagonists.

In yet a further illustrative embodiment, the combinatorial Ikaros library can be recombinantly expressed in cultured cells, and the ability of members of the combinatorial library to act as one of either an agonist or antagonist of wild-type Ikaros proteins can be assessed through the use of selectable markers. Following such protocols as described in, for example, the Ladner et al. U.S. Pat. No. 5,198,346, the ability of members of the combinatorial librart to either promote or inhibit expression of a selectable marker can facilitate forced evolution of Ikaros homologs. For example, there are many genes that, when expressed, confer detectable phenotypes on cells. By placing Ikaros responsive elements (such as described above in the tkCAT constructs) proximate the selectable gene, the expression of the selectable marker can be brought under the control of an Ikaros protein able to bind that Ik-RE. As will be apparent, the level of expression of the gene, or lack thereof, will be indicative of the activity of the Ikaros homolog, i.e. whether it is an antagonist or agonist, and the assay can therefore be constructed to appropriately search for one or the other.

The selectable marker gene can be, to illustrate, a gene whose product confers drug resistance. In another embodiment, the selectable marker gene can encode a protein which, when expressed by the cell, inhibits cell growth (i.e., is cytotoxic or cytostatic). In still a further embodiment, the selectable marker can be a gene product which does not affect cell growth, but which is detectable by, for instance, immunoassay or photometric techniques. An exemplary embodiment of an immunoassay-detectable marker comprises a gene product encoding a cell surface antigen whose expression permits sorting of cells (and hence, of the combinatorial library) by immuno-affinity or FACS techniques. Likewise, an illustrative example of a photometric reporter gene is luciferase.

To score for those members of the combinatorial library which are Ikaros agonists, the reporter gene constructs can be transfected into the same cells, either eukaryotic (and which preferably lack an endogenously expressed Ikaros) or prokaryotic, as the combinatorial Ikaros library. To score for Ikaros antagonists, cells harboring the reporter gene construct and expressing a wild-type Ikaros protein can be used to detect inhibition of the expression of the reporter gene by an antagonist expressed from the combinatorial library. Because proliferation of a cell will generally be a more desirable mode of detecting a particular Ikaros activity (e.g. agonist or antagonist), as between the drug resistance marker and the cytotoxic/cytostatic factor, the former is favored when attempting to detect agonists and the latter favored to detect antagonists. Moveover, it will be appreciated that, in light of the foregoing description, it may be possible to isolate Ikaros homologs which are active in only a limited subset of the tissue in which Ikaros naturally occurs. For instance, by exploiting slight differences in DNA binding specificity between cell-types, an Ikaros antagonist can be derived which particularly inhibits the function of Ikaros in T cells, and can be used to selectively disrupt development of just that cell-type.

In a still further embodiment, the present invention contemplates the generation of Ikaros homologs by in vitro exon shuffling (de Vries et al. (1988) Biochemistry 27:2505–2572; and Langer-Safer et al. (1991) J. Biol Chem 266:3715–3723). As demonstrated above, each of the zinc finger domains can exert differing effects on binding specificity and transcriptional activation ability of the subject Ikaros proteins. Moreover, the naturally occurring ikaros proteins have arisen by alternate splicing mechanisms, and that given the exon arrangement of the Ikaros gene locus apparently displays a modular organization, it may be possible to "mix and match" exons to obtain proteins with novel DNA binding specificities and/or activities relative to naturally occurring forms of Ikaros. Such exon shuffling can be carried our in a rational fashion, in a semi-random fashion, or in a completely random fashion, the latter two being useful to generate screenable variegated libraries of potential Ikaros homologs. For example, each exon can be engineered to contain the same registration endonuclease site at each exon boundary. Admixing a variegated population of such Ikaros exons (e.g. 1/2, 3, 4, 5, 6, and 7 which were previously cleared to leave complementary "sticky ends", then allowing the exons to reanueal, will produce randomly recombined gene constructs. Selecting a portion of those constructs based on size (e.g. all genes less than 4250 base pairs) will allow the library to be reduced to a particular number of exons (e.g. 1 to about 7 to 10 exons ligated). Adding, as necessary, non-coding sequences and start and stop radons, the random library can be cloned into an expression vector and screened on described above.

Especially when synthesized in vitro, such as where peptide fragments, e.g. of lengths ranging from 10–20 residues, 50–70 residues, 100–120 residues, the amino acid residues at particular positions may further include analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptide can include an amino acid analog as for example, β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention. Such derivitives can be used for such purposes as altering the biological activity, increasing solubility, improving bioavailability, enhancing therapeutic or prophylactic efficacy, or stability (e.g., shelf life ex vivo and resistance to proteolytic degradation in vivo).

Other useful modifications include those which increase peptide stability; such analogs may contain, for example, one or more non-peptide bonds (which replace peptide bonds) or D-amino acids in the peptide sequence.

Analogs can differ from a naturally occurring Ikaros protein in amino acid sequence or can modified in ways that do not affect sequence, or both. Analogs of the invention will generally exhibit at least 70% more preferably 80%, more preferably 90%, and most preferably 95% or even, 99%, homology with a segment of 20 amino acid residues, preferably more than 40 amino acid residues or more preferably the entire sequence of naturally occurring Ikaros protein sequence.

As set forth above, alterations in primary sequence include genetic variations, both natural and induced. Also included are analogs that include residues other than naturally occurring L-amino acids, e.g., D-amino acids or non-naturally occurring or synthetic amino acids, e.g., β or γ amino acids. Alternatively, increased stability or solubility may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

In addition to substantially full-length polypeptides, the invention also includes biologically active fragments of the polypeptides. As used herein, the term "fragment", as applied to a polypeptide, will be of a length described for an Ikaros peptide above and will ordinarily be at least about 20 residues, more typically at least about 40 residues, preferably at least about 60 residues in length.

Fragments of Ikaros peptides or introns can be made by methods known to those skilled in the art, e.g., by expressing Ikaros DNA which has been manipulated in vitro to encode the desired fragment; e.g., by restriction digestion of an Ikaros DNA e.g., the sequence in SEQ ID NO:1 or SEQ ID NO:2. Analogs can be made by methods known to those skilled in the art, e.g., by in vitro DNA sequence modifications of the sequence of an Ikaros DNA e.g., the sequence in SEQ ID NO:1 or SEQ ID NO:2. For example, in vitro mutagenesis can be used to convert the DNA sequence of SEQ ID NO:1 into a sequence which encodes an analog in which one or more amino acid residues has undergone a replacement, e.g., a conservative replacement as described in the table of conservative amino acid substitutions provided herein. Fragments or analogs can be tested by methods known to those skilled in the art for the presence of Ikaros activity.

Also included are Ikaros protein polypeptides containing residues that are not required for biological activity of the peptide, such as residues that are not required for the biological activity of the polypeptide, or that result from alternative mRNA splicing or alternative protein processing events.

The invention also includes nucleic acids encoding the polypeptides of the invention.

In order to obtain an Ikaros protein one can insert Ikaros-encoding DNA into an expression vector, introduce the vector into a cell suitable for expression of the desired protein, and recover and purify the desired protein by prior art methods, Antibodies to Ikaros proteins can be made by immunizing an animal, e.g., a rabbit or mouse, and recovering anti-Ikaros antibodies by prior art methods.

To obtain a specific splicing-product (i.e., a specific isoform) one can make a synthetic structural gene including only the exons which code for the desired splicing product and express the gene as described above.

All of the above-cited references and publications are hereby incorporated by reference.

Other embodiments are within the following claims.

What is claimed is:

1. A purified peptide having at least 90% amino acid sequence identity with a peptide selected from the group consisting of: one or more of SEQ ID NO: 2–7, or 153; and wherein said peptide has one or more of the following properties: it stimulates transcription of a DNA sequence under the control any of a δA element, an NFKB element, or an Ikaros binding oligonucleotide consensus sequence; it binds to any of a δA element, an NFKB element, or an Ikaros binding oligonucleotide consensus sequence; it competitively inhibits the binding of a naturally occurring Ikaros isoform to any of a δA element, an NFKB element, or an Ikaros binding oligonucleotide consensus seqeuence; it competitively inhibits Ikaros binding to Ikaros responsive elements; or it inhibits protein-protein interactions of transcriptional complexes formed with naturally occurring Ikaros isoforms.

2. The purified peptide of claim 1, wherein said peptide has the property of: it stimulates transcription of a DNA sequence under the control any of a δA element, an NFKB element, or an Ikaros binding oligonucleotide consensus sequence.

3. The purified peptide of claim 1, wherein said peptide has the property of: it binds to any of a δA element, an NFKB element, or an Ikaros binding oligonucleotide consensus sequence.

4. The purified peptide of claim 1, wherein said peptide has the property of: it competitively inhibits the binding of a naturally occurring Ikaros isoform to any of a δA element, an NFKB element, or an Ikaros binding oligonucleotide consensus sequence.

5. The purified peptide of claim 1, wherein said peptide has the property of: it competitively inhibits Ikaros binding to Ikaros responsive elements.

6. The purified peptide of claim 1, wherein said peptide has the property of: it inhibits protein-protein interations of transcriptional complexes formed with naturally occurring Ikaros isoforms.

7. The purified peptide of claim 1, wherein said peptide is the peptide of SEQ ID NO: 2.

8. The purified peptide of claim 1, wherein said peptide is the peptide of SEQ ID NO: 3.

9. The purified peptide of claim 1, wherein said peptide is the peptide of SEQ ID NO: 4.

10. The purified peptide of claim 1, wherein said peptide is the peptide of SEQ ID NO: 5.

11. The purified peptide of claim 1, wherein said peptide is the peptide of SEQ ID NO: 6.

12. The purified peptide of claim 1, wherein said peptide is the peptide of SEQ ID NO: 7.

13. The purified peptide of claim 1, wherein said peptide is the peptide of SEQ ID NO: 153.

14. A purified peptide which includes an Ikaros peptide selected from the group consisting of:
- a sequence having at least 90% amino acid sequence identity with a polypeptide encoded by exon 7 of SEQ ID NO 166, 168 or 169;
- a sequence having at least 90% amino acid sequence identity with a polypeptide encoded by exon 6 of SEQ ID NO 171, 173 or 174;
- a sequence having at least 90% amino acid sequence identity with a polypeptide encoded by exon 5 of SEQ ID NO 176, 178 or 191;
- a sequence having at least 90% amino acid sequence identity with a polypeptide encoded by exon 4 of SEQ ID NO 180, 182 or 183;
- a sequence having at least 90% amino acid sequence identity with a polypeptide encoded by exon 3 of SEQ ID NO 185, 187 or 188; and
- a sequence having at least 90% amino acid sequence identity with a polypeptide encoded by exon 1/2 of SEQ ID NO 190; and wherein said peptide has one or more of the following properties: it stimulates transcription of a DNA sequence under the control any of a δA element, an NFKB element, or an Ikaros binding oligonucleotide consensus sequence; it binds to any of a δA element, an NFKB element, or an Ikaros binding oligonucleotide consensus sequence; it competitively inhibits the binding of a naturally occurring Ikaros isoform to any of a δA element, an NFKB element, or an Ikaros binding oligonucleotide consensus sequence; it competitively inhibits Ikaros binding to Ikaros responsive elements; or it inhibits protein-protein interations of transcriptional complexes formed with naturally occurring Ikaros isoforms.

15. The purified peptide of claim 14, wherein said peptide has the property of: it stimulates transcription of a DNA sequence under the control any of a δA element, an NFKB element, or an Ikaros binding oligonucleotide consensus sequence.

16. The purified peptide of claim 14, wherein said peptide has the property of: it binds to any of a δA element, an NFKB element, or an Ikaros binding oligonucleotide consensus sequence.

17. The purified peptide of claim 14, wherein said peptide has the property of: it competitively inhibits the binding of a naturally occurring Ikaros isoform to any of a δA element, an NFKB element, or an Ikaros binding oligonucleotide consensus sequence.

18. The purified peptide of claim 14, wherein said peptide has the property of: it competitively inhibits Ikaros binding to Ikaros responsive elements.

19. The purified peptide of claim 14, wherein said peptide has the property of: it inhibits protein-protein interations of transcriptional complexes formed with naturally occurring Ikaros isoforms.

20. The purified peptide of claim 14, in which the peptide includes an Ikaros peptide selected from the group consisting of:
- a sequence having at least 95% amino acid sequence identity with a polypeptide encoded by exon 7 of SEQ ID NO 166, 168 or 169;
- a sequence having at least 95% amino acid sequence identity with a polypeptide encoded by exon 6 of SEQ ID NO 171, 173 or 174;
- a sequence having at least 95% amino acid sequence identity with a polypeptide encoded by exon 5 of SEQ ID NO 176, 178 or 191;
- a sequence having at least 95% amino acid sequence identity with a polypeptide encoded by exon 4 of SEQ ID NO 180, 182 or 183;
- a sequence having at least 95% amino acid sequence identity with a polypeptide encoded by exon 3 of SEQ ID NO 185, 187 or 188; and
- a sequence having at least 95% amino acid sequence identity with a polypeptide encoded by exon 1/2 of SEQ ID NO 190.

21. The purified peptide of claim 14, in which the peptide includes an Ikaros peptide selected from the group consisting of:
- a sequence having at least 99% amino acid sequence identity with a polypeptide encoded by exon 7 of SEQ ID NO 166, 168 or 169;
- a sequence having at least 99% amino acid sequence identity with a polypeptide encoded by exon 6 of SEQ ID NO 171, 173 or 174;
- a sequence having at least 99% amino acid sequence identity with a polypeptide encoded by exon 5 of SEQ ID NO 176, 178 or 191;
- a sequence having at least 99% amino acid sequence identity with a polypeptide encoded by exon 4 of SEQ ID NO 180, 182 or 183;
- a sequence having at least 99% amino acid sequence identity with a polypeptide encoded by exon 3 of SEQ ID NO 185, 187 or 188; and
- a sequence having at least 99% amino acid sequence identity with a polypeptide encoded by exon 1/2 of SEQ ID NO 190.

22. The purified peptide of claim 21, wherein said peptide is the peptide of SEQ ID NO: 2.

23. The purified peptide of claim 21, wherein said peptide is the peptide of SEQ ID NO: 3.

24. The purified peptide of claim 21, wherein said peptide is the peptide of SEQ ID NO: 4.

25. The purified peptide of claim 21, wherein said peptide is the peptide of SEQ ID NO: 5.

26. The purified peptide of claim 21, wherein said peptide is the peptide of SEQ ID NO: 6.

27. The purified peptide of claim 21, wherein said peptide is the peptide of SEQ ID NO: 7.

28. The purified peptide of claim 21, wherein said peptide is the peptide of SEQ ID NO: 153.

29. A purified naturally occurring Ikaros isoform having at least 90% amino acid sequence identity with a peptide selected from the group consisting of: SEQ ID NO: 2 or 5; and wherein said peptide has one or more of the following properties: it stimulates transcription of a DNA sequence under the control any of a δA element, an NFKB element, or an Ikaros binding oligonucleotide consensus sequence; it binds to any of a δA element, an NFKB element, or an Ikaros binding oligonucleotide consensus sequence; it competitively inhibits the binding of a naturally occurring Ikaros isoform to any of a δA element, an NFKB element, or an Ikaros binding oligonucleotide consensus sequence; it competitively inhibits Ikaros binding to Ikaros responsive elements; or it inhibits protein-protein interations of transcriptional complexes formed with naturally occurring Ikaros isoforms.

30. The peptide of claim 29, wherein said peptide has the property of: it stimulates transcription of a DNA sequence under the control any of a δA element, an NFKB element, or an Ikaros binding oligonucleotide consensus sequence.

31. The peptide of claim 29, wherein said peptide has the property of: it binds to any of a δA element, an NFKB element, or an Ikaros binding oligonucleotide consensus sequence.

32. The peptide of claim 29, wherein said peptide has the property of: it competitively inhibits the binding of a naturally occurring Ikaros isoform to any of a δA element, an NFKB element, or an Ikaros binding oligonucleotide consensus sequence.

33. The peptide of claim 29, wherein said peptide has the property of: it competitively inhibits Ikaros binding to Ikaros responsive elements.

34. The peptide of claim 29, wherein said peptide has the property of: it inhibits protein-protein interations of transcriptional complexes formed with naturally occurring Ikaros isoforms.

35. A purified peptide sequence having at least 90% amino acid sequence identity with a peptide of one or more of SEQ ID NO: 2–7, and 153, and wherein said purified sequence lacks all or part of the sequence encoded by exon 7; and wherein said peptide has one or more of the following properties: it stimulates transcription of a DNA sequence under the control any of a δA element, an NFKB element, or an Ikaros binding oligonucleotide consensus sequence; it binds to any of a δA element, an NFKB element, or an Ikaros binding oligonucleotide consensus sequence; it competitively inhibits the binding of a naturally occurring Ikaros isoform to any of a δA element, an NFKB element, or an Ikaros binding oligonucleotide consensus sequence; it competitively inhibits Ikaros binding to Ikaros responsive elements; or it inhibits protein-protein interations of transcriptional complexes formed with naturally occurring Ikaros isoforms.

36. The purified peptide of claim 35, wherein said peptide has the property of: it stimulates transcription of a DNA sequence under the control any of a δA element, an NFKB element, or an Ikaros binding oligonucleotide consensus sequence.

37. The purified peptide of claim 35, wherein said peptide has the property of: it binds to any of a δA element, an NFKB element, or an Ikaros binding oligonucleotide consensus sequence.

38. The purified peptide of claim 35, wherein said peptide has the property of: it competitively inhibits the binding of a naturally occurring Ikaros isoform to any of a δA element, an NFKB element, or an Ikaros binding oligonucleotide consensus sequence.

39. The purified peptide of claim 35, wherein said peptide has the property of: it competitively inhibits Ikaros binding to Ikaros responsive elements.

40. The purified peptide of claim 35, wherein said peptide has the property of: it inhibits protein-protein interations of transcriptional complexes formed with naturally occurring Ikaros isoforms.

41. The purified peptide of claim 35, wherein said peptide is the peptide of SEQ ID NO: 2.

42. The purified peptide of claim 35, wherein said peptide is the peptide of SEQ ID NO: 3.

43. The purified peptide of claim 35, wherein said peptide is the peptide of SEQ ID NO: 4.

44. The purified peptide of claim 35, wherein said peptide is the peptide of SEQ ID NO: 5.

45. The purified peptide of claim 35, wherein said peptide is the peptide of SEQ ID NO: 6.

46. The purified peptide of claim 35, wherein said peptide is the peptide of SEQ ID NO: 7.

47. The purified peptide of claim 35, wherein said peptide is the peptide of SEQ ID NO: 153.

48. The purified peptide of claim 35, said purified peptide having 100% amino acid sequence identity with a peptide of one or more of SEQ ID NO: 2–7, or 153.

49. The purified peptide of claim 48, wherein said peptide is the peptide of SEQ ID NO: 2.

50. The purified peptide of claim 48, wherein said peptide is the peptide of SEQ ID NO: 3.

51. The purified peptide of claim 48, wherein said peptide is the peptide of SEQ ID NO: 4.

52. The purified peptide of claim 48, wherein said peptide is the peptide of SEQ ID NO: 5.

53. The purified peptide of claim 48, wherein said peptide is the peptide of SEQ ID NO: 6.

54. The purified peptide of claim 48, wherein said peptide is the peptide of SEQ ID NO: 7.

55. The purified peptide of claim 48, wherein said peptide is the peptide of SEQ ID NO: 153.

56. A purified peptide sequence having at least 90% amino acid sequence identity with a peptide selected from the group consisting of SEQ ID NO: 2–7, and 153, and wherein said purified sequence lacks all or part of the sequence encoded by exon 3 or 4; and wherein said peptide has one or more of the following properties: it stimulates transcription of a DNA sequence under the control any of a δA element, an NFKB element, or an Ikaros binding oligonucleotide consensus sequence; it binds to any of a δA element, an NFKB element, or an Ikaros binding oligonucleotide consensus sequence; it competitively inhibits the binding of a naturally occurring Ikaros isoform to any of a δA element, an NFKB element, or an Ikaros binding oligonucleotide consensus sequence; it competitively inhibits Ikaros binding to Ikaros responsive elements; or it inhibits protein-protein interations of transcriptional complexes formed with naturally occurring Ikaros isoforms.

57. The purified peptide of claim 56, wherein said peptide has the property of: it stimulates transcription of a DNA sequence under the control any of a δA element, an NFKB element, or an Ikaros binding oligonucleotide consensus sequence.

58. The purified peptide of claim 56, wherein said peptide has the property of: it binds to any of a δA element, an NFKB element, or an Ikaros binding oligonucleotide consensus sequence.

59. The purified peptide of claim 56, wherein said peptide has the property of: it competitively inhibits the binding of a naturally occurring Ikaros isoform to any of a δA element, an NFKB element, or an Ikaros binding oligonucleotide consensus sequence.

60. The purified peptide of claim 56, wherein said peptide has the property of: it competitively inhibits Ikaros binding to Ikaros responsive elements.

61. The purified peptide of claim 56, wherein said peptide has the property of: it inhibits protein-protein interations of transcriptional complexes formed with naturally occurring Ikaros isoforms.

62. The purified peptide of claim 56, wherein said peptide is the peptide of SEQ ID NO: 2.

63. The purified peptide of claim 56, wherein said peptide is the peptide of SEQ ID NO: 3.

64. The purified peptide of claim 56, wherein said peptide is the peptide of SEQ ID NO: 4.

65. The purified peptide of claim 56, wherein said peptide is the peptide of SEQ ID NO: 5.

66. The purified peptide of claim 56, wherein said peptide is the peptide of SEQ ID NO: 6.

67. The purified peptide of claim 56, wherein said peptide is the peptide of SEQ ID NO: 7.

68. The purified peptide of claim 56, wherein said peptide is the peptide of SEQ ID NO: 153.

69. The purified peptide of claim 56, said purified peptide having 100% amino acid sequence identity with a peptide of one or more of SEQ ID NO: 2–7, or 153.

70. The purified peptide of claim 69, wherein said peptide is the peptide of SEQ ID NO: 2.

71. The purified peptide of claim 69, wherein said peptide is the peptide of SEQ ID NO: 3.

72. The purified peptide of claim 69, wherein said peptide is the peptide of SEQ ID NO: 4.

73. The purified peptide of claim 69, wherein said peptide is the peptide of SEQ ID NO: 5.

74. The purified peptide of claim 69, wherein said peptide is the peptide of SEQ ID NO: 6.

75. The purified peptide of claim 69, wherein said peptide is the peptide of SEQ ID NO: 7.

76. The purified peptide of claim 69, wherein said peptide is the peptide of SEQ ID NO: 153.

77. A purified peptide having at least 99% amino acid sequence identity with a peptide selected from the group consisting of: one or more of SEQ ID NO: 2–7, or 153.

78. The purified peptide of claim 77, wherein said peptide is the peptide of SEQ ID NO: 2.

79. The purified peptide of claim 77, wherein said peptide is the peptide of SEQ ID NO: 3.

80. The purified peptide of claim 77, wherein said peptide is the peptide of SEQ ID NO: 4.

81. The purified peptide of claim 77, wherein said peptide is the peptide of SEQ ID NO: 5.

82. The purified peptide of claim 77, wherein said peptide is the peptide of SEQ ID NO: 6.

83. The purified peptide of claim 77, wherein said peptide is the peptide of SEQ ID NO: 7.

84. The purified peptide of claim 77, wherein said peptide is the peptide of SEQ ID NO: 153.

85. The purified peptide having 100% amino acid sequence identity with a peptide selected from the group consisting of: one or more of SEQ ID NO: 2–7, or 153.

86. The purified peptide of claim 85, wherein said peptide is the peptide of SEQ ID NO: 2.

87. The purified peptide of claim 85, wherein said peptide is the peptide of SEQ ID NO: 3.

88. The purified peptide of claim 85, wherein said peptide is the peptide of SEQ ID NO: 4.

89. The purified peptide of claim 85, wherein said peptide is the peptide of SEQ ID NO: 5.

90. The purified peptide of claim 85, wherein said peptide is the peptide of SEQ ID NO: 6.

91. The purified peptide of claim 85, wherein said peptide is the peptide of SEQ ID NO: 7.

92. The purified peptide of claim 85, wherein said peptide is the peptide of SEQ ID NO: 153.

93. The purified peptide encoded by a nucleic acid sequence which hybridizes under high stringency conditions to a nucleic acid sequence which encodes a peptide selected from the group consisting of: one or more of SEQ ID NO: 2–7, or 153.

94. The purified peptide of claim 93, wherein said peptide is the peptide of SEQ ID NO: 2.

95. The purified peptide of claim 93, wherein said peptide is the peptide of SEQ ID NO: 3.

96. The purified peptide of claim 93, wherein said peptide is the peptide of SEQ ID NO: 4.

97. The purified peptide of claim 93, wherein said peptide is the peptide of SEQ ID NO: 5.

98. The purified peptide of claim 93, wherein said peptide is the peptide of SEQ ID NO: 6.

99. The purified peptide of claim 93, wherein said peptide is the peptide of SEQ ID NO: 7.

100. The purified peptide of claim 93, wherein said peptide is the peptide of SEQ ID NO: 153.

101. The purified peptide which includes an Ikaros exon selected from the group consisting of:

a sequence having at least 99% amino acid sequence identity with a polypeptide encoded by exon 7 of SEQ ID NO 166, 168 or 169;

a sequence having at least 99% amino acid sequence identity with a polypeptide encoded by exon 6 of SEQ ID NO 171, 173 or 174;

a sequence having at least 99% amino acid sequence identity with a polypeptide encoded by exon 5 of SEQ ID NO 176, 178 or 191;

a sequence having at least 99% amino acid sequence identity with a polypeptide encoded by exon 4 of SEQ ID NO 180, 182 or 183;

a sequence having at least 99% amino acid sequence identity with a polypeptide encoded by exon 3 of SEQ ID NO 185, 187 or 188; and a sequence having at least 99% amino acid sequence identity with a polypeptide encoded by exon 1/2 of SEQ ID NO 190.

102. The purified peptide of claim 101, wherein said peptide includes a sequence having at least 99% amino acid sequence identity with a polypeptide encoded by exon 7 of SEQ ID NO 166, 168, or 169.

103. The purified peptide of claim 101, wherein said peptide includes a sequence having at least 99% amino acid sequence identity with a polypeptide encoded by exon 6 of SEQ ID NO 171, 173, or 174.

104. The purified peptide of claim 101, wherein said peptide includes a sequence having at least 99% amino acid sequence identity with a polypeptide encoded by exon 5 of SEQ ID NO 176, 178, or 191.

105. The purified peptide of claim 101, wherein said peptide includes a sequence having at least 99% amino acid sequence identity with a polypeptide encoded by exon 4 of SEQ ID NO 180, 182, or 183.

106. The purified peptide of claim 101, wherein said peptide includes a sequence having at least 99% amino acid sequence identity with a polypeptide encoded by exon 3 of SEQ ID NO 185, 187, or 188.

107. The purified peptide of claim 101, wherein said peptide includes a sequence having at least 99% amino acid sequence identity with a polypeptide encoded by exon 1/2 of SEQ ID NO 190.

108. A purified peptide which includes an Ikaros peptide selected from the group consisting of:

a sequence having at least 100% amino acid sequence identity with a polypeptide encoded by exon 7 of SEQ ID NO 166, 168 or 169;

a sequence having at least 100% amino acid sequence identity with a polypeptide encoded by exon 6 of SEQ ID NO 171, 173 or 174;

a sequence having at least 100% amino acid sequence identity with a polypeptide encoded by exon 5 of SEQ ID NO 176, 178 or 191;

a sequence having at least 100% amino acid sequence identity with a polypeptide encoded by exon 4 of SEQ ID NO 180, 182 or 183;

a sequence having at least 100% amino acid sequence identity with a polypeptide encoded by exon 3 of SEQ ID NO 185, 187 or 188; and a sequence having at least 100% amino acid sequence identity with a polypeptide encoded by exon 1/2 of SEQ ID NO 190.

109. The purified peptide of claim 108, wherein said peptide includes a sequence having 100% amino acid sequence identity with a polypeptide encoded by exon 7 of SEQ ID NO 166, 168 or 169.

110. The purified peptide of claim 108, wherein said peptide includes a sequence having 100% amino acid sequence identity with a polypeptide encoded by exon 6 of SEQ ID NO 171, 173 or 174.

111. The purified peptide of claim 108, wherein said peptide includes a sequence having 100% amino acid sequence identity with a polypeptide encoded by exon 5 of SEQ ID NO 176, 178 or 191.

112. The purified peptide of claim 108, wherein said peptide includes a sequence having 100% amino acid sequence identity with a polypeptide encoded by exon 4 of SEQ ID NO 180, 182 or 183.

113. The purified peptide of claim 108, wherein said peptide includes a sequence having 100% amino acid sequence identity with a polypeptide encoded by exon 3 of SEQ ID NO 185, 187 or 188.

114. The purified peptide of claim 108, wherein said peptide includes a sequence having 100% amino acid sequence identity with a polypeptide encoded by exon 1/2 of SEQ ID NO 190.

* * * * *

SEQUENCE LISTING ( 1 ) GENERAL INFORMATION:

( i i i ) NUMBER OF SEQUENCES: 191

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
AGAAGTTTCC ATGACATCAT GAATGGGGGT GGCAGAGA                          38
```

( 2 ) INFORMATION FOR SEQ ID NO:2:

( i ) SEQUENCE CHARACTERISTICS:
        ( A ) LENGTH: 1788 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 223..1515

( x i ) SEQUENCE DESCRIPTION: SEQ ID NO:2:

```
AATTCGTTCT ACCTTCTCTG AACCCCAGTG GTGTGTCAAG GCCGGACTGG GAGCTTGGGG     60

GAAGAGGAAG AGGAAGAGGA ATCTGCGGCT CATCCAGGGA TCAGGGTCCT TCCCAAGTGG    120

CCACTCAGAG GGGACTCAGA GCAAGTCTAG ATTTGTGTGG CAGAGAGAGA CAGCTCTCGT    180

TTGGCCTTGG GGAGGCACAA GTCTGTTGAT AACCTGAAGA CA                      222

ATG GAT GTC GAT GAG GGT CAA GAC ATG TCC CAA GTT TCA GGA AAG GAG     270
Met Asp Val Asp Glu Gly Gln Asp Met Ser Gln Val Ser Gly Lys Glu
 1               5                  10                  15

AGC CCC CCA GTC AGT GAC ACT CCA GAT GAA GGG GAT GAG CCC ATG CCT     318
Ser Pro Pro Val Ser Asp Thr Pro Asp Glu Gly Asp Glu Pro Met Pro
             20                  25                  30

GTC CCT GAG GAC CTG TCC ACT ACC TCT GGA GCA CAG CAG AAC TCC AAG     366
Val Pro Glu Asp Leu Ser Thr Thr Ser Gly Ala Gln Gln Asn Ser Lys
         35                  40                  45

AGT GAT CGA GGC ATG GGT GAA CGG CCT TTC CAG TGC AAC CAG TCT GGG     414
Ser Asp Arg Gly Met Gly Glu Arg Pro Phe Gln Cys Asn Gln Ser Gly
     50                  55                  60

GCC TCC TTT ACC CAG AAA GGC AAC CTC CTG CGG CAC ATC AAG CTG CAC     462
Ala Ser Phe Thr Gln Lys Gly Asn Leu Leu Arg His Ile Lys Leu His
 65                  70                  75                  80

TCG GGT GAG AAG CCC TTC AAA TGC CAT CTT TGC AAC TAT GCC TGC CGC     510
Ser Gly Glu Lys Pro Phe Lys Cys His Leu Cys Asn Tyr Ala Cys Arg
                 85                  90                  95

CGG AGG GAC GCC CTC ACC GGC CAC CTG AGG ACG CAC TCC GTT GGT AAG     558
Arg Arg Asp Ala Leu Thr Gly His Leu Arg Thr His Ser Val Gly Lys
            100                 105                 110

CCT CAC AAA TGT GGA TAT TGT GGC CGG AGC TAT AAA CAG CGA AGC TCT     606
Pro His Lys Cys Gly Tyr Cys Gly Arg Ser Tyr Lys Gln Arg Ser Ser
        115                 120                 125

TTA GAG GAG CAT AAA GAG CGA TGC CAC AAC TAC TTG GAA AGC ATG GGC     654
```

-continued

| | | | | | | | | | | | | | | |
|---|---|---|---|---|---|---|---|---|---|---|---|---|---|---|
| Leu | Glu | Glu | His | Lys | Glu | Arg | Cys | His | Asn | Tyr | Leu | Glu | Ser | Met | Gly |
| | 130 | | | | 135 | | | | | 140 | | | | |

| CTT | CCG | GGC | GTG | TGC | CCA | GTC | ATT | AAG | GAA | GAA | ACT | AAC | CAC | AAC | GAG | 702 |
| Leu | Pro | Gly | Val | Cys | Pro | Val | Ile | Lys | Glu | Glu | Thr | Asn | His | Asn | Glu |
| 145 | | | | 150 | | | | | 155 | | | | | 160 |

| ATG | GCA | GAA | GAC | CTG | TGC | AAG | ATA | GGA | GCA | GAG | AGG | TCC | CTT | GTC | CTG | 750 |
| Met | Ala | Glu | Asp | Leu | Cys | Lys | Ile | Gly | Ala | Glu | Arg | Ser | Leu | Val | Leu |
| | | | | 165 | | | | | 170 | | | | | 175 |

| GAC | AGG | CTG | GCA | AGC | AAT | GTC | GCC | AAA | CGT | AAG | AGC | TCT | ATG | CCT | CAG | 798 |
| Asp | Arg | Leu | Ala | Ser | Asn | Val | Ala | Lys | Arg | Lys | Ser | Ser | Met | Pro | Gln |
| | | | 180 | | | | | 185 | | | | | 190 | |

| AAA | TTT | CTT | GGA | GAC | AAG | TGC | CTG | TCA | GAC | ATG | CCC | TAT | GAC | AGT | GCC | 846 |
| Lys | Phe | Leu | Gly | Asp | Lys | Cys | Leu | Ser | Asp | Met | Pro | Tyr | Asp | Ser | Ala |
| | | | 195 | | | | 200 | | | | | 205 | | |

| AAC | TAT | GAG | AAG | GAG | GAT | ATG | ATG | ACA | TCC | CAC | GTG | ATG | GAC | CAG | GCC | 894 |
| Asn | Tyr | Glu | Lys | Glu | Asp | Met | Met | Thr | Ser | His | Val | Met | Asp | Gln | Ala |
| | 210 | | | | | 215 | | | | | 220 | | | | |

| ATC | AAC | AAT | GCC | ATC | AAC | TAC | CTG | GGG | GCT | GAG | TCC | CTG | CGC | CCA | TTG | 942 |
| Ile | Asn | Asn | Ala | Ile | Asn | Tyr | Leu | Gly | Ala | Glu | Ser | Leu | Arg | Pro | Leu |
| 225 | | | | | 230 | | | | | 235 | | | | | 240 |

| GTG | CAG | ACA | CCC | CCC | GGT | AGC | TCC | GAG | GTG | GTG | CCA | GTC | ATC | AGC | TCC | 990 |
| Val | Gln | Thr | Pro | Pro | Gly | Ser | Ser | Glu | Val | Val | Pro | Val | Ile | Ser | Ser |
| | | | | 245 | | | | | 250 | | | | | 255 | |

| ATG | TAC | CAG | CTG | CAC | AAG | CCC | CCC | TCA | GAT | GGC | CCC | CCA | CGG | TCC | AAC | 1038 |
| Met | Tyr | Gln | Leu | His | Lys | Pro | Pro | Ser | Asp | Gly | Pro | Pro | Arg | Ser | Asn |
| | | | 260 | | | | | 265 | | | | | 270 | | |

| CAT | TCA | GCA | CAG | GAC | GCC | GTG | GAT | AAC | TTG | CTG | CTG | CTG | TCC | AAG | GCC | 1086 |
| His | Ser | Ala | Gln | Asp | Ala | Val | Asp | Asn | Leu | Leu | Leu | Leu | Ser | Lys | Ala |
| | | 275 | | | | | 280 | | | | | 285 | | | |

| AAG | TCT | GTG | TCA | TCG | GAG | CGA | GAG | GCC | TCC | CCG | AGC | AAC | AGC | TGC | CAA | 1134 |
| Lys | Ser | Val | Ser | Ser | Glu | Arg | Glu | Ala | Ser | Pro | Ser | Asn | Ser | Cys | Gln |
| 290 | | | | | 295 | | | | | 300 | | | | | |

| GAC | TCC | ACA | GAT | ACA | GAG | AGC | AAC | GCG | GAG | GAA | CAG | CGC | AGC | GGC | CTT | 1182 |
| Asp | Ser | Thr | Asp | Thr | Glu | Ser | Asn | Ala | Glu | Glu | Gln | Arg | Ser | Gly | Leu |
| 305 | | | | | 310 | | | | | 315 | | | | | 320 |

| ATC | TAC | CTA | ACC | AAC | CAC | ATC | AAC | CCG | CAT | GCA | CGC | AAT | GGG | CTG | GCT | 1230 |
| Ile | Tyr | Leu | Thr | Asn | His | Ile | Asn | Pro | His | Ala | Arg | Asn | Gly | Leu | Ala |
| | | | | 325 | | | | | 330 | | | | | 335 | |

| CTC | AAG | GAG | GAG | CAG | CGC | GCC | TAC | GAG | GTG | CTG | AGG | GCG | GCC | TCA | GAG | 1278 |
| Leu | Lys | Glu | Glu | Gln | Arg | Ala | Tyr | Glu | Val | Leu | Arg | Ala | Ala | Ser | Glu |
| | | | 340 | | | | | 345 | | | | | 350 | | |

| AAC | TCG | CAG | GAT | GCC | TTC | CGT | GTG | GTC | AGC | ACG | AGT | GGC | GAG | CAG | CTG | 1326 |
| Asn | Ser | Gln | Asp | Ala | Phe | Arg | Val | Val | Ser | Thr | Ser | Gly | Glu | Gln | Leu |
| | | 355 | | | | | 360 | | | | | 365 | | | |

| AAG | GTG | TAC | AAG | TGC | GAA | CAC | TGC | CGC | GTG | CTC | TTC | CTG | GAT | CAC | GTC | 1374 |
| Lys | Val | Tyr | Lys | Cys | Glu | His | Cys | Arg | Val | Leu | Phe | Leu | Asp | His | Val |
| | 370 | | | | | 375 | | | | | 380 | | | | |

| ATG | TAT | ACC | ATT | CAC | ATG | GGC | TGC | CAT | GGC | TGC | CAT | GGC | TTT | CGG | GAT | 1422 |
| Met | Tyr | Thr | Ile | His | Met | Gly | Cys | His | Gly | Cys | His | Gly | Phe | Arg | Asp |
| 385 | | | | | 390 | | | | | 395 | | | | | 400 |

| CCC | TTT | GAG | TGT | AAC | ATG | TGT | GGT | TAT | CAC | AGC | CAG | GAC | AGG | TAC | GAG | 1470 |
| Pro | Phe | Glu | Cys | Asn | Met | Cys | Gly | Tyr | His | Ser | Gln | Asp | Arg | Tyr | Glu |
| | | | | 405 | | | | | 410 | | | | | 415 | |

| TTC | TCA | TCC | CAT | ATC | ACG | CGG | GGG | GAG | CAT | CGT | TAC | CAC | CTG | AGC | | 1515 |
| Phe | Ser | Ser | His | Ile | Thr | Arg | Gly | Glu | His | Arg | Tyr | His | Leu | Ser | |
| | | | 420 | | | | | 425 | | | | | 430 | | |

TAAACCCAGC CAGGCCCCAC TGAAGCACAA AGATAGCTGG TTATGCCTCC TTCCCGGCAG    1575

CTGGACCCAC AGCGGACAAT GTGGGAGTGG ATTTGCAGGC AGCATTTGTT CTTTTATGTT    1635

GGTTGTTTGG CGTTTCATTT GCGTTGGAAG ATAAGTTTTT AATGTTAGTG ACAGGATTGC    1695

```
ATTGCATCAG CAACATTCAC AACATCCATC CTTCTAGCCA GTTTTGTTCA CTGGTAGCTG    1755

AGGTTTCCCG GATATGTGGC TTCCTAACAC TCT                                 1788
```

( 2 ) INFORMATION FOR SEQ ID NO:3:

( i ) SEQUENCE CHARACTERISTICS:
        ( A ) LENGTH: 1386 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1386

( x i ) SEQUENCE DESCRIPTION: SEQ ID NO:3:

```
AAT  GTT  AAA  GTA  GAG  ACT  CAG  AGT  GAT  GAA  GAG  AAT  GGG  CGT  GCC  TGT     48
Asn  Val  Lys  Val  Glu  Thr  Gln  Ser  Asp  Glu  Glu  Asn  Gly  Arg  Ala  Cys
 1                  5                       10                       15

GAA  ATG  AAT  GGG  GAA  GAA  TGT  GCG  GAG  GAT  TTA  CGA  ATG  CTT  GAT  GCC     96
Glu  Met  Asn  Gly  Glu  Glu  Cys  Ala  Glu  Asp  Leu  Arg  Met  Leu  Asp  Ala
                    20                       25                       30

TCG  GGA  GAG  AAA  ATG  AAT  GGC  TCC  CAC  AGG  GAC  CAA  GGC  AGC  TCG  GCT    144
Ser  Gly  Glu  Lys  Met  Asn  Gly  Ser  His  Arg  Asp  Gln  Gly  Ser  Ser  Ala
               35                       40                       45

TTG  TCG  GGA  GTT  GGA  GGC  ATT  CGA  CTT  CCT  AAC  GGA  AAA  CTA  AAG  TGT    192
Leu  Ser  Gly  Val  Gly  Gly  Ile  Arg  Leu  Pro  Asn  Gly  Lys  Leu  Lys  Cys
     50                       55                       60

GAT  ATC  TGT  GGG  ATC  ATT  TGC  ATC  GGG  CCC  AAT  GTG  CTC  ATG  GTT  CAC    240
Asp  Ile  Cys  Gly  Ile  Ile  Cys  Ile  Gly  Pro  Asn  Val  Leu  Met  Val  His
65                        70                       75                       80

AAA  AGA  AGC  CAC  ACT  GGA  GAA  CGG  CCC  TTC  CAG  TGC  AAT  CAG  TGC  GGG    288
Lys  Arg  Ser  His  Thr  Gly  Glu  Arg  Pro  Phe  Gln  Cys  Asn  Gln  Cys  Gly
                         85                       90                       95

GCC  TCA  TTC  ACC  CAG  AAG  GGC  AAC  CTG  CTC  CGG  CAC  ATC  AAG  CTG  CAT    336
Ala  Ser  Phe  Thr  Gln  Lys  Gly  Asn  Leu  Leu  Arg  His  Ile  Lys  Leu  His
                    100                      105                      110

TCC  GGG  GAG  AAG  CCC  TTC  AAA  TGC  CAC  CTC  TGC  AAC  TAC  GCC  TGC  CGC    384
Ser  Gly  Glu  Lys  Pro  Phe  Lys  Cys  His  Leu  Cys  Asn  Tyr  Ala  Cys  Arg
               115                      120                      125

CGG  AGG  GAC  GCC  CTC  ACT  GGC  CAC  CTG  AGG  ACG  CAC  TCC  GTT  GGT  AAA    432
Arg  Arg  Asp  Ala  Leu  Thr  Gly  His  Leu  Arg  Thr  His  Ser  Val  Gly  Lys
     130                      135                      140

CCT  CAC  AAA  TGT  GGA  TAT  TGT  GGC  CGA  AGC  TAT  AAA  CAG  CGA  ACG  TCT    480
Pro  His  Lys  Cys  Gly  Tyr  Cys  Gly  Arg  Ser  Tyr  Lys  Gln  Arg  Thr  Ser
145                      150                      155                      160

TTA  GAG  GAA  CAT  AAA  GAG  CGC  TGC  CAC  AAC  TAC  TTG  GAA  AGC  ATG  GGC    528
Leu  Glu  Glu  His  Lys  Glu  Arg  Cys  His  Asn  Tyr  Leu  Glu  Ser  Met  Gly
                    165                      170                      175

CTT  CCG  GGC  ACA  CTG  TAC  CCA  GTC  ATT  AAA  GAA  GAA  ACT  AAG  CAC  AGT    576
Leu  Pro  Gly  Thr  Leu  Tyr  Pro  Val  Ile  Lys  Glu  Glu  Thr  Lys  His  Ser
               180                      185                      190

GAA  ATG  GCA  GAA  GAC  CTG  TGC  AAG  ATA  GGA  TCA  GAG  AGA  TCT  CTC  GTG    624
Glu  Met  Ala  Glu  Asp  Leu  Cys  Lys  Ile  Gly  Ser  Glu  Arg  Ser  Leu  Val
          195                      200                      205

CTG  GAC  AGA  CTA  GCA  AGT  AAT  GTC  GCC  AAA  CGT  AAG  AGC  TCT  ATG  CCT    672
Leu  Asp  Arg  Leu  Ala  Ser  Asn  Val  Ala  Lys  Arg  Lys  Ser  Ser  Met  Pro
     210                      215                      220

CAG  AAA  TTT  CTT  GGG  GAC  AAG  GGC  CTG  TCC  GAC  ACG  CCC  TAC  GAC  AGT    720
Gln  Lys  Phe  Leu  Gly  Asp  Lys  Gly  Leu  Ser  Asp  Thr  Pro  Tyr  Asp  Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 225 |     |     |     |     | 230 |     |     |     |     | 235 |     |     |     |     | 240 |      |
| GCC | ACG | TAC | GAG | AAG | GAG | AAC | GAA | ATG | ATG | AAG | TCC | CAC | GTG | ATG | GAC | 768  |
| Ala | Thr | Tyr | Glu | Lys | Glu | Asn | Glu | Met | Met | Lys | Ser | His | Val | Met | Asp |      |
|     |     |     |     | 245 |     |     |     |     | 250 |     |     |     |     | 255 |     |      |
| CAA | GCC | ATC | AAC | AAC | GCC | ATC | AAC | TAC | CTG | GGG | GCC | GAG | TCC | CTG | CGC | 816  |
| Gln | Ala | Ile | Asn | Asn | Ala | Ile | Asn | Tyr | Leu | Gly | Ala | Glu | Ser | Leu | Arg |      |
|     |     |     | 260 |     |     |     |     | 265 |     |     |     |     | 270 |     |     |      |
| CCG | CTG | GTG | CAG | ACG | CCC | CCG | GGT | GGT | TCC | GAG | GTG | GTC | CCG | GTC | ATC | 864  |
| Pro | Leu | Val | Gln | Thr | Pro | Pro | Gly | Gly | Ser | Glu | Val | Val | Pro | Val | Ile |      |
|     |     | 275 |     |     |     |     | 280 |     |     |     |     | 285 |     |     |     |      |
| AGC | CCG | ATG | TAC | CAG | CTG | CAC | AGG | CGC | TCG | GAG | GGC | ACC | CCG | CGC | TCC | 912  |
| Ser | Pro | Met | Tyr | Gln | Leu | His | Arg | Arg | Ser | Glu | Gly | Thr | Pro | Arg | Ser |      |
|     | 290 |     |     |     |     | 295 |     |     |     |     | 300 |     |     |     |     |      |
| AAC | CAC | TCG | GCC | CAG | GAC | AGC | GCC | GTG | GAG | TAC | CTG | CTG | CTG | CTC | TCC | 960  |
| Asn | His | Ser | Ala | Gln | Asp | Ser | Ala | Val | Glu | Tyr | Leu | Leu | Leu | Leu | Ser |      |
| 305 |     |     |     |     | 310 |     |     |     |     | 315 |     |     |     |     | 320 |      |
| AAG | GCC | AAG | TTG | GTG | CCC | TCG | GAG | CGC | GAG | GCG | TCC | CCG | AGC | AAC | AGC | 1008 |
| Lys | Ala | Lys | Leu | Val | Pro | Ser | Glu | Arg | Glu | Ala | Ser | Pro | Ser | Asn | Ser |      |
|     |     |     |     | 325 |     |     |     |     | 330 |     |     |     |     | 335 |     |      |
| TGC | CAA | GAC | TCC | ACG | GAC | ACC | GAG | AGC | AAC | AAC | GAG | GAG | CAG | CGC | AGC | 1056 |
| Cys | Gln | Asp | Ser | Thr | Asp | Thr | Glu | Ser | Asn | Asn | Glu | Glu | Gln | Arg | Ser |      |
|     |     |     | 340 |     |     |     |     | 345 |     |     |     |     | 350 |     |     |      |
| GGT | CTT | ATC | TAC | CTG | ACC | AAC | CAC | ATC | GCC | CGA | CGC | GCG | CAA | CGC | GTG | 1104 |
| Gly | Leu | Ile | Tyr | Leu | Thr | Asn | His | Ile | Ala | Arg | Arg | Ala | Gln | Arg | Val |      |
|     |     | 355 |     |     |     |     | 360 |     |     |     |     | 365 |     |     |     |      |
| TCG | CTC | AAG | GAG | GAG | CAC | CGC | GCC | TAC | GAC | CTG | CTG | CGC | GCC | GCC | TCC | 1152 |
| Ser | Leu | Lys | Glu | Glu | His | Arg | Ala | Tyr | Asp | Leu | Leu | Arg | Ala | Ala | Ser |      |
|     | 370 |     |     |     |     | 375 |     |     |     |     | 380 |     |     |     |     |      |
| GAG | AAC | TCG | CAG | GAC | GCG | CTC | CGC | GTG | GTC | AGC | ACC | AGC | GGG | GAG | CAG | 1200 |
| Glu | Asn | Ser | Gln | Asp | Ala | Leu | Arg | Val | Val | Ser | Thr | Ser | Gly | Glu | Gln |      |
| 385 |     |     |     |     | 390 |     |     |     |     | 395 |     |     |     |     | 400 |      |
| ATG | AAG | GTG | TAC | AAG | TGC | GAA | CAC | TGC | CGG | GTG | CTC | TTC | CTG | GAT | CAC | 1248 |
| Met | Lys | Val | Tyr | Lys | Cys | Glu | His | Cys | Arg | Val | Leu | Phe | Leu | Asp | His |      |
|     |     |     |     | 405 |     |     |     |     | 410 |     |     |     |     | 415 |     |      |
| GTC | ATG | TAC | ACC | ATC | CAC | ATG | GGC | TGC | CAC | GGC | TTC | CGT | GAT | CCT | TTT | 1296 |
| Val | Met | Tyr | Thr | Ile | His | Met | Gly | Cys | His | Gly | Phe | Arg | Asp | Pro | Phe |      |
|     |     |     | 420 |     |     |     |     | 425 |     |     |     |     | 430 |     |     |      |
| GAG | TGC | AAC | ATG | TGC | GGC | TAC | CAC | AGC | CAG | GAC | CGG | TAC | GAG | TTC | TCG | 1344 |
| Glu | Cys | Asn | Met | Cys | Gly | Tyr | His | Ser | Gln | Asp | Arg | Tyr | Glu | Phe | Ser |      |
|     |     | 435 |     |     |     |     | 440 |     |     |     |     | 445 |     |     |     |      |
| TCG | CAC | ATA | ACG | CGA | GGG | GAG | CAC | CGC | TTC | CAC | ATG | AGC | TAA |     |     | 1386 |
| Ser | His | Ile | Thr | Arg | Gly | Glu | His | Arg | Phe | His | Met | Ser |     |     |     |      |
|     | 450 |     |     |     |     | 455 |     |     |     |     | 460 |     |     |     |     |      |

( 2 ) INFORMATION FOR SEQ ID NO:4:

( i ) SEQUENCE CHARACTERISTICS:
        ( A ) LENGTH: 1296 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1296

( x i ) SEQUENCE DESCRIPTION: SEQ ID NO:4:

|     |     |     |     |     |     |     |     |     |     |     |     |     |     |     |     |    |
|-----|-----|-----|-----|-----|-----|-----|-----|-----|-----|-----|-----|-----|-----|-----|-----|----|
| ATG | GAT | GTC | GAT | GAG | GGT | CAA | GAC | ATG | TCC | CAA | GTT | TCA | GGA | AAG | GAG | 48 |
| Met | Asp | Val | Asp | Glu | Gly | Gln | Asp | Met | Ser | Gln | Val | Ser | Gly | Lys | Glu |    |
| 1   |     |     |     | 5   |     |     |     |     | 10  |     |     |     |     | 15  |     |    |
| AGC | CCC | CCA | GTC | AGT | GAC | ACT | CCA | GAT | GAA | GGG | GAT | GAG | CCC | ATG | CCT | 96 |

| | | | | | | | | | | | | | | | | |
|---|---|---|---|---|---|---|---|---|---|---|---|---|---|---|---|---|
| Ser | Pro | Pro | Val | Ser | Asp | Thr | Pro | Asp | Glu | Gly | Asp | Glu | Pro | Met | Pro | |
| | | | 20 | | | | | 25 | | | | | 30 | | | |
| GTC | CCT | GAG | GAC | CTG | TCC | ACT | ACC | TCT | GGA | GCA | CAG | CAG | AAC | TCC | AAG | 144 |
| Val | Pro | Glu | Asp | Leu | Ser | Thr | Thr | Ser | Gly | Ala | Gln | Gln | Asn | Ser | Lys | |
| | | 35 | | | | | 40 | | | | | 45 | | | | |
| AGT | GAT | CGA | GGC | ATG | GCC | AGT | AAT | GTT | AAA | GTA | GAG | ACT | CAG | AGT | GAT | 192 |
| Ser | Asp | Arg | Gly | Met | Ala | Ser | Asn | Val | Lys | Val | Glu | Thr | Gln | Ser | Asp | |
| | 50 | | | | | 55 | | | | | 60 | | | | | |
| GAA | GAG | AAT | GGG | CGT | GCC | TGT | GAA | ATG | AAT | GGG | GAA | GAA | TGT | GCA | GAG | 240 |
| Glu | Glu | Asn | Gly | Arg | Ala | Cys | Glu | Met | Asn | Gly | Glu | Glu | Cys | Ala | Glu | |
| 65 | | | | | 70 | | | | | 75 | | | | | 80 | |
| GAT | TTA | CGA | ATG | CTT | GAT | GCC | TCG | GGA | GAG | AAA | ATG | AAT | GGC | TCC | CAC | 288 |
| Asp | Leu | Arg | Met | Leu | Asp | Ala | Ser | Gly | Glu | Lys | Met | Asn | Gly | Ser | His | |
| | | | | 85 | | | | | 90 | | | | | 95 | | |
| AGG | GAC | CAA | GGC | AGC | TCG | GCT | TTG | TCA | GGA | GTT | GGA | GGC | ATT | CGA | CTT | 336 |
| Arg | Asp | Gln | Gly | Ser | Ser | Ala | Leu | Ser | Gly | Val | Gly | Gly | Ile | Arg | Leu | |
| | | | 100 | | | | | 105 | | | | | 110 | | | |
| CCT | AAC | GGA | AAA | CTA | AAG | TGT | GAT | ATC | TGT | GGG | ATC | GTT | TGC | ATC | GGG | 384 |
| Pro | Asn | Gly | Lys | Leu | Lys | Cys | Asp | Ile | Cys | Gly | Ile | Val | Cys | Ile | Gly | |
| | | | 115 | | | | | 120 | | | | | 125 | | | |
| CCC | AAT | GTG | CTC | ATG | GTT | CAC | AAA | AGA | AGT | CAT | ACT | GGT | GAA | CGG | CCT | 432 |
| Pro | Asn | Val | Leu | Met | Val | His | Lys | Arg | Ser | His | Thr | Gly | Glu | Arg | Pro | |
| | 130 | | | | | 135 | | | | | 140 | | | | | |
| TTC | CAG | TGC | AAC | CAG | TCT | GGG | GCC | TCC | TTT | ACC | CAG | AAA | GGC | AAC | CTC | 480 |
| Phe | Gln | Cys | Asn | Gln | Ser | Gly | Ala | Ser | Phe | Thr | Gln | Lys | Gly | Asn | Leu | |
| 145 | | | | | 150 | | | | | 155 | | | | | 160 | |
| CTG | CGG | CAC | ATC | AAG | CTG | CAC | TCG | GGT | GAG | AAG | CCC | TTC | AAA | TGC | CAT | 528 |
| Leu | Arg | His | Ile | Lys | Leu | His | Ser | Gly | Glu | Lys | Pro | Phe | Lys | Cys | His | |
| | | | | 165 | | | | | 170 | | | | | 175 | | |
| CTT | TGC | AAC | TAT | GCC | TGC | CGC | CGG | AGG | GAC | GCC | CTC | ACC | GGC | CAC | CTG | 576 |
| Leu | Cys | Asn | Tyr | Ala | Cys | Arg | Arg | Arg | Asp | Ala | Leu | Thr | Gly | His | Leu | |
| | | | 180 | | | | | 185 | | | | | 190 | | | |
| AGG | ACG | CAC | TCC | GGA | GAC | AAG | TGC | CTG | TCA | GAC | ATG | CCC | TAT | GAC | AGT | 624 |
| Arg | Thr | His | Ser | Gly | Asp | Lys | Cys | Leu | Ser | Asp | Met | Pro | Tyr | Asp | Ser | |
| | | 195 | | | | | 200 | | | | | 205 | | | | |
| GCC | AAC | TAT | GAG | AAG | GAG | GAT | ATG | ATG | ACA | TCC | CAC | GTG | ATG | GAC | CAG | 672 |
| Ala | Asn | Tyr | Glu | Lys | Glu | Asp | Met | Met | Thr | Ser | His | Val | Met | Asp | Gln | |
| 210 | | | | | 215 | | | | | 220 | | | | | | |
| GCC | ATC | AAC | AAT | GCC | ATC | AAC | TAC | CTG | GGG | GCT | GAG | TCC | CTG | CGC | CCA | 720 |
| Ala | Ile | Asn | Asn | Ala | Ile | Asn | Tyr | Leu | Gly | Ala | Glu | Ser | Leu | Arg | Pro | |
| 225 | | | | | 230 | | | | | 235 | | | | | 240 | |
| TTG | GTG | CAG | ACA | CCC | CCC | GGT | AGC | TCC | GAG | GTG | GTG | CCA | GTC | ATC | AGC | 768 |
| Leu | Val | Gln | Thr | Pro | Pro | Gly | Ser | Ser | Glu | Val | Val | Pro | Val | Ile | Ser | |
| | | | | 245 | | | | | 250 | | | | | 255 | | |
| TCC | ATG | TAC | CAG | CTG | CAC | AAG | CCC | CCC | TCA | GAT | GGC | CCC | CCA | CGG | TCC | 816 |
| Ser | Met | Tyr | Gln | Leu | His | Lys | Pro | Pro | Ser | Asp | Gly | Pro | Pro | Arg | Ser | |
| | | | 260 | | | | | 265 | | | | | 270 | | | |
| AAC | CAT | TCA | GCA | CAG | GAC | GCC | GTG | GAT | AAC | TTG | CTG | CTG | CTG | TCC | AAG | 864 |
| Asn | His | Ser | Ala | Gln | Asp | Ala | Val | Asp | Asn | Leu | Leu | Leu | Leu | Ser | Lys | |
| | | 275 | | | | | 280 | | | | | 285 | | | | |
| GCC | AAG | TCT | GTG | TCA | TCG | GAG | CGA | GAG | GCC | TCC | CCG | AGC | AAC | AGC | TGC | 912 |
| Ala | Lys | Ser | Val | Ser | Ser | Glu | Arg | Glu | Ala | Ser | Pro | Ser | Asn | Ser | Cys | |
| | | 290 | | | | | 295 | | | | | 300 | | | | |
| CAA | GAC | TCC | ACA | GAT | ACA | GAG | AGC | AAC | GCG | GAG | GAA | CAG | CGC | AGC | GGC | 960 |
| Gln | Asp | Ser | Thr | Asp | Thr | Glu | Ser | Asn | Ala | Glu | Glu | Gln | Arg | Ser | Gly | |
| 305 | | | | | 310 | | | | | 315 | | | | | 320 | |
| CTT | ATC | TAC | CTA | ACC | AAC | CAC | ATC | AAC | CCG | CAT | GCA | CGC | AAT | GGG | CTG | 1008 |
| Leu | Ile | Tyr | Leu | Thr | Asn | His | Ile | Asn | Pro | His | Ala | Arg | Asn | Gly | Leu | |
| | | | | 325 | | | | | 330 | | | | | 335 | | |
| GCT | CTC | AAG | GAG | GAG | CAG | CGC | GCC | TAC | GAG | GTG | CTG | AGG | GCG | GCC | TCA | 1056 |

| Ala | Leu | Lys | Glu | Glu | Gln | Arg | Ala | Tyr | Glu | Val | Leu | Arg | Ala | Ala | Ser | |
|-----|-----|-----|-----|-----|-----|-----|-----|-----|-----|-----|-----|-----|-----|-----|-----|---|
|     |     |     | 340 |     |     |     |     | 345 |     |     |     |     | 350 |     |     |   |

| GAG | AAC | TCG | CAG | GAT | GCC | TTC | CGT | GTG | GTC | AGC | ACG | AGT | GGC | GAG | CAG | 1104 |
|-----|-----|-----|-----|-----|-----|-----|-----|-----|-----|-----|-----|-----|-----|-----|-----|------|
| Glu | Asn | Ser | Gln | Asp | Ala | Phe | Arg | Val | Val | Ser | Thr | Ser | Gly | Glu | Gln |      |
|     |     | 355 |     |     |     |     | 360 |     |     |     |     | 365 |     |     |     |      |

| CTG | AAG | GTG | TAC | AAG | TGC | GAA | CAC | TGC | CGC | GTG | CTC | TTC | CTG | GAT | CAC | 1152 |
|-----|-----|-----|-----|-----|-----|-----|-----|-----|-----|-----|-----|-----|-----|-----|-----|------|
| Leu | Lys | Val | Tyr | Lys | Cys | Glu | His | Cys | Arg | Val | Leu | Phe | Leu | Asp | His |      |
|     | 370 |     |     |     |     | 375 |     |     |     |     | 380 |     |     |     |     |      |

| GTC | ATG | TAT | ACC | ATT | CAC | ATG | GGC | TGC | CAT | GGC | TGC | CAT | GGC | TTT | CGG | 1200 |
|-----|-----|-----|-----|-----|-----|-----|-----|-----|-----|-----|-----|-----|-----|-----|-----|------|
| Val | Met | Tyr | Thr | Ile | His | Met | Gly | Cys | His | Gly | Cys | His | Gly | Phe | Arg |      |
| 385 |     |     |     |     | 390 |     |     |     | 395 |     |     |     |     |     | 400 |      |

| GAT | CCC | TTT | GAG | TGT | AAC | ATG | TGT | GGT | TAT | CAC | AGC | CAG | GAC | AGG | TAC | 1248 |
|-----|-----|-----|-----|-----|-----|-----|-----|-----|-----|-----|-----|-----|-----|-----|-----|------|
| Asp | Pro | Phe | Glu | Cys | Asn | Met | Cys | Gly | Tyr | His | Ser | Gln | Asp | Arg | Tyr |      |
|     |     |     |     | 405 |     |     |     |     | 410 |     |     |     | 415 |     |     |      |

| GAG | TTC | TCA | TCC | CAT | ATC | ACG | CGG | GGG | GAG | CAT | CGT | TAC | CAC | CTG | AGC | 1296 |
|-----|-----|-----|-----|-----|-----|-----|-----|-----|-----|-----|-----|-----|-----|-----|-----|------|
| Glu | Phe | Ser | Ser | His | Ile | Thr | Arg | Gly | Glu | His | Arg | Tyr | His | Leu | Ser |      |
|     |     |     | 420 |     |     |     |     | 425 |     |     |     |     | 430 |     |     |      |

( 2 ) INFORMATION FOR SEQ ID NO:5:

( i ) SEQUENCE CHARACTERISTICS:
        ( A ) LENGTH: 2049 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 223..1776

( x i ) SEQUENCE DESCRIPTION: SEQ ID NO:5:

| AATTCGTTCT | ACCTTCTCTG | AACCCCAGTG | GTGTGTCAAG | GCCGGACTGG | GAGCTTGGGG | 60 |
|---|---|---|---|---|---|---|
| GAAGAGGAAG | AGGAAGAGGA | ATCTGCGGCT | CATCCAGGGA | TCAGGGTCCT | TCCCAAGTGG | 120 |
| CCACTCAGAG | GGGACTCAGA | GCAAGTCTAG | ATTTGTGTGG | CAGAGAGAGA | CAGCTCTCGT | 180 |
| TTGGCCTTGG | GGAGGCACAA | GTCTGTTGAT | AACCTGAAGA | CA ATG GAT | GTC GAT | 234 |

|     |     |     |     |     |     |     |     |     |     |     | Met | Asp | Val | Asp |     |
|-----|-----|-----|-----|-----|-----|-----|-----|-----|-----|-----|-----|-----|-----|-----|-----|
|     |     |     |     |     |     |     |     |     |     |     | 1   |     |     |     |     |

| GAG | GGT | CAA | GAC | ATG | TCC | CAA | GTT | TCA | GGA | AAG | GAG | AGC | CCC | CCA | GTC | 282 |
|-----|-----|-----|-----|-----|-----|-----|-----|-----|-----|-----|-----|-----|-----|-----|-----|-----|
| Glu | Gly | Gln | Asp | Met | Ser | Gln | Val | Ser | Gly | Lys | Glu | Ser | Pro | Pro | Val |     |
|     | 5   |     |     |     | 10  |     |     |     | 15  |     |     |     |     | 20  |     |     |

| AGT | GAC | ACT | CCA | GAT | GAA | GGG | GAT | GAG | CCC | ATG | CCT | GTC | CCT | GAG | GAC | 330 |
|-----|-----|-----|-----|-----|-----|-----|-----|-----|-----|-----|-----|-----|-----|-----|-----|-----|
| Ser | Asp | Thr | Pro | Asp | Glu | Gly | Asp | Glu | Pro | Met | Pro | Val | Pro | Glu | Asp |     |
|     |     |     |     | 25  |     |     |     |     | 30  |     |     |     |     | 35  |     |     |

| CTG | TCC | ACT | ACC | TCT | GGA | GCA | CAG | CAG | AAC | TCC | AAG | AGT | GAT | CGA | GGC | 378 |
|-----|-----|-----|-----|-----|-----|-----|-----|-----|-----|-----|-----|-----|-----|-----|-----|-----|
| Leu | Ser | Thr | Thr | Ser | Gly | Ala | Gln | Gln | Asn | Ser | Lys | Ser | Asp | Arg | Gly |     |
|     |     |     | 40  |     |     |     |     | 45  |     |     |     |     | 50  |     |     |     |

| ATG | GCC | AGT | AAT | GTT | AAA | GTA | GAG | ACT | CAG | AGT | GAT | GAA | GAG | AAT | GGG | 426 |
|-----|-----|-----|-----|-----|-----|-----|-----|-----|-----|-----|-----|-----|-----|-----|-----|-----|
| Met | Ala | Ser | Asn | Val | Lys | Val | Glu | Thr | Gln | Ser | Asp | Glu | Glu | Asn | Gly |     |
|     |     | 55  |     |     |     |     | 60  |     |     |     |     | 65  |     |     |     |     |

| CGT | GCC | TGT | GAA | ATG | AAT | GGG | GAA | GAA | TGT | GCA | GAG | GAT | TTA | CGA | ATG | 474 |
|-----|-----|-----|-----|-----|-----|-----|-----|-----|-----|-----|-----|-----|-----|-----|-----|-----|
| Arg | Ala | Cys | Glu | Met | Asn | Gly | Glu | Glu | Cys | Ala | Glu | Asp | Leu | Arg | Met |     |
|     | 70  |     |     |     |     | 75  |     |     |     |     | 80  |     |     |     |     |     |

| CTT | GAT | GCC | TCG | GGA | GAG | AAA | ATG | AAT | GGC | TCC | CAC | AGG | GAC | CAA | GGC | 522 |
|-----|-----|-----|-----|-----|-----|-----|-----|-----|-----|-----|-----|-----|-----|-----|-----|-----|
| Leu | Asp | Ala | Ser | Gly | Glu | Lys | Met | Asn | Gly | Ser | His | Arg | Asp | Gln | Gly |     |
| 85  |     |     |     |     | 90  |     |     |     |     | 95  |     |     |     |     | 100 |     |

| AGC | TCG | GCT | TTG | TCA | GGA | GTT | GGA | GGC | ATT | CGA | CTT | CCT | AAC | GGA | AAA | 570 |
|-----|-----|-----|-----|-----|-----|-----|-----|-----|-----|-----|-----|-----|-----|-----|-----|-----|
| Ser | Ser | Ala | Leu | Ser | Gly | Val | Gly | Gly | Ile | Arg | Leu | Pro | Asn | Gly | Lys |     |
|     |     |     |     | 105 |     |     |     |     | 110 |     |     |     |     | 115 |     |     |

| CTA | AAG | TGT | GAT | ATC | TGT | GGG | ATC | GTT | TGC | ATC | GGG | CCC | AAT | GTG | CTC | 618 |
|-----|-----|-----|-----|-----|-----|-----|-----|-----|-----|-----|-----|-----|-----|-----|-----|-----|
| Leu | Lys | Cys | Asp | Ile | Cys | Gly | Ile | Val | Cys | Ile | Gly | Pro | Asn | Val | Leu |     |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 120 |     |     |     |     |     | 125 |     |     |     |     |     | 130 |      |
| ATG | GTT | CAC | AAA | AGA | AGT | CAT | ACT | GGT | GAA | CGG | CCT | TTC | CAG | TGC | AAC | 666  |
| Met | Val | His | Lys | Arg | Ser | His | Thr | Gly | Glu | Arg | Pro | Phe | Gln | Cys | Asn |      |
|     |     | 135 |     |     |     |     | 140 |     |     |     |     | 145 |     |     |     |      |
| CAG | TCT | GGG | GCC | TCC | TTT | ACC | CAG | AAA | GGC | AAC | CTC | CTG | CGG | CAC | ATC | 714  |
| Gln | Ser | Gly | Ala | Ser | Phe | Thr | Gln | Lys | Gly | Asn | Leu | Leu | Arg | His | Ile |      |
|     | 150 |     |     |     |     | 155 |     |     |     |     | 160 |     |     |     |     |      |
| AAG | CTG | CAC | TCG | GGT | GAG | AAG | CCC | TTC | AAA | TGC | CAT | CTT | TGC | AAC | TAT | 762  |
| Lys | Leu | His | Ser | Gly | Glu | Lys | Pro | Phe | Lys | Cys | His | Leu | Cys | Asn | Tyr |      |
| 165 |     |     |     |     | 170 |     |     |     |     | 175 |     |     |     |     | 180 |      |
| GCC | TGC | CGC | CGG | AGG | GAC | GCC | CTC | ACC | GGC | CAC | CTG | AGG | ACG | CAC | TCC | 810  |
| Ala | Cys | Arg | Arg | Arg | Asp | Ala | Leu | Thr | Gly | His | Leu | Arg | Thr | His | Ser |      |
|     |     |     |     | 185 |     |     |     |     | 190 |     |     |     |     | 195 |     |      |
| GTT | GGT | AAG | CCT | CAC | AAA | TGT | GGA | TAT | TGT | GGC | CGG | AGC | TAT | AAA | CAG | 858  |
| Val | Gly | Lys | Pro | His | Lys | Cys | Gly | Tyr | Cys | Gly | Arg | Ser | Tyr | Lys | Gln |      |
|     |     |     | 200 |     |     |     |     | 205 |     |     |     |     | 210 |     |     |      |
| CGA | AGC | TCT | TTA | GAG | GAG | CAT | AAA | GAG | CGA | TGC | CAC | AAC | TAC | TTG | GAA | 906  |
| Arg | Ser | Ser | Leu | Glu | Glu | His | Lys | Glu | Arg | Cys | His | Asn | Tyr | Leu | Glu |      |
|     |     | 215 |     |     |     |     | 220 |     |     |     |     | 225 |     |     |     |      |
| AGC | ATG | GGC | CTT | CCG | GGC | GTG | TGC | CCA | GTC | ATT | AAG | GAA | GAA | ACT | AAC | 954  |
| Ser | Met | Gly | Leu | Pro | Gly | Val | Cys | Pro | Val | Ile | Lys | Glu | Glu | Thr | Asn |      |
|     | 230 |     |     |     |     | 235 |     |     |     |     | 240 |     |     |     |     |      |
| CAC | AAC | GAG | ATG | GCA | GAA | GAC | CTG | TGC | AAG | ATA | GGA | GCA | GAG | AGG | TCC | 1002 |
| His | Asn | Glu | Met | Ala | Glu | Asp | Leu | Cys | Lys | Ile | Gly | Ala | Glu | Arg | Ser |      |
| 245 |     |     |     |     | 250 |     |     |     |     | 255 |     |     |     |     | 260 |      |
| CTT | GTC | CTG | GAC | AGG | CTG | GCA | AGC | AAT | GTC | GCC | AAA | CGT | AAG | AGC | TCT | 1050 |
| Leu | Val | Leu | Asp | Arg | Leu | Ala | Ser | Asn | Val | Ala | Lys | Arg | Lys | Ser | Ser |      |
|     |     |     |     | 265 |     |     |     |     | 270 |     |     |     |     | 275 |     |      |
| ATG | CCT | CAG | AAA | TTT | CTT | GGA | GAC | AAG | TGC | CTG | TCA | GAC | ATG | CCC | TAT | 1098 |
| Met | Pro | Gln | Lys | Phe | Leu | Gly | Asp | Lys | Cys | Leu | Ser | Asp | Met | Pro | Tyr |      |
|     |     |     | 280 |     |     |     |     | 285 |     |     |     |     | 290 |     |     |      |
| GAC | AGT | GCC | AAC | TAT | GAG | AAG | GAG | GAT | ATG | ATG | ACA | TCC | CAC | GTG | ATG | 1146 |
| Asp | Ser | Ala | Asn | Tyr | Glu | Lys | Glu | Asp | Met | Met | Thr | Ser | His | Val | Met |      |
|     |     | 295 |     |     |     |     | 300 |     |     |     |     | 305 |     |     |     |      |
| GAC | CAG | GCC | ATC | AAC | AAT | GCC | ATC | AAC | TAC | CTG | GGG | GCT | GAG | TCC | CTG | 1194 |
| Asp | Gln | Ala | Ile | Asn | Asn | Ala | Ile | Asn | Tyr | Leu | Gly | Ala | Glu | Ser | Leu |      |
|     | 310 |     |     |     |     | 315 |     |     |     |     | 320 |     |     |     |     |      |
| CGC | CCA | TTG | GTG | CAG | ACA | CCC | CCC | GGT | AGC | TCC | GAG | GTG | GTG | CCA | GTC | 1242 |
| Arg | Pro | Leu | Val | Gln | Thr | Pro | Pro | Gly | Ser | Ser | Glu | Val | Val | Pro | Val |      |
| 325 |     |     |     |     | 330 |     |     |     |     | 335 |     |     |     |     | 340 |      |
| ATC | AGC | TCC | ATG | TAC | CAG | CTG | CAC | AAG | CCC | CCC | TCA | GAT | GGC | CCC | CCA | 1290 |
| Ile | Ser | Ser | Met | Tyr | Gln | Leu | His | Lys | Pro | Pro | Ser | Asp | Gly | Pro | Pro |      |
|     |     |     |     | 345 |     |     |     |     | 350 |     |     |     |     | 355 |     |      |
| CGG | TCC | AAC | CAT | TCA | GCA | CAG | GAC | GCC | GTG | GAT | AAC | TTG | CTG | CTG | CTG | 1338 |
| Arg | Ser | Asn | His | Ser | Ala | Gln | Asp | Ala | Val | Asp | Asn | Leu | Leu | Leu | Leu |      |
|     |     |     | 360 |     |     |     |     | 365 |     |     |     |     | 370 |     |     |      |
| TCC | AAG | GCC | AAG | TCT | GTG | TCA | TCG | GAG | CGA | GAG | GCC | TCC | CCG | AGC | AAC | 1386 |
| Ser | Lys | Ala | Lys | Ser | Val | Ser | Ser | Glu | Arg | Glu | Ala | Ser | Pro | Ser | Asn |      |
|     |     | 375 |     |     |     |     | 380 |     |     |     |     | 385 |     |     |     |      |
| AGC | TGC | CAA | GAC | TCC | ACA | GAT | ACA | GAG | AGC | AAC | GCG | GAG | GAA | CAG | CGC | 1434 |
| Ser | Cys | Gln | Asp | Ser | Thr | Asp | Thr | Glu | Ser | Asn | Ala | Glu | Glu | Gln | Arg |      |
|     |     | 390 |     |     |     |     | 395 |     |     |     |     | 400 |     |     |     |      |
| AGC | GGC | CTT | ATC | TAC | CTA | ACC | AAC | CAC | ATC | AAC | CCG | CAT | GCA | CGC | AAT | 1482 |
| Ser | Gly | Leu | Ile | Tyr | Leu | Thr | Asn | His | Ile | Asn | Pro | His | Ala | Arg | Asn |      |
| 405 |     |     |     |     | 410 |     |     |     |     | 415 |     |     |     |     | 420 |      |
| GGG | CTG | GCT | CTC | AAG | GAG | GAG | CAG | CGC | GCC | TAC | GAG | GTG | CTG | AGG | GCG | 1530 |
| Gly | Leu | Ala | Leu | Lys | Glu | Glu | Gln | Arg | Ala | Tyr | Glu | Val | Leu | Arg | Ala |      |
|     |     |     |     | 425 |     |     |     |     | 430 |     |     |     |     | 435 |     |      |
| GCC | TCA | GAG | AAC | TCG | CAG | GAT | GCC | TTC | CGT | GTG | GTC | AGC | ACG | AGT | GGC | 1578 |
| Ala | Ser | Glu | Asn | Ser | Gln | Asp | Ala | Phe | Arg | Val | Val | Ser | Thr | Ser | Gly |      |

```
                         440                          445                          450
GAG  CAG  CTG  AAG  GTG  TAC  AAG  TGC  GAA  CAC  TGC  CGC  GTG  CTC  TTC  CTG    1626
Glu  Gln  Leu  Lys  Val  Tyr  Lys  Cys  Glu  His  Cys  Arg  Val  Leu  Phe  Leu
          455                      460                      465

GAT  CAC  GTC  ATG  TAT  ACC  ATT  CAC  ATG  GGC  TGC  CAT  GGC  TGC  CAT  GGC    1674
Asp  His  Val  Met  Tyr  Thr  Ile  His  Met  Gly  Cys  His  Gly  Cys  His  Gly
     470                      475                      480

TTT  CGG  GAT  CCC  TTT  GAG  TGT  AAC  ATG  TGT  GGT  TAT  CAC  AGC  CAG  GAC    1722
Phe  Arg  Asp  Pro  Phe  Glu  Cys  Asn  Met  Cys  Gly  Tyr  His  Ser  Gln  Asp
485                      490                      495                      500

AGG  TAC  GAG  TTC  TCA  TCC  CAT  ATC  ACG  CGG  GGG  GAG  CAT  CGT  TAC  CAC    1770
Arg  Tyr  Glu  Phe  Ser  Ser  His  Ile  Thr  Arg  Gly  Glu  His  Arg  Tyr  His
                    505                      510                      515

CTG  AGC  TAAACCCAGC  CAGGCCCCAC  TGAAGCACAA  AGATAGCTGG  TTATGCCTCC              1826
Leu  Ser

TTCCCGGCAG  CTGGACCCAC  AGCGGACAAT  GTGGGAGTGG  ATTTGCAGGC  AGCATTTGTT            1886

CTTTTATGTT  GGTTGTTTGG  CGTTTCATTT  GCGTTGGAAG  ATAAGTTTTT  AATGTTAGTG            1946

ACAGGATTGC  ATTGCATCAG  CAACATTCAC  AACATCCATC  CTTCTAGCCA  GTTTGTTCA             2006

CTGGTAGCTG  AGGTTTCCCG  GATATGTGGC  TTCCTAACAC  TCT                              2049
```

( 2 ) INFORMATION FOR SEQ ID NO:6:

( i ) SEQUENCE CHARACTERISTICS:
        ( A ) LENGTH: 1170 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1170

( x i ) SEQUENCE DESCRIPTION: SEQ ID NO:6:

```
ATG  GAT  GTC  GAT  GAG  GGT  CAA  GAC  ATG  TCC  CAA  GTT  TCA  GGA  AAG  GAG      48
Met  Asp  Val  Asp  Glu  Gly  Gln  Asp  Met  Ser  Gln  Val  Ser  Gly  Lys  Glu
1                   5                        10                       15

AGC  CCC  CCA  GTC  AGT  GAC  ACT  CCA  GAT  GAA  GGG  GAT  GAG  CCC  ATG  CCT      96
Ser  Pro  Pro  Val  Ser  Asp  Thr  Pro  Asp  Glu  Gly  Asp  Glu  Pro  Met  Pro
               20                       25                       30

GTC  CCT  GAG  GAC  CTG  TCC  ACT  ACC  TCT  GGA  GCA  CAG  CAG  AAC  TCC  AAG     144
Val  Pro  Glu  Asp  Leu  Ser  Thr  Thr  Ser  Gly  Ala  Gln  Gln  Asn  Ser  Lys
                    35                       40                       45

AGT  GAT  CGA  GGC  ATG  GGT  GAA  CGG  CCT  TTC  CAG  TGC  AAC  CAG  TCT  GGG     192
Ser  Asp  Arg  Gly  Met  Gly  Glu  Arg  Pro  Phe  Gln  Cys  Asn  Gln  Ser  Gly
     50                       55                       60

GCC  TCC  TTT  ACC  CAG  AAA  GGC  AAC  CTC  CTG  CGG  CAC  ATC  AAG  CTG  CAC     240
Ala  Ser  Phe  Thr  Gln  Lys  Gly  Asn  Leu  Leu  Arg  His  Ile  Lys  Leu  His
65                       70                       75                       80

TCG  GGT  GAG  AAG  CCC  TTC  AAA  TGC  CAT  CTT  TGC  AAC  TAT  GCC  TGC  CGC     288
Ser  Gly  Glu  Lys  Pro  Phe  Lys  Cys  His  Leu  Cys  Asn  Tyr  Ala  Cys  Arg
                    85                       90                       95

CGG  AGG  GAC  GCC  CTC  ACC  GGC  CAC  CTG  AGG  ACG  CAC  TCC  GTC  ATT  AAG     336
Arg  Arg  Asp  Ala  Leu  Thr  Gly  His  Leu  Arg  Thr  His  Ser  Val  Ile  Lys
                    100                      105                      110

GAA  GAA  ACT  AAC  CAC  AAC  GAG  ATG  GCA  GAA  GAC  CTG  TGC  AAG  ATA  GGA     384
Glu  Glu  Thr  Asn  His  Asn  Glu  Met  Ala  Glu  Asp  Leu  Cys  Lys  Ile  Gly
          115                      120                      125

GCA  GAG  AGG  TCC  CTT  GTC  CTG  GAC  AGG  CTG  GCA  AGC  AAT  GTC  GCC  AAA     432
Ala  Glu  Arg  Ser  Leu  Val  Leu  Asp  Arg  Leu  Ala  Ser  Asn  Val  Ala  Lys
```

```
              130                          135                           140
CGT  AAG  AGC  TCT  ATG  CCT  CAG  AAA  TTT  CTT  GGA  GAC  AAG  TGC  CTG  TCA    480
Arg  Lys  Ser  Ser  Met  Pro  Gln  Lys  Phe  Leu  Gly  Asp  Lys  Cys  Leu  Ser
145            150                           155                           160

GAC  ATG  CCC  TAT  GAC  AGT  GCC  AAC  TAT  GAG  AAG  GAG  GAT  ATG  ATG  ACA    528
Asp  Met  Pro  Tyr  Asp  Ser  Ala  Asn  Tyr  Glu  Lys  Glu  Asp  Met  Met  Thr
                    165                      170                     175

TCC  CAC  GTG  ATG  GAC  CAG  GCC  ATC  AAC  AAT  GCC  ATC  AAC  TAC  CTG  GGG    576
Ser  His  Val  Met  Asp  Gln  Ala  Ile  Asn  Asn  Ala  Ile  Asn  Tyr  Leu  Gly
               180                      185                     190

GCT  GAG  TCC  CTG  CGC  CCA  TTG  GTG  CAG  ACA  CCC  CCC  GGT  AGC  TCC  GAG    624
Ala  Glu  Ser  Leu  Arg  Pro  Leu  Val  Gln  Thr  Pro  Pro  Gly  Ser  Ser  Glu
          195                      200                     205

GTG  GTG  CCA  GTC  ATC  AGC  TCC  ATG  TAC  CAG  CTG  CAC  AAG  CCC  CCC  TCA    672
Val  Val  Pro  Val  Ile  Ser  Ser  Met  Tyr  Gln  Leu  His  Lys  Pro  Pro  Ser
     210                      215                     220

GAT  GGC  CCC  CCA  CGG  TCC  AAC  CAT  TCA  GCA  CAG  GAC  GCC  GTG  GAT  AAC    720
Asp  Gly  Pro  Pro  Arg  Ser  Asn  His  Ser  Ala  Gln  Asp  Ala  Val  Asp  Asn
225                      230                     235                          240

TTG  CTG  CTG  CTG  TCC  AAG  GCC  AAG  TCT  GTG  TCA  TCG  GAG  CGA  GAG  GCC    768
Leu  Leu  Leu  Leu  Ser  Lys  Ala  Lys  Ser  Val  Ser  Ser  Glu  Arg  Glu  Ala
                    245                      250                     255

TCC  CCG  AGC  AAC  AGC  TGC  CAA  GAC  TCC  ACA  GAT  ACA  GAG  AGC  AAC  GCG    816
Ser  Pro  Ser  Asn  Ser  Cys  Gln  Asp  Ser  Thr  Asp  Thr  Glu  Ser  Asn  Ala
               260                      265                     270

GAG  GAA  CAG  CGC  AGC  GGC  CTT  ATC  TAC  CTA  ACC  AAC  CAC  ATC  AAC  CCG    864
Glu  Glu  Gln  Arg  Ser  Gly  Leu  Ile  Tyr  Leu  Thr  Asn  His  Ile  Asn  Pro
          275                      280                     285

CAT  GCA  CGC  AAT  GGG  CTG  GCT  CTC  AAG  GAG  GAG  CAG  CGC  GCC  TAC  GAG    912
His  Ala  Arg  Asn  Gly  Leu  Ala  Leu  Lys  Glu  Glu  Gln  Arg  Ala  Tyr  Glu
     290                      295                     300

GTG  CTG  AGG  GCG  GCC  TCA  GAG  AAC  TCG  CAG  GAT  GCC  TTC  CGT  GTG  GTC    960
Val  Leu  Arg  Ala  Ala  Ser  Glu  Asn  Ser  Gln  Asp  Ala  Phe  Arg  Val  Val
305                      310                     315                          320

AGC  ACG  AGT  GGC  GAG  CAG  CTG  AAG  GTG  TAC  AAG  TGC  GAA  CAC  TGC  CGC   1008
Ser  Thr  Ser  Gly  Glu  Gln  Leu  Lys  Val  Tyr  Lys  Cys  Glu  His  Cys  Arg
                    325                      330                     335

GTG  CTC  TTC  CTG  GAT  CAC  GTC  ATG  TAT  ACC  ATT  CAC  ATG  GGC  TGC  CAT   1056
Val  Leu  Phe  Leu  Asp  His  Val  Met  Tyr  Thr  Ile  His  Met  Gly  Cys  His
               340                      345                     350

GGC  TGC  CAT  GGC  TTT  CGG  GAT  CCC  TTT  GAG  TGT  AAC  ATG  TGT  GGT  TAT   1104
Gly  Cys  His  Gly  Phe  Arg  Asp  Pro  Phe  Glu  Cys  Asn  Met  Cys  Gly  Tyr
          355                      360                     365

CAC  AGC  CAG  GAC  AGG  TAC  GAG  TTC  TCA  TCC  CAT  ATC  ACG  CGG  GGG  GAG   1152
His  Ser  Gln  Asp  Arg  Tyr  Glu  Phe  Ser  Ser  His  Ile  Thr  Arg  Gly  Glu
     370                      375                     380

CAT  CGT  TAC  CAC  CTG  AGC                                                    1170
His  Arg  Tyr  His  Leu  Ser
385                 390
```

( 2 ) INFORMATION FOR SEQ ID NO:7:

( i ) SEQUENCE CHARACTERISTICS:
        ( A ) LENGTH: 1128 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1128

(xi) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GAT | GTC | GAT | GAG | GGT | CAA | GAC | ATG | TCC | CAA | GTT | TCA | GGA | AAG | GAG | 48 |
| Met | Asp | Val | Asp | Glu | Gly | Gln | Asp | Met | Ser | Gln | Val | Ser | Gly | Lys | Glu | |
| 1 | | | | 5 | | | | | 10 | | | | | 15 | | |
| AGC | CCC | CCA | GTC | AGT | GAC | ACT | CCA | GAT | GAA | GGG | GAT | GAG | CCC | ATG | CCT | 96 |
| Ser | Pro | Pro | Val | Ser | Asp | Thr | Pro | Asp | Glu | Gly | Asp | Glu | Pro | Met | Pro | |
| | | | 20 | | | | | 25 | | | | | 30 | | | |
| GTC | CCT | GAG | GAC | CTG | TCC | ACT | ACC | TCT | GGA | GCA | CAG | CAG | AAC | TCC | AAG | 144 |
| Val | Pro | Glu | Asp | Leu | Ser | Thr | Thr | Ser | Gly | Ala | Gln | Gln | Asn | Ser | Lys | |
| | | 35 | | | | | 40 | | | | | 45 | | | | |
| AGT | GAT | CGA | GGC | ATG | GCC | AGT | AAT | GTT | AAA | GTA | GAG | ACT | CAG | AGT | GAT | 192 |
| Ser | Asp | Arg | Gly | Met | Ala | Ser | Asn | Val | Lys | Val | Glu | Thr | Gln | Ser | Asp | |
| | 50 | | | | | 55 | | | | | 60 | | | | | |
| GAA | GAG | AAT | GGG | CGT | GCC | TGT | GAA | ATG | AAT | GGG | GAA | GAA | TGT | GCA | GAG | 240 |
| Glu | Glu | Asn | Gly | Arg | Ala | Cys | Glu | Met | Asn | Gly | Glu | Glu | Cys | Ala | Glu | |
| 65 | | | | | 70 | | | | | 75 | | | | | 80 | |
| GAT | TTA | CGA | ATG | CTT | GAT | GCC | TCG | GGA | GAG | AAA | ATG | AAT | GGC | TCC | CAC | 288 |
| Asp | Leu | Arg | Met | Leu | Asp | Ala | Ser | Gly | Glu | Lys | Met | Asn | Gly | Ser | His | |
| | | | | 85 | | | | | 90 | | | | | 95 | | |
| AGG | GAC | CAA | GGC | AGC | TCG | GCT | TTG | TCA | GGA | GTT | GGA | GGC | ATT | CGA | CTT | 336 |
| Arg | Asp | Gln | Gly | Ser | Ser | Ala | Leu | Ser | Gly | Val | Gly | Gly | Ile | Arg | Leu | |
| | | | 100 | | | | | 105 | | | | | 110 | | | |
| CCT | AAC | GGA | AAA | CTA | AAG | TGT | GAT | ATC | TGT | GGG | ATC | GTT | TGC | ATC | GGG | 384 |
| Pro | Asn | Gly | Lys | Leu | Lys | Cys | Asp | Ile | Cys | Gly | Ile | Val | Cys | Ile | Gly | |
| | | 115 | | | | | 120 | | | | | 125 | | | | |
| CCC | AAT | GTG | CTC | ATG | GTT | CAC | AAA | AGA | AGT | CAT | ACT | GGA | GAC | AAG | TGC | 432 |
| Pro | Asn | Val | Leu | Met | Val | His | Lys | Arg | Ser | His | Thr | Gly | Asp | Lys | Cys | |
| | 130 | | | | | 135 | | | | | 140 | | | | | |
| CTG | TCA | GAC | ATG | CCC | TAT | GAC | AGT | GCC | AAC | TAT | GAG | AAG | GAG | GAT | ATG | 480 |
| Leu | Ser | Asp | Met | Pro | Tyr | Asp | Ser | Ala | Asn | Tyr | Glu | Lys | Glu | Asp | Met | |
| 145 | | | | | 150 | | | | | 155 | | | | | 160 | |
| ATG | ACA | TCC | CAC | GTG | ATG | GAC | CAG | GCC | ATC | AAC | AAT | GCC | ATC | AAC | TAC | 528 |
| Met | Thr | Ser | His | Val | Met | Asp | Gln | Ala | Ile | Asn | Asn | Ala | Ile | Asn | Tyr | |
| | | | | 165 | | | | | 170 | | | | | 175 | | |
| CTG | GGG | GCT | GAG | TCC | CTG | CGC | CCA | TTG | GTG | CAG | ACA | CCC | CCC | GGT | AGC | 576 |
| Leu | Gly | Ala | Glu | Ser | Leu | Arg | Pro | Leu | Val | Gln | Thr | Pro | Pro | Gly | Ser | |
| | | | 180 | | | | | 185 | | | | | 190 | | | |
| TCC | GAG | GTG | GTG | CCA | GTC | ATC | AGC | TCC | ATG | TAC | CAG | CTG | CAC | AAG | CCC | 624 |
| Ser | Glu | Val | Val | Pro | Val | Ile | Ser | Ser | Met | Tyr | Gln | Leu | His | Lys | Pro | |
| | | 195 | | | | | 200 | | | | | 205 | | | | |
| CCC | TCA | GAT | GGC | CCC | CCA | CGG | TCC | AAC | CAT | TCA | GCA | CAG | GAC | GCC | GTG | 672 |
| Pro | Ser | Asp | Gly | Pro | Pro | Arg | Ser | Asn | His | Ser | Ala | Gln | Asp | Ala | Val | |
| | 210 | | | | | 215 | | | | | 220 | | | | | |
| GAT | AAC | TTG | CTG | CTG | CTG | TCC | AAG | GCC | AAG | TCT | GTG | TCA | TCG | GAG | CGA | 720 |
| Asp | Asn | Leu | Leu | Leu | Leu | Ser | Lys | Ala | Lys | Ser | Val | Ser | Ser | Glu | Arg | |
| 225 | | | | | 230 | | | | | 235 | | | | | 240 | |
| GAG | GCC | TCC | CCG | AGC | AAC | AGC | TGC | CAA | GAC | TCC | ACA | GAT | ACA | GAG | AGC | 768 |
| Glu | Ala | Ser | Pro | Ser | Asn | Ser | Cys | Gln | Asp | Ser | Thr | Asp | Thr | Glu | Ser | |
| | | | | 245 | | | | | 250 | | | | | 255 | | |
| AAC | GCG | GAG | GAA | CAG | CGC | AGC | GGC | CTT | ATC | TAC | CTA | ACC | AAC | CAC | ATC | 816 |
| Asn | Ala | Glu | Glu | Gln | Arg | Ser | Gly | Leu | Ile | Tyr | Leu | Thr | Asn | His | Ile | |
| | | | 260 | | | | | 265 | | | | | 270 | | | |
| AAC | CCG | CAT | GCA | CGC | AAT | GGG | CTG | GCT | CTC | AAG | GAG | GAG | CAG | CGC | GCC | 864 |
| Asn | Pro | His | Ala | Arg | Asn | Gly | Leu | Ala | Leu | Lys | Glu | Glu | Gln | Arg | Ala | |
| | | 275 | | | | | 280 | | | | | 285 | | | | |
| TAC | GAG | GTG | CTG | AGG | GCG | GCC | TCA | GAG | AAC | TCG | CAG | GAT | GCC | TTC | CGT | 912 |
| Tyr | Glu | Val | Leu | Arg | Ala | Ala | Ser | Glu | Asn | Ser | Gln | Asp | Ala | Phe | Arg | |
| | 290 | | | | | 295 | | | | | 300 | | | | | |
| GTG | GTC | AGC | ACG | AGT | GGC | GAG | CAG | CTG | AAG | GTG | TAC | AAG | TGC | GAA | CAC | 960 |

```
Val  Val  Ser  Thr  Ser  Gly  Glu  Gln  Leu  Lys  Val  Tyr  Lys  Cys  Glu  His
305                 310                      315                      320

TGC  CGC  GTG  CTC  TTC  CTG  GAT  CAC  GTC  ATG  TAT  ACC  ATT  CAC  ATG  GGC        1008
Cys  Arg  Val  Leu  Phe  Leu  Asp  His  Val  Met  Tyr  Thr  Ile  His  Met  Gly
               325                      330                      335

TGC  CAT  GGC  TGC  CAT  GGC  TTT  CGG  GAT  CCC  TTT  GAG  TGT  AAC  ATG  TGT        1056
Cys  His  Gly  Cys  His  Gly  Phe  Arg  Asp  Pro  Phe  Glu  Cys  Asn  Met  Cys
               340                      345                      350

GGT  TAT  CAC  AGC  CAG  GAC  AGG  TAC  GAG  TTC  TCA  TCC  CAT  ATC  ACG  CGG        1104
Gly  Tyr  His  Ser  Gln  Asp  Arg  Tyr  Glu  Phe  Ser  Ser  His  Ile  Thr  Arg
               355                      360                      365

GGG  GAG  CAT  CGT  TAC  CAC  CTG  AGC                                                 1128
Gly  Glu  His  Arg  Tyr  His  Leu  Ser
          370                 375
```

( 2 ) INFORMATION FOR SEQ ID NO:8:

( i ) SEQUENCE CHARACTERISTICS:
        ( A ) LENGTH: 1004 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1002

( x i ) SEQUENCE DESCRIPTION: SEQ ID NO:8:

```
GGA  GAA  CGG  CCC  TTC  CAG  TGC  AAT  CAG  TGC  GGG  GCC  TCA  TTC  ACC  CAG          48
Gly  Glu  Arg  Pro  Phe  Gln  Cys  Asn  Gln  Cys  Gly  Ala  Ser  Phe  Thr  Gln
1                       5                        10                      15

AAG  GGC  AAC  CTG  CTC  CGG  CAC  ATC  AAG  CTG  CAT  TCC  GGG  GAG  AAG  CCC          96
Lys  Gly  Asn  Leu  Leu  Arg  His  Ile  Lys  Leu  His  Ser  Gly  Glu  Lys  Pro
               20                       25                      30

TTC  AAA  TGC  CAC  CTC  TGC  AAC  TAC  GCC  TGC  CGC  CGG  AGG  GAC  GCC  CTC         144
Phe  Lys  Cys  His  Leu  Cys  Asn  Tyr  Ala  Cys  Arg  Arg  Arg  Asp  Ala  Leu
               35                       40                      45

ACT  GGC  CAC  CTG  AGG  ACG  CAC  TCC  GTC  ATT  AAA  GAA  GAA  ACT  AAG  CAC         192
Thr  Gly  His  Leu  Arg  Thr  His  Ser  Val  Ile  Lys  Glu  Glu  Thr  Lys  His
               50                       55                      60

AGT  GAA  ATG  GCA  GAA  GAC  CTG  TGC  AAG  ATA  GGA  TCA  GAG  AGA  TCT  CTC         240
Ser  Glu  Met  Ala  Glu  Asp  Leu  Cys  Lys  Ile  Gly  Ser  Glu  Arg  Ser  Leu
65                      70                       75                      80

GTG  CTG  GAC  AGA  CTA  GCA  AGT  AAT  GTC  GCC  AAA  CGT  AAG  AGC  TCT  ATG         288
Val  Leu  Asp  Arg  Leu  Ala  Ser  Asn  Val  Ala  Lys  Arg  Lys  Ser  Ser  Met
               85                       90                      95

CCT  CAG  AAA  TTT  CTT  GGG  GAC  AAG  GGC  CTG  TCC  GAC  ACG  CCC  TAC  GAC         336
Pro  Gln  Lys  Phe  Leu  Gly  Asp  Lys  Gly  Leu  Ser  Asp  Thr  Pro  Tyr  Asp
               100                      105                     110

AGT  GCC  ACG  TAC  GAG  AAG  GAG  AAC  GAA  ATG  ATG  AAG  TCC  CAC  GTG  ATG         384
Ser  Ala  Thr  Tyr  Glu  Lys  Glu  Asn  Glu  Met  Met  Lys  Ser  His  Val  Met
               115                      120                     125

GAC  CAA  GCC  ATC  AAC  AAC  GCC  ATC  AAC  TAC  CTG  GGG  GCC  GAG  TCC  CTG         432
Asp  Gln  Ala  Ile  Asn  Asn  Ala  Ile  Asn  Tyr  Leu  Gly  Ala  Glu  Ser  Leu
               130                      135                     140

CGC  CCG  CTG  GTG  CAG  ACG  CCC  CCG  GGC  GGT  TCC  GAG  GTG  GTC  CCG  GTC         480
Arg  Pro  Leu  Val  Gln  Thr  Pro  Pro  Gly  Gly  Ser  Glu  Val  Val  Pro  Val
145                     150                      155                     160

ATC  AGC  CCG  ATG  TAC  CAG  CTG  CAC  AGG  CGC  TCG  GAG  GGC  ACC  CCG  CGC         528
Ile  Ser  Pro  Met  Tyr  Gln  Leu  His  Arg  Arg  Ser  Glu  Gly  Thr  Pro  Arg
               165                      170                     175
```

| | | | | | | | | | | | | | | | | |
|---|---|---|---|---|---|---|---|---|---|---|---|---|---|---|---|---|
| TCC | AAC | CAC | TCG | GCC | CAG | GAC | AGC | GCC | GTG | GAG | TAC | CTG | CTG | CTG | CTC | 576 |
| Ser | Asn | His | Ser | Ala | Gln | Asp | Ser | Ala | Val | Glu | Tyr | Leu | Leu | Leu | Leu | |
| | | | 180 | | | | | 185 | | | | | 190 | | | |
| TCC | AAG | GCC | AAG | TTG | GTG | CCC | TCG | GAG | CGC | GAG | GCG | TCC | CCG | AGC | AAC | 624 |
| Ser | Lys | Ala | Lys | Leu | Val | Pro | Ser | Glu | Arg | Glu | Ala | Ser | Pro | Ser | Asn | |
| | | 195 | | | | | 200 | | | | | 205 | | | | |
| AGC | TGC | CAA | GAC | TCC | ACG | GAC | ACC | GAG | AGC | AAC | AAC | GAG | GAG | CAG | CGC | 672 |
| Ser | Cys | Gln | Asp | Ser | Thr | Asp | Thr | Glu | Ser | Asn | Asn | Glu | Glu | Gln | Arg | |
| 210 | | | | | 215 | | | | | 220 | | | | | | |
| AGC | GGT | CTT | ATC | TAC | CTG | ACC | AAC | CAC | ATC | GCC | CGA | CGC | GCG | CAA | CGC | 720 |
| Ser | Gly | Leu | Ile | Tyr | Leu | Thr | Asn | His | Ile | Ala | Arg | Arg | Ala | Gln | Arg | |
| 225 | | | | | 230 | | | | | 235 | | | | | 240 | |
| GTG | TCG | CTC | AAG | GAG | GAG | CAC | CGC | GCC | TAC | GAC | CTG | CTG | CGC | GCC | GCC | 768 |
| Val | Ser | Leu | Lys | Glu | Glu | His | Arg | Ala | Tyr | Asp | Leu | Leu | Arg | Ala | Ala | |
| | | | | 245 | | | | | 250 | | | | | 255 | | |
| TCC | GAG | AAC | TCG | CAG | GAC | GCG | CTC | CGC | GTG | GTC | AGC | ACC | AGC | GGG | GAG | 816 |
| Ser | Glu | Asn | Ser | Gln | Asp | Ala | Leu | Arg | Val | Val | Ser | Thr | Ser | Gly | Glu | |
| | | | 260 | | | | | 265 | | | | | 270 | | | |
| CAG | ATG | AAG | GTG | TAC | AAG | TGC | GAA | CAC | TGC | CGG | GTG | CTC | TTC | CTG | GAT | 864 |
| Gln | Met | Lys | Val | Tyr | Lys | Cys | Glu | His | Cys | Arg | Val | Leu | Phe | Leu | Asp | |
| | | 275 | | | | | 280 | | | | | 285 | | | | |
| CAC | GTC | ATG | TAC | ACC | ATC | CAC | ATG | GGC | TGC | CAC | GGC | TTC | CGT | GAT | CCT | 912 |
| His | Val | Met | Tyr | Thr | Ile | His | Met | Gly | Cys | His | Gly | Phe | Arg | Asp | Pro | |
| | | 290 | | | | | 295 | | | | | 300 | | | | |
| TTT | GAG | TGC | AAC | ATG | TGC | GGC | TAC | CAC | AGC | CAG | GAC | CGG | TAC | GAG | TTC | 960 |
| Phe | Glu | Cys | Asn | Met | Cys | Gly | Tyr | His | Ser | Gln | Asp | Arg | Tyr | Glu | Phe | |
| 305 | | | | | 310 | | | | | 315 | | | | | 320 | |
| TCG | TCG | CAC | ATA | ACG | CGA | GGG | GAG | CAC | CGC | TTC | CAC | ATG | AGC | TA | | 1004 |
| Ser | Ser | His | Ile | Thr | Arg | Gly | Glu | His | Arg | Phe | His | Met | Ser | | | |
| | | | | 325 | | | | | 330 | | | | | | | |

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGGCGATTTT GGGAATTTCA CACC                                  24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

AGGCCATGGG AATGAAGGAA CACC                                  24

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGTGTAAATT GGGAATGCTG TGCCT 25

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

AGGCATGGGA ATGTCTGGAA CACC 24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AGGCATTAAA ATGGGAATAA CACC 24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GGTGTAGGAA TGCGGTAATT GCCT 24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GGTGTGGGAA TAACTGGGAT GCCT 24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GGTGTGGGAA TGTCACTTCA GCCT 24

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGTGTGGGAA TACTGAGTAT GCCTGCCT 28

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

AGGCAAATTT GGGAATACTA CACC 24

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GGTGTGTGGG AACATGGGAT GCCT 24

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

AGGCCTATTT CCCTTGGGAA CACC 24

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GGTGTGGAAC ATCGTGGGAA GCCGCCT 27

( 2 ) INFORMATION FOR SEQ ID NO:22:

( i ) SEQUENCE CHARACTERISTICS:
        ( A ) LENGTH: 24 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:22:

AGGCGCTTGG GAAATTCCAA CACC 24

(2) INFORMATION FOR SEQ ID NO:23:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:23:

AGGCATTCCT AAACCGGGAA CACC 24

(2) INFORMATION FOR SEQ ID NO:24:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:24:

AGGCACAATT CCTTCGGGAA CACC 24

(2) INFORMATION FOR SEQ ID NO:25:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:25:

GGTGTCGGGC TTCGGGAATA GCCT 24

(2) INFORMATION FOR SEQ ID NO:26:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

GGTGTTCCAA ACTCGGGAAT GCCT 24

(2) INFORMATION FOR SEQ ID NO:27:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:27:

GGTGTGGAAT CGGGAATTTA GCCT                                                                            24

( 2 ) INFORMATION FOR SEQ ID NO:28:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

AGGCTTATCG GGAAAACTTA CACC                                                                            24

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

GGTGTTCCAA ACGGGGGAAT GCCT                                                                            24

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

GGTGTGCAAT TCCAAGGAAT GCCT                                                                            24

( 2 ) INFORMATION FOR SEQ ID NO:31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

AGGCGCCATT CCAAGGATAA CACC                                                                            24

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

AGGCTAATCT TGGAATTCCA CACC                                                                            24

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TGGGACAAGA TTTCCA     16

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TGGGGAAGTG AAGGAGGGAG G     21

( 2 ) INFORMATION FOR SEQ ID NO:35:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

GAGGGGATC     10

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

GGTGTACGGT TGGGAATGCG GCCT     24

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GGTGTAGGAA TGGGAATACA GCCT     24

( 2 ) INFORMATION FOR SEQ ID NO:38:

( i ) SEQUENCE CHARACTERISTICS:
        ( A ) LENGTH: 24 base pairs (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:38:

GGTGTTGGGA TTGGGAATGT GCCT                                               24

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:39:

GGTGTCGGGA ATTATTTTAG GCCT                                               24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:40:

GGTGTAAAAA TGGGACAAA GCCT                                                24

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:41:

GGTGTGGGAA AGATATAGCC GCCT                                               24

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:42:

GGTGTTTAAC CAATTGGGAA GCCT                                               24

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:43:

GGTGTTCCGG TATTTGGGAA GCCT 24

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

GGTGTGGGAT AACTTGGGAA GCCT 24

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

AGGCGGGAAA ACCCATAGGA CACC 24

( 2 ) INFORMATION FOR SEQ ID NO:46:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

GGTGTAATCC GTCGGGAACA GCCTA 25

( 2 ) INFORMATION FOR SEQ ID NO:47:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

GGCTTTAGAT CAGGGAACAC ACC 23

( 2 ) INFORMATION FOR SEQ ID NO:48:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

GGTGTATCCT GGTAGGAATC GCCT 24

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

AGGCTATCCC AGGAATTTGA CACC        24

( 2 ) INFORMATION FOR SEQ ID NO:50:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

AGGCAAATTG TTCAGGAACA CACACC        26

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

GGTGTCCATA AGGAACAATA GCCT        24

( 2 ) INFORMATION FOR SEQ ID NO:52:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

AGGCAGACCC AAGGAAGCCA CACC        24

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

AGGCTATCCC AGGAATTTGA CACC        24

( 2 ) INFORMATION FOR SEQ ID NO:54:

( i ) SEQUENCE CHARACTERISTICS:
        ( A ) LENGTH: 23 base pairs (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:54:

AGGAGAATCC TATGGGATAC ACC 23

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:55:

GGTGTTCATT GGGATAGCAT GCCT 24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:56:

GGTGTTGGGA TTTCTGGATA GCCT 24

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:57:

AGGCGTTTGG GATGTATTTA CACC 24

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:58:

GGTGTGGGAT CGCCATATTC 20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:59:

GGTGTGGGAT TGCTTTATTT 20

( 2 ) INFORMATION FOR SEQ ID NO:60:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

GGTGTGGGAT TGGGACTAAA GCCTA 25

( 2 ) INFORMATION FOR SEQ ID NO:61:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

GGTGTGGGAT TGGGACTAAA GCCT 24

( 2 ) INFORMATION FOR SEQ ID NO:62:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

GGTGTAAGGA CAATGGGATA GCCT 24

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

GGTGTCAGGA TTTGGGACAC GCCT 24

( 2 ) INFORMATION FOR SEQ ID NO:64:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

GGTGTGGGAC TCAAAGAGGC 20

( 2 ) INFORMATION FOR SEQ ID NO:65:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:65:

GGTGTCCTCC AGCGGGATAA GCCT      24

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

AGGCATCCGG GATAATAAAA CACC      24

( 2 ) INFORMATION FOR SEQ ID NO:67:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:67:

GGTGTTCTTC GGGATGGCTT GCCT      24

( 2 ) INFORMATION FOR SEQ ID NO:68:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:68:

AGGCTTCACC GGGAGCACGA CACC      24

( 2 ) INFORMATION FOR SEQ ID NO:69:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:69:

GGTGTAGATC CCAGGGATTT GCCT      24

( 2 ) INFORMATION FOR SEQ ID NO:70:

( i ) SEQUENCE CHARACTERISTICS:
        ( A ) LENGTH: 24 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:70:

GGTGTAGGTA GGGACATCCC GCCT 24

(2) INFORMATION FOR SEQ ID NO:71:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:71:

GGTGTGAGAA ATAAGGGATA GCCT 24

(2) INFORMATION FOR SEQ ID NO:72:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:72:

CAAGGGAAT 9

(2) INFORMATION FOR SEQ ID NO:73:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:73:

TCAGCTTTTG GGAATGTATT CCCTGTCA 28

(2) INFORMATION FOR SEQ ID NO:74:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:74:

TCAGCTTTTG GGAATTCCCT GTCA 24

(2) INFORMATION FOR SEQ ID NO:75:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:75:

AGGCTTTTGG GAATACCAGA CACC 24

( 2 ) INFORMATION FOR SEQ ID NO:76:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:76:

AGGCTTGGGA TTGGGAATAA CACC 24

( 2 ) INFORMATION FOR SEQ ID NO:77:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:77:

GGTGTTCCTG GGAATGTTCG GCCTA 25

( 2 ) INFORMATION FOR SEQ ID NO:78:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

AGGCGTGGGA ATATCAGGAC ACC 23

( 2 ) INFORMATION FOR SEQ ID NO:79:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:79:

AGGCTGGGAA TGCTGGGAAA CACC 24

( 2 ) INFORMATION FOR SEQ ID NO:80:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:80:

GGTGTTGGGA ATGCTGGAAT GCCTA 25

( 2 ) INFORMATION FOR SEQ ID NO:81:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:81:

GGTGTAATTG GGAATTTTTA GCCTA    25

( 2 ) INFORMATION FOR SEQ ID NO:82:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:82:

GGTGTGGGAA AAGTGGGAAT GCCTA    25

( 2 ) INFORMATION FOR SEQ ID NO:83:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:83:

GGTGTTCCTG GGAATGCCAA GCCTA    25

( 2 ) INFORMATION FOR SEQ ID NO:84:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:84:

AGGCTACAGA ATACTGGGAA CACC    24

( 2 ) INFORMATION FOR SEQ ID NO:85:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:85:

AGGCTAAAAA TTCCTGGGAA CACC    24

( 2 ) INFORMATION FOR SEQ ID NO:86:

( i ) SEQUENCE CHARACTERISTICS:
        ( A ) LENGTH: 24 base pairs (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:86:

AGGCATTCCC GTTTTGGGAA CACC 24

(2) INFORMATION FOR SEQ ID NO:87:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:87:

AGGCATTCCC GTTTTGGGAA CACC 24

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:88:

GGTGTATCCC GGGAATACCG GCCTA 25

(2) INFORMATION FOR SEQ ID NO:89:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:89:

AGGCTAAGGA ATACCGGGAA CACC 24

(2) INFORMATION FOR SEQ ID NO:90:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:90:

AGGCTCTGGA ATATCGGGAA CACC 24

(2) INFORMATION FOR SEQ ID NO:91:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:91:

GGTGTAAATC GGGAATTCCG GCCTA                                                                                          2 5

( 2 ) INFORMATION FOR SEQ ID NO:92:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: cDNA ( x i ) SEQUENCE DESCRIPTION: SEQ ID NO:92:

AGGCCGGGAA TACCGGAAAA CACC                                                                                            2 4

( 2 ) INFORMATION FOR SEQ ID NO:93:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: cDNA ( x i ) SEQUENCE DESCRIPTION: SEQ ID NO:93:

AGGCAAAACA TTACAGGGAA CACC                                                                                            2 4

( 2 ) INFORMATION FOR SEQ ID NO:94:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: cDNA ( x i ) SEQUENCE DESCRIPTION: SEQ ID NO:94:

AGGCAGGGAA TATCGGGATA CACC                                                                                            2 4

( 2 ) INFORMATION FOR SEQ ID NO:95:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: cDNA ( x i ) SEQUENCE DESCRIPTION: SEQ ID NO:95:

GGTGTAGGAA TTCTAGGAAT GCCTA                                                                                           2 5

( 2 ) INFORMATION FOR SEQ ID NO:96:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: cDNA ( x i ) SEQUENCE DESCRIPTION: SEQ ID NO:96:

AGGCATTCCA AGGAATTTTA CACC                                                                                            2 4

( 2 ) INFORMATION FOR SEQ ID NO:97:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:97:

GGTGTAAGGA ATACTGGAAT GCCTA        25

( 2 ) INFORMATION FOR SEQ ID NO:98:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:98:

GGCAGAATTC CAAGGAATAC ACC        23

( 2 ) INFORMATION FOR SEQ ID NO:99:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:99:

AGGCCAAGGA ATATCAGGAA CACC        24

( 2 ) INFORMATION FOR SEQ ID NO:100:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:100:

TCAGCTTTTG GGAATCTCCT GTCA        24

( 2 ) INFORMATION FOR SEQ ID NO:101:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:101:

TCAGCTTTTG GGAATACCCT GTCA        24

( 2 ) INFORMATION FOR SEQ ID NO:102:

( i ) SEQUENCE CHARACTERISTICS:
        ( A ) LENGTH: 24 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:102:

TCAGCTTTTG GGAATCTCCT GTCA 24

(2) INFORMATION FOR SEQ ID NO:103:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:103:

TGGAGGGAAG TGGGAAACTT TT 22

(2) INFORMATION FOR SEQ ID NO:104:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:104:

TGGAAGTGGG AGGC 14

(2) INFORMATION FOR SEQ ID NO:105:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:105:

GAGGAGAAAG GTCTCCTAC 19

(2) INFORMATION FOR SEQ ID NO:106:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:106:

AACAGGGAAA CA 12

(2) INFORMATION FOR SEQ ID NO:107:

(i) SEQUENCE CHARACTERISTICS:
(A) LENGTH: 13 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:107:

GTCAGGGAAC AGG 13

( 2 ) INFORMATION FOR SEQ ID NO:108:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:108:

AAGGTGGGAA GTAA 14

( 2 ) INFORMATION FOR SEQ ID NO:109:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:109:

GGTAGGAATG G 11

( 2 ) INFORMATION FOR SEQ ID NO:110:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:110:

GGAGGGGAA GAA 13

( 2 ) INFORMATION FOR SEQ ID NO:111:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:111:

AGTGGGGAAA TCT 13

( 2 ) INFORMATION FOR SEQ ID NO:112:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:112:

GGTCAGGGAA ACAA 14

( 2 ) INFORMATION FOR SEQ ID NO:113:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:113:

TGGGGGAAGG GGTGGAAG                                                                                18

( 2 ) INFORMATION FOR SEQ ID NO:114:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:114:

TTTTGGGAAC C                                                                                       11

( 2 ) INFORMATION FOR SEQ ID NO:115:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:115:

AAAGGGAAC CC                                                                                       12

( 2 ) INFORMATION FOR SEQ ID NO:116:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:116:

TGGAGGGAG                                                                                          9

( 2 ) INFORMATION FOR SEQ ID NO:117:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:117:

AGGGGAAA                                                                                           8

( 2 ) INFORMATION FOR SEQ ID NO:118:

( i ) SEQUENCE CHARACTERISTICS:
        ( A ) LENGTH: 10 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:118:

TTTGGGAATT 10

(2) INFORMATION FOR SEQ ID NO:119:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:119:

TGAGAGGAAG AGGAGA 16

(2) INFORMATION FOR SEQ ID NO:120:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:120:

CAGGAATT 8

(2) INFORMATION FOR SEQ ID NO:121:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:121:

AAGGAAACCA AAACAGGGGA AG 22

(2) INFORMATION FOR SEQ ID NO:122:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:122:

TTGGAAACCT 10

(2) INFORMATION FOR SEQ ID NO:123:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA ( x i ) SEQUENCE DESCRIPTION: SEQ ID NO:123:

GTTTCCATGA CATCATGAAT GGGAGT 26

( 2 ) INFORMATION FOR SEQ ID NO:124:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:124:

GTTTCCATGA TGTCATGAAT GGGGGT 26

( 2 ) INFORMATION FOR SEQ ID NO:125:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:125:

TTCTTGGGGA TTG 13

( 2 ) INFORMATION FOR SEQ ID NO:126:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:126:

GGAGGAACT 9

( 2 ) INFORMATION FOR SEQ ID NO:127:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:127:

TTTGGGATG 9

( 2 ) INFORMATION FOR SEQ ID NO:128:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:128:

TTCTAGGAAG TAAGGGAATT T 21

( 2 ) INFORMATION FOR SEQ ID NO:129:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:129:

GTGGGAAGA         9

( 2 ) INFORMATION FOR SEQ ID NO:130:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:130:

TAGGAATTCT         10

( 2 ) INFORMATION FOR SEQ ID NO:131:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:131:

TAAGGAAAGG         10

( 2 ) INFORMATION FOR SEQ ID NO:132:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:132:

TTTCCAAGTG GGAATC         16

( 2 ) INFORMATION FOR SEQ ID NO:133:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:133:

TGGGGAGTT         9

( 2 ) INFORMATION FOR SEQ ID NO:134:

( i ) SEQUENCE CHARACTERISTICS:
        ( A ) LENGTH: 11 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:134:

TTGGGAAGGA T   11

(2) INFORMATION FOR SEQ ID NO:135:

(i) SEQUENCE CHARACTERISTICS:
(A) LENGTH: 8 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:135:

AAGGAACA   8

(2) INFORMATION FOR SEQ ID NO:136:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:136:

CAGGGGAATC TCCCTCTCCA T   21

(2) INFORMATION FOR SEQ ID NO:137:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:137:

AAGAGGAAAA   10

(2) INFORMATION FOR SEQ ID NO:138:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:138:

GGGAAATTCC   10

(2) INFORMATION FOR SEQ ID NO:139:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:139:

GGGGAATCCC     10

( 2 ) INFORMATION FOR SEQ ID NO:140:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:140:

TGGGAG     6

( 2 ) INFORMATION FOR SEQ ID NO:141:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:141:

CAGGGAAGTA     10

( 2 ) INFORMATION FOR SEQ ID NO:142:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:142:

CAAGGGACTT TCCGCTGGGG ACTTTCCAGG GAGGCG     36

( 2 ) INFORMATION FOR SEQ ID NO:143:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:143:

TTTGGTTATA AATGTATTGA TTGCATCCCC ATTACCCAGA AGGCCAATAT TTAATTGGAG     60

TCTTAACTCA ATTGTGTTTT CGTCAGTTGG TAAGCCTCAC AAA     103

( 2 ) INFORMATION FOR SEQ ID NO:144:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:144:

ATGGGCCTTC CGGGCATGTA CCCAGGTAAG CACTGAGGCC CTGCTGAGCT GCACCCCTCC       60

CCCTCCCAGC GCCTGGGCCA GGATGGGGCT CTGTGGCCTG TTTCAGCCAC AGGAGG          116

( 2 ) INFORMATION FOR SEQ ID NO:145:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:145:

CCTTGTTGCT GCTGTGTTGC TATCTTGTGA CTTATTTTTG CAGTGACACT GAGTGGCCTC       60

CTGTGTTGTC TCTTTCAGCC AGTAATGTTA AAGT                                  94

( 2 ) INFORMATION FOR SEQ ID NO:146:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:146:

GAGCCCTGGC AGATGTGTCC TGTCTGCTGT GACACTAGAA CACCATTCAA CCCCTGGGTG       60

TAGATTTCAC TTATGACCAT CTACTTCCCG CAGGAGACAA GTGCCTGTCA GACATGCCCT     120

( 2 ) INFORMATION FOR SEQ ID NO:147:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:147:

ACATGTGTGG TTATCACAGC CAGGACAGGT ACGAGTTCTC ATCCCATATC ACGCGGGGGG       60

AGCATCGTTA CCACCTGAGC TAAACCCAGC CAGGCCCCAC TGAAGCACAA AGATAGCTGG     120

( 2 ) INFORMATION FOR SEQ ID NO:148:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:148:

AGGAGGAAAA                                                             10

( 2 ) INFORMATION FOR SEQ ID NO:149:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:149:

TGGGAAT                                                                                                                         7

( 2 ) INFORMATION FOR SEQ ID NO:150:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:150:

TCAGCTTTTG GGAATCTCCT GTCA                                                                                                      24

( 2 ) INFORMATION FOR SEQ ID NO:151:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:151:

TCAGCTTTTG GGATTCCTCT CA                                                                                                        22

( 2 ) INFORMATION FOR SEQ ID NO:152:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:152:

TCAGCGGGGG GGAATACCCT GTCA                                                                                                      24

( 2 ) INFORMATION FOR SEQ ID NO:153:

( i ) SEQUENCE CHARACTERISTICS:
        ( A ) LENGTH: 470 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: C-terminal ( x i ) SEQUENCE DESCRIPTION: SEQ ID NO:153:

```
Xaa  Xaa  Ala  Ser  Asn  Val  Lys  Val  Glu  Thr  Gln  Ser  Asp  Glu  Glu  Asn
 1              5                        10                       15

Gly  Arg  Ala  Cys  Glu  Met  Asn  Gly  Glu  Glu  Cys  Ala  Glu  Asp  Leu  Arg
              20                        25                       30

Met  Leu  Asp  Ala  Ser  Gly  Glu  Lys  Met  Asn  Gly  Ser  His  Arg  Asp  Gln
              35                        40                       45

Gly  Ser  Ser  Ala  Leu  Ser  Gly  Val  Gly  Gly  Ile  Arg  Leu  Pro  Asn  Gly
         50                        55                       60

Lys  Leu  Lys  Cys  Asp  Ile  Cys  Gly  Ile  Xaa  Cys  Ile  Gly  Pro  Asn  Val
 65                       70                        75                       80
```

-continued

| | | | | | | | | | | | | | | |
|---|---|---|---|---|---|---|---|---|---|---|---|---|---|---|
| Leu | Met | Val | His | Lys 85 | Arg | Ser | His | Thr 90 | Gly | Glu | Arg | Pro | Phe | Gln Cys 95 |
| Asn | Gln | Cys | Gly 100 | Ala | Ser | Phe | Thr | Gln 105 | Lys | Gly | Asn | Leu | Leu 110 | Arg His |
| Ile | Lys | Leu 115 | His | Ser | Gly | Glu | Lys 120 | Pro | Phe | Lys | Cys | His 125 | Leu | Cys Asn |
| Tyr | Ala 130 | Cys | Arg | Arg | Arg | Asp 135 | Ala | Leu | Thr | Gly | His 140 | Leu | Arg | Thr His |
| Ser 145 | Val | Gly | Lys | Pro | His 150 | Lys | Cys | Gly | Tyr | Cys 155 | Gly | Arg | Ser | Tyr Lys 160 |
| Gln | Arg | Xaa | Ser | Leu 165 | Glu | Glu | His | Lys | Glu 170 | Arg | Cys | His | Asn | Tyr Leu 175 |
| Glu | Ser | Met | Gly 180 | Leu | Pro | Gly | Xaa | Xaa 185 | Xaa | Pro | Val | Ile | Lys 190 | Glu Glu |
| Thr | Xaa | His 195 | Xaa | Glu | Met | Ala | Glu 200 | Asp | Leu | Cys | Lys | Ile 205 | Gly | Xaa Glu |
| Arg | Ser 210 | Leu | Val | Leu | Asp | Arg 215 | Leu | Ala | Ser | Asn | Val 220 | Ala | Lys | Arg Lys |
| Ser 225 | Ser | Met | Pro | Gln | Lys 230 | Phe | Leu | Gly | Asp | Lys 235 | Xaa | Leu | Ser | Asp Xaa 240 |
| Pro | Tyr | Asp | Ser | Ala 245 | Xaa | Tyr | Glu | Lys | Glu 250 | Xaa | Xaa | Met | Met | Xaa Ser 255 |
| His | Val | Met | Asp 260 | Xaa | Ala | Ile | Asn | Asn 265 | Ala | Ile | Asn | Tyr | Leu 270 | Gly Ala |
| Glu | Ser | Leu 275 | Arg | Pro | Leu | Val | Gln 280 | Thr | Pro | Pro | Gly | Xaa 285 | Ser | Glu Val |
| Val | Pro 290 | Val | Ile | Ser | Pro | Met 295 | Tyr | Gln | Leu | His | Xaa 300 | Xaa | Xaa | Ser Xaa |
| Gly 305 | Xaa | Pro | Arg | Ser | Asn 310 | His | Ser | Ala | Gln | Asp 315 | Xaa | Ala | Val | Xaa Xaa 320 |
| Leu | Leu | Leu | Leu | Ser 325 | Lys | Ala | Lys | Xaa | Val 330 | Xaa | Ser | Glu | Arg | Glu Ala 335 |
| Ser | Pro | Ser | Asn 340 | Ser | Cys | Gln | Asp | Ser 345 | Thr | Asp | Thr | Glu | Ser 350 | Asn Xaa |
| Glu | Glu | Gln 355 | Arg | Ser | Gly | Leu | Ile 360 | Tyr | Leu | Thr | Asn | His 365 | Ile | Xaa Xaa |
| Xaa | Ala 370 | Xaa | Xaa | Xaa | Xaa | Xaa 375 | Leu | Lys | Glu | Glu | Xaa 380 | Arg | Ala | Tyr Xaa |
| Xaa 385 | Leu | Arg | Ala | Ala | Ser 390 | Glu | Asn | Ser | Gln | Asp 395 | Ala | Xaa | Arg | Val Val 400 |
| Ser | Thr | Ser | Gly | Glu 405 | Gln | Xaa | Lys | Val | Tyr 410 | Lys | Cys | Glu | His | Cys Arg 415 |
| Val | Leu | Phe | Leu 420 | Asp | His | Val | Met | Tyr 425 | Thr | Ile | His | Met | Xaa 430 | Xaa Xaa |
| Gly | Cys | His 435 | Gly | Phe | Arg | Asp | Pro 440 | Phe | Glu | Cys | Asn | Met 445 | Cys | Gly Tyr |
| His | Ser | Gln 450 | Asp | Arg | Tyr | Glu | Phe 455 | Ser | Ser | His | Ile 460 | Thr | Arg | Gly Glu |
| His 465 | Arg | Xaa | His | Xaa | Ser 470 | | | | | | | | | |

(2) INFORMATION FOR SEQ ID NO:154:

(i) SEQUENCE CHARACTERISTICS:
    (A) LENGTH: 38 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:154:

AGAAGTTTCC ATAAGATGAT GAATGGGGGT GGCAGAGA 38

( 2 ) INFORMATION FOR SEQ ID NO:155:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:155:

NNHTGGGAAT DYY 13

( 2 ) INFORMATION FOR SEQ ID NO:156:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:156:

NNYYGGGAAT HNC 13

( 2 ) INFORMATION FOR SEQ ID NO:157:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:157:

TMYGGGAATD YY 12

( 2 ) INFORMATION FOR SEQ ID NO:158:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:158:

TCAGCTTTTG AGAATACCCT GTCA 24

( 2 ) INFORMATION FOR SEQ ID NO:159:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:159:

TCAGCTTTTG GGATTACCCT GTCA 24

( 2 ) INFORMATION FOR SEQ ID NO:160:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:160:

TCAGCTTTTG GGAAAAACCT GTCA 24

( 2 ) INFORMATION FOR SEQ ID NO:161:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:161:

GTTTCCATGA CATCATGATG GGGGT 25

( 2 ) INFORMATION FOR SEQ ID NO:162:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:162:

TGGGAATACC 10

( 2 ) INFORMATION FOR SEQ ID NO:163:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:163:

GGCTGCCACG GCTTCCGTGA TCCT 24

( 2 ) INFORMATION FOR SEQ ID NO:164:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:164:

AGCGGTCTGG GGAAACATCT AGGA 24

( 2 ) INFORMATION FOR SEQ ID NO:165:

( i ) SEQUENCE CHARACTERISTICS:
        ( A ) LENGTH: 708 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..708

( x i ) SEQUENCE DESCRIPTION: SEQ ID NO:165:

```
GGA  GAC  AAG  TGC  CTG  TCA  GAC  ATG  CCC  TAT  GAC  AGT  GCC  AAC  TAT  GAG      48
Gly  Asp  Lys  Cys  Leu  Ser  Asp  Met  Pro  Tyr  Asp  Ser  Ala  Asn  Tyr  Glu
 1              5                   10                  15

AAG  GAG  GAT  ATG  ATG  ACA  TCC  CAC  GTG  ATG  GAC  CAG  GCC  ATC  AAC  AAT      96
Lys  Glu  Asp  Met  Met  Thr  Ser  His  Val  Met  Asp  Gln  Ala  Ile  Asn  Asn
                 20                  25                  30

GCC  ATC  AAC  TAC  CTG  GGG  GCT  GAG  TCC  CTG  CGC  CCA  TTG  GTG  CAG  ACA     144
Ala  Ile  Asn  Tyr  Leu  Gly  Ala  Glu  Ser  Leu  Arg  Pro  Leu  Val  Gln  Thr
           35                  40                  45

CCC  CCC  GGT  AGC  TCC  GAG  GTG  GTG  CCA  GTC  ATC  AGC  TCC  ATG  TAC  CAG     192
Pro  Pro  Gly  Ser  Ser  Glu  Val  Val  Pro  Val  Ile  Ser  Ser  Met  Tyr  Gln
      50                  55                  60

CTG  CAC  AAG  CCC  CCC  TCA  GAT  GGC  CCC  CCA  CGG  TCC  AAC  CAT  TCA  GCA     240
Leu  His  Lys  Pro  Pro  Ser  Asp  Gly  Pro  Pro  Arg  Ser  Asn  His  Ser  Ala
 65                  70                  75                  80

CAG  GAC  GCC  GTG  GAT  AAC  TTG  CTG  CTG  CTG  TCC  AAG  GCC  AAG  TCT  GTG     288
Gln  Asp  Ala  Val  Asp  Asn  Leu  Leu  Leu  Leu  Ser  Lys  Ala  Lys  Ser  Val
                 85                  90                  95

TCA  TCG  GAG  CGA  GAG  GCC  TCC  CCG  AGC  AAC  AGC  TGC  CAA  GAC  TCC  ACA     336
Ser  Ser  Glu  Arg  Glu  Ala  Ser  Pro  Ser  Asn  Ser  Cys  Gln  Asp  Ser  Thr
           100                 105                 110

GAT  ACA  GAG  AGC  AAC  GCG  GAG  GAA  CAG  CGC  AGC  GGC  CTT  ATC  TAC  CTA     384
Asp  Thr  Glu  Ser  Asn  Ala  Glu  Glu  Gln  Arg  Ser  Gly  Leu  Ile  Tyr  Leu
      115                 120                 125

ACC  AAC  CAC  ATC  AAC  CCG  CAT  GCA  CGC  AAT  GGG  CTG  GCT  CTC  AAG  GAG     432
Thr  Asn  His  Ile  Asn  Pro  His  Ala  Arg  Asn  Gly  Leu  Ala  Leu  Lys  Glu
 130                 135                 140

GAG  CAG  CGC  GCC  TAC  GAG  GTG  CTG  AGG  GCG  GCC  TCA  GAG  AAC  TCG  CAG     480
Glu  Gln  Arg  Ala  Tyr  Glu  Val  Leu  Arg  Ala  Ala  Ser  Glu  Asn  Ser  Gln
145                  150                 155                 160

GAT  GCC  TTC  CGT  GTG  GTC  AGC  ACG  AGT  GGC  GAG  CAG  CTG  AAG  GTG  TAC     528
Asp  Ala  Phe  Arg  Val  Val  Ser  Thr  Ser  Gly  Glu  Gln  Leu  Lys  Val  Tyr
                 165                 170                 175

AAG  TGC  GAA  CAC  TGC  CGC  GTG  CTC  TTC  CTG  GAT  CAC  GTC  ATG  TAT  ACC     576
Lys  Cys  Glu  His  Cys  Arg  Val  Leu  Phe  Leu  Asp  His  Val  Met  Tyr  Thr
           180                 185                 190

ATT  CAC  ATG  GGC  TGC  CAT  GGC  TGC  CAT  GGC  TTT  CGG  GAT  CCC  TTT  GAG     624
Ile  His  Met  Gly  Cys  His  Gly  Cys  His  Gly  Phe  Arg  Asp  Pro  Phe  Glu
      195                 200                 205

TGT  AAC  ATG  TGT  GGT  TAT  CAC  AGC  CAG  GAC  AGG  TAC  GAG  TTC  TCA  TCC     672
Cys  Asn  Met  Cys  Gly  Tyr  His  Ser  Gln  Asp  Arg  Tyr  Glu  Phe  Ser  Ser
 210                 215                 220

CAT  ATC  ACG  CGG  GGG  GAG  CAT  CGT  TAC  CAC  CTG  AGC                        708
His  Ile  Thr  Arg  Gly  Glu  His  Arg  Tyr  His  Leu  Ser
 225                 230                 235
```

( 2 ) INFORMATION FOR SEQ ID NO:166:

( i ) SEQUENCE CHARACTERISTICS:
  ( A ) LENGTH: 236 amino acids
  ( B ) TYPE: amino acid
  ( D ) TOPOLOGY: linear ( i i ) MOLECULE TYPE: protein ( x i ) SEQUENCE DESCRIPTION: SEQ ID NO:166:

| Gly | Asp | Lys | Cys | Leu | Ser | Asp | Met | Pro | Tyr | Asp | Ser | Ala | Asn | Tyr | Glu |
|---|---|---|---|---|---|---|---|---|---|---|---|---|---|---|---|
| 1 | | | | 5 | | | | | 10 | | | | | 15 | |

| Lys | Glu | Asp | Met | Met | Thr | Ser | His | Val | Met | Asp | Gln | Ala | Ile | Asn | Asn |
|---|---|---|---|---|---|---|---|---|---|---|---|---|---|---|---|
| | | | 20 | | | | | 25 | | | | | 30 | | |

| Ala | Ile | Asn | Tyr | Leu | Gly | Ala | Glu | Ser | Leu | Arg | Pro | Leu | Val | Gln | Thr |
|---|---|---|---|---|---|---|---|---|---|---|---|---|---|---|---|
| | | 35 | | | | | 40 | | | | | 45 | | | |

| Pro | Pro | Gly | Ser | Ser | Glu | Val | Val | Pro | Val | Ile | Ser | Ser | Met | Tyr | Gln |
|---|---|---|---|---|---|---|---|---|---|---|---|---|---|---|---|
| | 50 | | | | | 55 | | | | | | 60 | | | |

| Leu | His | Lys | Pro | Pro | Ser | Asp | Gly | Pro | Pro | Arg | Ser | Asn | His | Ser | Ala |
|---|---|---|---|---|---|---|---|---|---|---|---|---|---|---|---|
| 65 | | | | | 70 | | | | | 75 | | | | | 80 |

| Gln | Asp | Ala | Val | Asp | Asn | Leu | Leu | Leu | Leu | Ser | Lys | Ala | Lys | Ser | Val |
|---|---|---|---|---|---|---|---|---|---|---|---|---|---|---|---|
| | | | | 85 | | | | | 90 | | | | | 95 | |

| Ser | Ser | Glu | Arg | Glu | Ala | Ser | Pro | Ser | Asn | Ser | Cys | Gln | Asp | Ser | Thr |
|---|---|---|---|---|---|---|---|---|---|---|---|---|---|---|---|
| | | | 100 | | | | | 105 | | | | | 110 | | |

| Asp | Thr | Glu | Ser | Asn | Ala | Glu | Gln | Arg | Ser | Gly | Leu | Ile | Tyr | Leu |
|---|---|---|---|---|---|---|---|---|---|---|---|---|---|---|
| | | 115 | | | | | 120 | | | | | 125 | | |

| Thr | Asn | His | Ile | Asn | Pro | His | Ala | Arg | Asn | Gly | Leu | Ala | Leu | Lys | Glu |
|---|---|---|---|---|---|---|---|---|---|---|---|---|---|---|---|
| | 130 | | | | | 135 | | | | | 140 | | | | |

| Glu | Gln | Arg | Ala | Tyr | Glu | Val | Leu | Arg | Ala | Ala | Ser | Glu | Asn | Ser | Gln |
|---|---|---|---|---|---|---|---|---|---|---|---|---|---|---|---|
| 145 | | | | | 150 | | | | | 155 | | | | | 160 |

| Asp | Ala | Phe | Arg | Val | Val | Ser | Thr | Ser | Gly | Glu | Gln | Leu | Lys | Val | Tyr |
|---|---|---|---|---|---|---|---|---|---|---|---|---|---|---|---|
| | | | | 165 | | | | | 170 | | | | | 175 | |

| Lys | Cys | Glu | His | Cys | Arg | Val | Leu | Phe | Leu | Asp | His | Val | Met | Tyr | Thr |
|---|---|---|---|---|---|---|---|---|---|---|---|---|---|---|---|
| | | | 180 | | | | | 185 | | | | | 190 | | |

| Ile | His | Met | Gly | Cys | His | Gly | Cys | His | Gly | Phe | Arg | Asp | Pro | Phe | Glu |
|---|---|---|---|---|---|---|---|---|---|---|---|---|---|---|---|
| | | 195 | | | | | 200 | | | | | 205 | | | |

| Cys | Asn | Met | Cys | Gly | Tyr | His | Ser | Gln | Asp | Arg | Tyr | Glu | Phe | Ser | Ser |
|---|---|---|---|---|---|---|---|---|---|---|---|---|---|---|---|
| | 210 | | | | | 215 | | | | | 220 | | | | |

| His | Ile | Thr | Arg | Gly | Glu | His | Arg | Tyr | His | Leu | Ser |
|---|---|---|---|---|---|---|---|---|---|---|---|
| 225 | | | | | 230 | | | | | 235 | |

( 2 ) INFORMATION FOR SEQ ID NO:167:

( i ) SEQUENCE CHARACTERISTICS:
    ( A ) LENGTH: 714 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..710

( x i ) SEQUENCE DESCRIPTION: SEQ ID NO:167:

| GGG | GAC | AAG | GGC | CTG | TCC | GAC | ACG | CCC | TAC | GAC | AGT | GCC | ACG | TAC | GAG | 48 |
|---|---|---|---|---|---|---|---|---|---|---|---|---|---|---|---|---|
| Gly | Asp | Lys | Gly | Leu | Ser | Asp | Thr | Pro | Tyr | Asp | Ser | Ala | Thr | Tyr | Glu | |
| 1 | | | | 5 | | | | | 10 | | | | | 15 | | |

| AAG | GAG | AAC | GAA | ATG | ATG | AAG | TCC | CAC | GTG | ATG | GAC | CAA | GCC | ATC | AAC | 96 |
|---|---|---|---|---|---|---|---|---|---|---|---|---|---|---|---|---|
| Lys | Glu | Asn | Glu | Met | Met | Lys | Ser | His | Val | Met | Asp | Gln | Ala | Ile | Asn | |
| | | | 20 | | | | | 25 | | | | | 30 | | | |

| AAC | GCC | ATC | AAC | TAC | CTG | GGG | GCC | GAG | TCC | CTG | CGC | CCG | CTG | GTG | CAG | 144 |

| | | | | | | | | | | | | | | | |
|---|---|---|---|---|---|---|---|---|---|---|---|---|---|---|---|
|Asn|Ala|Ile|Asn|Tyr|Leu|Gly|Ala|Glu|Ser|Leu|Arg|Pro|Leu|Val|Gln|
| | |35| | | | |40| | | |45| | | | |

| | | | | | | | | | | | | | | | | |
|---|---|---|---|---|---|---|---|---|---|---|---|---|---|---|---|---|
|ACG|CCC|CCG|GGC|GGT|TCC|GAG|GTG|GTC|CCG|GTC|ATC|AGC|CCG|ATG|TAC|192|
|Thr|Pro|Pro|Gly|Gly|Ser|Glu|Val|Val|Pro|Val|Ile|Ser|Pro|Met|Tyr| |
| |50| | | | |55| | | |60| | | | | | |

| | | | | | | | | | | | | | | | | |
|---|---|---|---|---|---|---|---|---|---|---|---|---|---|---|---|---|
|CAG|CTG|CAC|AGG|CGC|TCG|GAG|GGC|ACC|CCG|CGC|TCC|AAC|CAC|TCG|GCC|240|
|Gln|Leu|His|Arg|Arg|Ser|Glu|Gly|Thr|Pro|Arg|Ser|Asn|His|Ser|Ala| |
|65| | | | |70| | | |75| | | | |80| | |

| | | | | | | | | | | | | | | | | |
|---|---|---|---|---|---|---|---|---|---|---|---|---|---|---|---|---|
|CAG|GAC|AGC|GCC|GTG|GAG|TAC|CTG|CTG|CTG|CTC|TCC|AAG|GCC|AAG|TTG|288|
|Gln|Asp|Ser|Ala|Val|Glu|Tyr|Leu|Leu|Leu|Leu|Ser|Lys|Ala|Lys|Leu| |
| | | | |85| | | | |90| | | | |95| | |

| | | | | | | | | | | | | | | | | |
|---|---|---|---|---|---|---|---|---|---|---|---|---|---|---|---|---|
|GAA|AAA|AAA|AAA|GTG|CCC|TCG|GAG|CGC|GAG|GCG|TCC|CCG|AGC|AAC|AGC|336|
|Glu|Lys|Lys|Lys|Val|Pro|Ser|Glu|Arg|Glu|Ala|Ser|Pro|Ser|Asn|Ser| |
| | | |100| | | |105| | | |110| | | | | |

| | | | | | | | | | | | | | | | | |
|---|---|---|---|---|---|---|---|---|---|---|---|---|---|---|---|---|
|TGC|CAA|GAC|TCC|ACG|GAC|ACC|GAG|AGC|AAC|AAC|GAG|GAG|CAG|CGC|AGC|384|
|Cys|Gln|Asp|Ser|Thr|Asp|Thr|Glu|Ser|Asn|Asn|Glu|Glu|Gln|Arg|Ser| |
| | |115| | | |120| | | |125| | | | | | |

| | | | | | | | | | | | | | | | | |
|---|---|---|---|---|---|---|---|---|---|---|---|---|---|---|---|---|
|GGT|CTT|ATC|TAC|CTG|ACC|AAC|CAC|ATC|GCC|CGA|CGC|GCG|CAA|CGC|GTG|432|
|Gly|Leu|Ile|Tyr|Leu|Thr|Asn|His|Ile|Ala|Arg|Arg|Ala|Gln|Arg|Val| |
| |130| | | | |135| | | |140| | | | | | |

| | | | | | | | | | | | | | | | | |
|---|---|---|---|---|---|---|---|---|---|---|---|---|---|---|---|---|
|TCG|CTC|AAG|GAG|GAG|CAC|CGC|GCC|TAC|GAC|CTG|CTG|CGC|GCC|GCC|TCC|480|
|Ser|Leu|Lys|Glu|Glu|His|Arg|Ala|Tyr|Asp|Leu|Leu|Arg|Ala|Ala|Ser| |
|145| | | | |150| | | |155| | | | |160| | |

| | | | | | | | | | | | | | | | | |
|---|---|---|---|---|---|---|---|---|---|---|---|---|---|---|---|---|
|GAG|AAC|TCG|CAG|GAC|GCG|CTC|CGC|GTG|GTC|AGC|ACC|AGC|GGG|GAG|CAG|528|
|Glu|Asn|Ser|Gln|Asp|Ala|Leu|Arg|Val|Val|Ser|Thr|Ser|Gly|Glu|Gln| |
| | | | |165| | | | |170| | | | |175| | |

| | | | | | | | | | | | | | | | | |
|---|---|---|---|---|---|---|---|---|---|---|---|---|---|---|---|---|
|ATG|AAG|GTG|TAC|AAG|TGC|GAA|CAC|TGC|CGG|GTG|CTC|TTC|CTG|GAT|CAC|576|
|Met|Lys|Val|Tyr|Lys|Cys|Glu|His|Cys|Arg|Val|Leu|Phe|Leu|Asp|His| |
| | | |180| | | | |185| | | | |190| | | |

| | | | | | | | | | | | | | | | | |
|---|---|---|---|---|---|---|---|---|---|---|---|---|---|---|---|---|
|GTC|ATG|TAC|ACC|ATC|CAC|ATG|GGC|TGC|CAC|GGC|TTC|CGT|GAT|CCT|TTT|624|
|Val|Met|Tyr|Thr|Ile|His|Met|Gly|Cys|His|Gly|Phe|Arg|Asp|Pro|Phe| |
| | |195| | | | |200| | | |205| | | | | |

| | | | | | | | | | | | | | | | | |
|---|---|---|---|---|---|---|---|---|---|---|---|---|---|---|---|---|
|GAG|TGC|AAC|ATG|TGC|GGC|TAC|CAC|AGC|CAG|GAC|CGG|TAC|GAG|TTC|TCG|672|
|Glu|Cys|Asn|Met|Cys|Gly|Tyr|His|Ser|Gln|Asp|Arg|Tyr|Glu|Phe|Ser| |
| |210| | | | |215| | | |220| | | | | | |

| | | | | | | | | | | | |
|---|---|---|---|---|---|---|---|---|---|---|---|
|TCG|CAC|ATA|ACG|CGA|GGG|GAG|CAC|CGC|TTC|CAC|ATG|AGC|TAA| | |714|
|Ser|His|Ile|Thr|Arg|Gly|Glu|His|Arg|Phe|His|Met|Ser| | | | |
|225| | | | |230| | | | |235| | | | | | |

( 2 ) INFORMATION FOR SEQ ID NO:168:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:168:

| | | | | | | | | | | | | | | | |
|---|---|---|---|---|---|---|---|---|---|---|---|---|---|---|---|
|Gly|Asp|Lys|Gly|Leu|Ser|Asp|Thr|Pro|Tyr|Asp|Ser|Ala|Thr|Tyr|Glu|
|1| | | |5| | | | |10| | | | |15| |

| | | | | | | | | | | | | | | | |
|---|---|---|---|---|---|---|---|---|---|---|---|---|---|---|---|
|Lys|Glu|Asn|Glu|Met|Met|Lys|Ser|His|Val|Met|Asp|Gln|Ala|Ile|Asn|
| | | |20| | | | |25| | | | |30| | |

| | | | | | | | | | | | | | | | |
|---|---|---|---|---|---|---|---|---|---|---|---|---|---|---|---|
|Asn|Ala|Ile|Asn|Tyr|Leu|Gly|Ala|Glu|Ser|Leu|Arg|Pro|Leu|Val|Gln|
| | |35| | | | |40| | | |45| | | | |

| | | | | | | | | | | | | | | | |
|---|---|---|---|---|---|---|---|---|---|---|---|---|---|---|---|
|Thr|Pro|Pro|Gly|Gly|Ser|Glu|Val|Val|Pro|Val|Ile|Ser|Pro|Met|Tyr|
| |50| | | | |55| | | |60| | | | | |

| | | | | | | | | | | | | | | | |
|---|---|---|---|---|---|---|---|---|---|---|---|---|---|---|---|
|Gln|Leu|His|Arg|Arg|Ser|Glu|Gly|Thr|Pro|Arg|Ser|Asn|His|Ser|Ala|
|65| | | | |70| | | |75| | | | |80| |

| | | | | | | | | | | | | | | | |
|---|---|---|---|---|---|---|---|---|---|---|---|---|---|---|---|
|Gln|Asp|Ser|Ala|Val|Glu|Tyr|Leu|Leu|Leu|Leu|Ser|Lys|Ala|Lys|Leu|
| | | | |85| | | | |90| | | | |95| |

```
Glu  Lys  Lys  Lys  Val  Pro  Ser  Glu  Arg  Glu  Ala  Ser  Pro  Ser  Asn  Ser
               100                 105                      110

Cys  Gln  Asp  Ser  Thr  Asp  Thr  Glu  Ser  Asn  Asn  Glu  Glu  Gln  Arg  Ser
               115                 120                      125

Gly  Leu  Ile  Tyr  Leu  Thr  Asn  His  Ile  Ala  Arg  Arg  Ala  Gln  Arg  Val
     130                      135                      140

Ser  Leu  Lys  Glu  Glu  His  Arg  Ala  Tyr  Asp  Leu  Leu  Arg  Ala  Ala  Ser
145                      150                      155                           160

Glu  Asn  Ser  Gln  Asp  Ala  Leu  Arg  Val  Val  Ser  Thr  Ser  Gly  Glu  Gln
               165                      170                      175

Met  Lys  Val  Tyr  Lys  Cys  Glu  His  Cys  Arg  Val  Leu  Phe  Leu  Asp  His
               180                      185                      190

Val  Met  Tyr  Thr  Ile  His  Met  Gly  Cys  His  Gly  Phe  Arg  Asp  Pro  Phe
               195                      200                      205

Glu  Cys  Asn  Met  Cys  Gly  Tyr  His  Ser  Gln  Asp  Arg  Tyr  Glu  Phe  Ser
     210                      215                      220

Ser  His  Ile  Thr  Arg  Gly  Glu  His  Arg  Phe  His  Met
225                      230                      235
```

( 2 ) INFORMATION FOR SEQ ID NO:169:

( i ) SEQUENCE CHARACTERISTICS:
        ( A ) LENGTH: 238 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:169:

```
Gly  Asp  Lys  Xaa  Leu  Ser  Asp  Xaa  Pro  Tyr  Asp  Ser  Ala  Xaa  Tyr  Glu
1                    5                        10                      15

Lys  Glu  Xaa  Xaa  Met  Met  Xaa  Ser  His  Val  Met  Asp  Xaa  Ala  Ile  Asn
               20                      25                      30

Asn  Ala  Ile  Asn  Tyr  Leu  Gly  Ala  Glu  Ser  Leu  Arg  Pro  Leu  Val  Gln
          35                      40                      45

Thr  Pro  Pro  Gly  Xaa  Ser  Glu  Val  Val  Pro  Val  Ile  Ser  Pro  Met  Tyr
     50                      55                      60

Gln  Leu  His  Xaa  Xaa  Xaa  Ser  Xaa  Gly  Xaa  Pro  Arg  Ser  Asn  His  Ser
65                       70                      75                           80

Ala  Gln  Asp  Xaa  Ala  Val  Xaa  Xaa  Leu  Leu  Leu  Leu  Ser  Lys  Ala  Lys
               85                      90                      95

Xaa  Val  Xaa  Ser  Glu  Arg  Glu  Ala  Ser  Pro  Ser  Asn  Ser  Cys  Gln  Asp
               100                     105                     110

Ser  Thr  Asp  Thr  Glu  Ser  Asn  Xaa  Glu  Glu  Gln  Arg  Ser  Gly  Leu  Ile
               115                     120                     125

Tyr  Leu  Thr  Asn  His  Ile  Xaa  Xaa  Xaa  Ala  Xaa  Xaa  Xaa  Xaa  Xaa  Leu
     130                      135                     140

Lys  Glu  Glu  Xaa  Arg  Ala  Tyr  Xaa  Xaa  Leu  Arg  Ala  Ala  Ser  Glu  Asn
145                      150                     155                           160

Ser  Gln  Asp  Ala  Xaa  Arg  Val  Val  Ser  Thr  Ser  Gly  Glu  Gln  Xaa  Lys
               165                     170                          175

Val  Tyr  Lys  Cys  Glu  His  Cys  Arg  Val  Leu  Phe  Leu  Asp  His  Val  Met
               180                     185                     190

Tyr  Thr  Ile  His  Met  Xaa  Xaa  Xaa  Gly  Cys  His  Gly  Phe  Arg  Asp  Pro
               195                     200                     205
```

```
            Phe  Glu  Cys  Asn  Met  Cys  Gly  Tyr  His  Ser  Gln  Asp  Arg  Tyr  Glu  Phe
                 210                215                 220

Ser  Ser  His  Ile  Thr  Arg  Gly  Glu  His  Arg  Xaa  His  Xaa  Ser
            225                 230                 235
```

( 2 ) INFORMATION FOR SEQ ID NO:170:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..135

( x i ) SEQUENCE DESCRIPTION: SEQ ID NO:170:

```
GTC  ATT  AAG  GAA  GAA  ACT  AAC  CAC  AAC  GAG  ATG  GCA  GAA  GAC  CTG  TGC          48
Val  Ile  Lys  Glu  Glu  Thr  Asn  His  Asn  Glu  Met  Ala  Glu  Asp  Leu  Cys
 1              5                        10                       15

AAG  ATA  GGA  GCA  GAG  AGG  TCC  CTT  GTC  CTG  GAC  AGG  CTG  GCA  AGC  AAT          96
Lys  Ile  Gly  Ala  Glu  Arg  Ser  Leu  Val  Leu  Asp  Arg  Leu  Ala  Ser  Asn
              20                        25                       30

GTC  GCC  AAA  CGT  AAG  AGC  TCT  ATG  CCT  GAC  AAA  TTT  CTT                        135
Val  Ala  Lys  Arg  Lys  Ser  Ser  Met  Pro  Asp  Lys  Phe  Leu
              35                        40                       45
```

( 2 ) INFORMATION FOR SEQ ID NO:171:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:171:

```
Val  Ile  Lys  Glu  Glu  Thr  Asn  His  Asn  Glu  Met  Ala  Glu  Asp  Leu  Cys
 1              5                        10                       15

Lys  Ile  Gly  Ala  Glu  Arg  Ser  Leu  Val  Leu  Asp  Arg  Leu  Ala  Ser  Asn
              20                        25                       30

Val  Ala  Lys  Arg  Lys  Ser  Ser  Met  Pro  Asp  Lys  Phe  Leu
              35                        40                       45
```

( 2 ) INFORMATION FOR SEQ ID NO:172:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..135

( x i ) SEQUENCE DESCRIPTION: SEQ ID NO:172:

```
GTC  ATT  AAA  GAA  GAA  ACT  AAG  CAC  AGT  GAA  ATG  GCA  GAA  GAC  CTG  TGC          48
Val  Ile  Lys  Glu  Glu  Thr  Lys  His  Ser  Glu  Met  Ala  Glu  Asp  Leu  Cys
 1              5                        10                       15

AAG  ATA  GGA  TCA  GAG  AGA  TCT  CTC  GTG  CTG  GAC  AGA  CTA  GCA  AGT  AAT          96
Lys  Ile  Gly  Ser  Glu  Arg  Ser  Leu  Val  Leu  Asp  Arg  Leu  Ala  Ser  Asn
```

|  |  | 20 |  |  |  | 25 |  |  |  | 30 |  |  |
|--|--|--|--|--|--|--|--|--|--|--|--|--|

```
GTC  GCC  AAA  CGT  AAG  AGC  TCT  ATG  CCT  CAG  AAA  TTT  CTT          135
Val  Ala  Lys  Arg  Lys  Ser  Ser  Met  Pro  Gln  Lys  Phe  Leu
          35                      40                      45
```

(2) INFORMATION FOR SEQ ID NO:173:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:173:

```
Val  Ile  Lys  Glu  Glu  Thr  Lys  His  Ser  Glu  Met  Ala  Glu  Asp  Leu  Cys
 1                  5                       10                          15

Lys  Ile  Gly  Ser  Glu  Arg  Ser  Leu  Val  Leu  Asp  Arg  Leu  Ala  Ser  Asn
               20                       25                       30

Val  Ala  Lys  Arg  Lys  Ser  Ser  Met  Pro  Gln  Lys  Phe  Leu
          35                      40                      45
```

(2) INFORMATION FOR SEQ ID NO:174:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:174:

```
Val  Ile  Lys  Glu  Glu  Thr  Xaa  His  Xaa  Glu  Met  Ala  Glu  Asp  Leu  Cys
 1                  5                       10                          15

Lys  Ile  Gly  Xaa  Glu  Arg  Ser  Leu  Val  Leu  Asp  Arg  Leu  Ala  Ser  Asn
               20                       25                       30

Val  Ala  Lys  Arg  Lys  Ser  Ser  Met  Pro  Gln  Lys  Phe  Leu
          35                      40                      45
```

(2) INFORMATION FOR SEQ ID NO:175:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..123

(xi) SEQUENCE DESCRIPTION: SEQ ID NO:175:

```
GTT  GGT  AAG  CCT  CAC  AAA  TGT  GGA  TAT  TGT  GGC  CGG  AGC  TAT  AAA  CAG   48
Val  Gly  Lys  Pro  His  Lys  Cys  Gly  Tyr  Cys  Gly  Arg  Ser  Tyr  Lys  Gln
 1                  5                       10                          15

CGA  AGC  TCT  TTA  GAG  GAG  CAT  AAA  GAG  CGA  TGC  CAC  AAC  TAC  TTG  GAA   96
Arg  Ser  Ser  Leu  Glu  Glu  His  Lys  Glu  Arg  Cys  His  Asn  Tyr  Leu  Glu
               20                       25                       30

AGC  ATG  GGC  CTT  CCG  GGC  GTG  TGC  CCA                                      123
Ser  Met  Gly  Leu  Pro  Gly  Val  Cys  Pro
          35                      40
```

( 2 ) INFORMATION FOR SEQ ID NO:176:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: protein ( x i ) SEQUENCE DESCRIPTION: SEQ ID NO:176:

```
Val  Gly  Lys  Pro  His  Lys  Cys  Gly  Tyr  Cys  Gly  Arg  Ser  Tyr  Lys  Gln
 1              5                        10                       15

Arg  Ser  Ser  Leu  Glu  Glu  His  Lys  Glu  Arg  Cys  His  Asn  Tyr  Leu  Glu
              20                        25                       30

Ser  Met  Gly  Leu  Pro  Gly  Val  Cys  Pro
              35                        40
```

( 2 ) INFORMATION FOR SEQ ID NO:177:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..126

( x i ) SEQUENCE DESCRIPTION: SEQ ID NO:177:

```
GTT  GGT  AAA  CCT  CAC  AAA  TGT  GGA  TAT  TGT  GGC  CGA  AGC  TAT  AAA  CAG      48
Val  Gly  Lys  Pro  His  Lys  Cys  Gly  Tyr  Cys  Gly  Arg  Ser  Tyr  Lys  Gln
 1              5                        10                       15

CGA  ACG  TCT  TTA  GAG  GAA  CAT  AAA  GAG  CGC  TGC  CAC  AAC  TAC  TTG  GAA      96
Arg  Thr  Ser  Leu  Glu  Glu  His  Lys  Glu  Arg  Cys  His  Asn  Tyr  Leu  Glu
              20                        25                       30

AGC  ATG  GGC  CTT  CCG  GGC  ACA  CTG  TAC  CCA                                   126
Ser  Met  Gly  Leu  Pro  Gly  Thr  Leu  Tyr  Pro
              35                        40
```

( 2 ) INFORMATION FOR SEQ ID NO:178:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:178:

```
Val  Gly  Lys  Pro  His  Lys  Cys  Gly  Tyr  Cys  Gly  Arg  Ser  Tyr  Lys  Gln
 1              5                        10                       15

Arg  Thr  Ser  Leu  Glu  Glu  His  Lys  Glu  Arg  Cys  His  Asn  Tyr  Leu  Glu
              20                        25                       30

Ser  Met  Gly  Leu  Pro  Gly  Thr  Leu  Tyr  Pro
              35                        40
```

( 2 ) INFORMATION FOR SEQ ID NO:179:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..168

( x i ) SEQUENCE DESCRIPTION: SEQ ID NO:179:

| GGT | GAA | CGG | CCT | TTC | CAG | TGC | AAC | CAG | TCT | GGG | GCC | TCC | TTT | ACC | CAG | 48 |
|---|---|---|---|---|---|---|---|---|---|---|---|---|---|---|---|---|
| Gly | Glu | Arg | Pro | Phe | Gln | Cys | Asn | Gln | Ser | Gly | Ala | Ser | Phe | Thr | Gln | |
| 1 | | | | 5 | | | | | 10 | | | | | 15 | | |

| AAA | GGC | AAC | CTC | CTG | CGG | CAC | ATC | AAG | CTG | CAC | TCG | GGT | GAG | AAG | CCC | 96 |
|---|---|---|---|---|---|---|---|---|---|---|---|---|---|---|---|---|
| Lys | Gly | Asn | Leu | Leu | Arg | His | Ile | Lys | Leu | His | Ser | Gly | Glu | Lys | Pro | |
| | | | 20 | | | | | 25 | | | | | 30 | | | |

| TTC | AAA | TGC | CAT | CTT | TGC | AAC | TAT | GCC | TGC | CGC | CGG | AGG | GAC | GCC | CTC | 144 |
|---|---|---|---|---|---|---|---|---|---|---|---|---|---|---|---|---|
| Phe | Lys | Cys | His | Leu | Cys | Asn | Tyr | Ala | Cys | Arg | Arg | Arg | Asp | Ala | Leu | |
| | | 35 | | | | | 40 | | | | | 45 | | | | |

| ACC | GGC | CAC | CTG | AGG | ACG | CAC | TCC | 168 |
|---|---|---|---|---|---|---|---|---|
| Thr | Gly | His | Leu | Arg | Thr | His | Ser | |
| 50 | | | | | | 55 | | |

( 2 ) INFORMATION FOR SEQ ID NO:180:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:180:

| Gly | Glu | Arg | Pro | Phe | Gln | Cys | Asn | Gln | Ser | Gly | Ala | Ser | Phe | Thr | Gln |
|---|---|---|---|---|---|---|---|---|---|---|---|---|---|---|---|
| 1 | | | | 5 | | | | | 10 | | | | | 15 | |

| Lys | Gly | Asn | Leu | Leu | Arg | His | Ile | Lys | Leu | His | Ser | Gly | Glu | Lys | Pro |
|---|---|---|---|---|---|---|---|---|---|---|---|---|---|---|---|
| | | | 20 | | | | | 25 | | | | | 30 | | |

| Phe | Lys | Cys | His | Leu | Cys | Asn | Tyr | Ala | Cys | Arg | Arg | Arg | Asp | Ala | Leu |
|---|---|---|---|---|---|---|---|---|---|---|---|---|---|---|---|
| | | 35 | | | | | 40 | | | | | 45 | | | |

| Thr | Gly | His | Leu | Arg | Thr | His | Ser |
|---|---|---|---|---|---|---|---|
| 50 | | | | | | 55 | |

( 2 ) INFORMATION FOR SEQ ID NO:181:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..168

( x i ) SEQUENCE DESCRIPTION: SEQ ID NO:181:

| GGA | GAA | CGG | CCC | TTC | CAG | TGC | AAT | CAG | TGC | GGG | GCC | TCA | TTC | ACC | CAG | 48 |
|---|---|---|---|---|---|---|---|---|---|---|---|---|---|---|---|---|
| Gly | Glu | Arg | Pro | Phe | Gln | Cys | Asn | Gln | Cys | Gly | Ala | Ser | Phe | Thr | Gln | |
| 1 | | | | 5 | | | | | 10 | | | | | 15 | | |

| AAG | GGC | AAC | CTG | CTC | CGG | CAC | ATC | AAG | CTG | CAT | TCC | GGG | GAG | AAG | CCC | 96 |
|---|---|---|---|---|---|---|---|---|---|---|---|---|---|---|---|---|
| Lys | Gly | Asn | Leu | Leu | Arg | His | Ile | Lys | Leu | His | Ser | Gly | Glu | Lys | Pro | |
| | | | 20 | | | | | 25 | | | | | 30 | | | |

| TTC | AAA | TGC | CAC | CTC | TGC | AAC | TAC | GCC | TGC | CGC | CGG | AGG | GAC | GCC | CTC | 144 |
|---|---|---|---|---|---|---|---|---|---|---|---|---|---|---|---|---|
| Phe | Lys | Cys | His | Leu | Cys | Asn | Tyr | Ala | Cys | Arg | Arg | Arg | Asp | Ala | Leu | |
| | | 35 | | | | | 40 | | | | | 45 | | | | |

| ACT | GGC | CAC | CTG | AGG | ACG | CAC | TCC | 168 |
|---|---|---|---|---|---|---|---|---|
| Thr | Gly | His | Leu | Arg | Thr | His | Ser | |
| 50 | | | | | | 55 | | |

( 2 ) INFORMATION FOR SEQ ID NO:182:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:182:

```
Gly  Glu  Arg  Pro  Phe  Gln  Cys  Asn  Gln  Cys  Gly  Ala  Ser  Phe  Thr  Gln
 1                   5                        10                       15
Lys  Gly  Asn  Leu  Leu  Arg  His  Ile  Lys  Leu  His  Ser  Gly  Glu  Lys  Pro
              20                        25                       30
Phe  Lys  Cys  His  Leu  Cys  Asn  Tyr  Ala  Cys  Arg  Arg  Arg  Asp  Ala  Leu
         35                        40                       45
Thr  Gly  His  Leu  Arg  Thr  His  Ser
         50                        55
```

( 2 ) INFORMATION FOR SEQ ID NO:183:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:183:

```
Gly  Glu  Arg  Pro  Phe  Gln  Cys  Asn  Gln  Cys  Gly  Ala  Ser  Phe  Thr  Gln
 1                   5                        10                       15
Lys  Gly  Asn  Leu  Leu  Arg  His  Ile  Lys  Leu  His  Ser  Gly  Glu  Lys  Pro
              20                        25                       30
Phe  Lys  Cys  His  Leu  Cys  Asn  Tyr  Ala  Cys  Arg  Arg  Arg  Asp  Ala  Leu
         35                        40                       45
Thr  Gly  His  Leu  Arg  Thr  His  Ser
         50                        55
```

( 2 ) INFORMATION FOR SEQ ID NO:184:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..255

( x i ) SEQUENCE DESCRIPTION: SEQ ID NO:184:

```
AAT  GTT  AAA  GTA  GAG  ACT  CAG  AGT  GAT  GAA  GAG  AAT  GGG  CGT  GCC  TGT     48
Asn  Val  Lys  Val  Glu  Thr  Gln  Ser  Asp  Glu  Glu  Asn  Gly  Arg  Ala  Cys
 1                   5                        10                       15

GAA  ATG  AAT  GGG  GAA  GAA  TGT  GCG  GAG  GAT  TTA  CGA  ATG  CTT  GAT  GCC     96
Glu  Met  Asn  Gly  Glu  Glu  Cys  Ala  Glu  Asp  Leu  Arg  Met  Leu  Asp  Ala
              20                        25                       30

TCG  GGA  GAG  AAA  ATG  AAT  GGC  TCC  CAC  AGG  GAC  CAA  GGC  AGC  TCG  GCT    144
Ser  Gly  Glu  Lys  Met  Asn  Gly  Ser  His  Arg  Asp  Gln  Gly  Ser  Ser  Ala
         35                        40                       45

TTG  TCG  GGA  GTT  GGA  GGC  ATT  CGA  CTT  CCT  AAC  GGA  AAA  CTA  AAG  TGT    192
```

```
Leu  Ser  Gly  Val  Gly  Gly  Ile  Arg  Leu  Pro  Asn  Gly  Lys  Leu  Lys  Cys
          50                        55                       60

GAT  ATC  TGT  GGG  ATC  ATT  TGC  ATC  GGG  CCC  AAT  GTG  CTC  ATG  GTT  CAC    240
Asp  Ile  Cys  Gly  Ile  Ile  Cys  Ile  Gly  Pro  Asn  Val  Leu  Met  Val  His
 65                      70                       75                        80

AAA  AGA  AGC  CAC  ACT                                                            255
Lys  Arg  Ser  His  Thr
                     85
```

( 2 ) INFORMATION FOR SEQ ID NO:185:

( i ) SEQUENCE CHARACTERISTICS:
        ( A ) LENGTH: 85 amino acids
        ( B ) TYPE: amino acid
        ( D ) TOPOLOGY: linear ( i i ) MOLECULE TYPE: protein ( x i ) SEQUENCE DESCRIPTION: SEQ ID NO:185:

```
Asn  Val  Lys  Val  Glu  Thr  Gln  Ser  Asp  Glu  Glu  Asn  Gly  Arg  Ala  Cys
 1               5                        10                       15

Glu  Met  Asn  Gly  Glu  Glu  Cys  Ala  Glu  Asp  Leu  Arg  Met  Leu  Asp  Ala
               20                       25                       30

Ser  Gly  Glu  Lys  Met  Asn  Gly  Ser  His  Arg  Asp  Gln  Gly  Ser  Ser  Ala
                35                       40                       45

Leu  Ser  Gly  Val  Gly  Gly  Ile  Arg  Leu  Pro  Asn  Gly  Lys  Leu  Lys  Cys
          50                        55                       60

Asp  Ile  Cys  Gly  Ile  Ile  Cys  Ile  Gly  Pro  Asn  Val  Leu  Met  Val  His
 65                      70                       75                        80

Lys  Arg  Ser  His  Thr
                     85
```

( 2 ) INFORMATION FOR SEQ ID NO:186:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..270

( x i ) SEQUENCE DESCRIPTION: SEQ ID NO:186:

```
GCC  AGT  AAT  GTT  AAA  GTA  GAG  ACT  CAG  AGT  GAT  GAA  GAG  AAT  GGG  CGT     48
Ala  Ser  Asn  Val  Lys  Val  Glu  Thr  Gln  Ser  Asp  Glu  Glu  Asn  Gly  Arg
 1                    5                        10                       15

GCC  TGT  GAA  ATG  AAT  GGG  GAA  GAA  TGT  GCA  GAG  GAT  TTA  CGA  ATG  CTT     96
Ala  Cys  Glu  Met  Asn  Gly  Glu  Glu  Cys  Ala  Glu  Asp  Leu  Arg  Met  Leu
                      20                       25                       30

GAT  GCC  TCG  GGA  GAG  AAA  ATG  AAT  GGC  TCC  CAC  AGG  GAC  CAA  GGC  AGC    144
Asp  Ala  Ser  Gly  Glu  Lys  Met  Asn  Gly  Ser  His  Arg  Asp  Gln  Gly  Ser
               35                        40                       45

TCG  GCT  TTG  TCA  GGA  GTT  GGA  GGC  ATT  CGA  CTT  CCT  AAC  GGA  AAA  CTA    192
Ser  Ala  Leu  Ser  Gly  Val  Gly  Gly  Ile  Arg  Leu  Pro  Asn  Gly  Lys  Leu
           50                        55                       60

AAG  TGT  GAT  ATC  TGT  GGG  ATC  TGT  GGG  ATC  GTT  TGC  ATC  GGG  CCC  AAT    240
Lys  Cys  Asp  Ile  Cys  Gly  Ile  Cys  Gly  Ile  Val  Cys  Ile  Gly  Pro  Asn
 65                      70                       75                       80

GTG  CTC  ATG  GTT  CAC  AAA  AGA  AGT  CAT  ACT                                  270
Val  Leu  Met  Val  His  Lys  Arg  Ser  His  Thr
```

85 90

( 2 ) INFORMATION FOR SEQ ID NO:187:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:187:

```
Ala Ser Asn Val Lys Val Glu Thr Gln Ser Asp Glu Glu Asn Gly Arg
 1               5                  10                  15
Ala Cys Glu Met Asn Gly Glu Glu Cys Ala Glu Asp Leu Arg Met Leu
            20                  25                  30
Asp Ala Ser Gly Glu Lys Met Asn Gly Ser His Arg Asp Gln Gly Ser
         35                  40                  45
Ser Ala Leu Ser Gly Val Gly Gly Ile Arg Leu Pro Asn Gly Lys Leu
     50                  55                  60
Lys Cys Asp Ile Cys Gly Ile Cys Gly Ile Val Cys Ile Gly Pro Asn
 65                  70                  75                  80
Val Leu Met Val His Lys Arg Ser His Thr
                 85                  90
```

( 2 ) INFORMATION FOR SEQ ID NO:188:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:188:

```
Ala Ser Asn Val Lys Val Glu Thr Gln Ser Asp Glu Glu Asn Gly Arg
 1               5                  10                  15
Ala Cys Glu Met Asn Gly Glu Glu Cys Ala Glu Asp Leu Arg Met Leu
            20                  25                  30
Asp Ala Ser Gly Glu Lys Met Asn Gly Ser His Arg Asp Gln Gly Ser
         35                  40                  45
Ser Ala Leu Ser Gly Val Gly Gly Ile Arg Leu Pro Asn Gly Lys Leu
     50                  55                  60
Lys Cys Asp Ile Cys Gly Ile Xaa Cys Ile Gly Pro Asn Val Leu Met
 65                  70                  75                  80
Val His Lys Arg Ser His Thr
                 85
```

( 2 ) INFORMATION FOR SEQ ID NO:189:

( i ) SEQUENCE CHARACTERISTICS:
        ( A ) LENGTH: 159 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..159

( x i ) SEQUENCE DESCRIPTION: SEQ ID NO:189:

| ATG | GAT | GTC | GAT | GAG | GGT | CAA | GAC | ATG | TCC | CAA | GTT | TCA | GGA | AAG | GAG | 48 |
| Met | Asp | Val | Asp | Glu | Gly | Gln | Asp | Met | Ser | Gln | Val | Ser | Gly | Lys | Glu | |
| 1 | | | | 5 | | | | | 10 | | | | | 15 | | |

| AGC | CCC | CCA | GTC | AGT | GAC | ACT | CCA | GAT | GAA | GGG | GAT | GAG | CCC | ATG | CCT | 96 |
| Ser | Pro | Pro | Val | Ser | Asp | Thr | Pro | Asp | Glu | Gly | Asp | Glu | Pro | Met | Pro | |
| | | | 20 | | | | | 25 | | | | | 30 | | | |

| GTC | CCT | GAG | GAC | CTG | TCC | ACT | ACC | TCT | GGA | GCA | CAG | CAG | AAC | TCC | AAG | 144 |
| Val | Pro | Glu | Asp | Leu | Ser | Thr | Thr | Ser | Gly | Ala | Gln | Gln | Asn | Ser | Lys | |
| | | 35 | | | | | 40 | | | | | 45 | | | | |

| AGT | GAT | CGA | GGC | ATG | | | | | | | | | | | | 159 |
| Ser | Asp | Arg | Gly | Met | | | | | | | | | | | | |
| 50 | | | | | | | | | | | | | | | | |

( 2 ) INFORMATION FOR SEQ ID NO:190:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:190:

| Met | Asp | Val | Asp | Glu | Gly | Gln | Asp | Met | Ser | Gln | Val | Ser | Gly | Lys | Glu |
| 1 | | | | 5 | | | | | 10 | | | | | 15 | |

| Ser | Pro | Pro | Val | Ser | Asp | Thr | Pro | Asp | Glu | Gly | Asp | Glu | Pro | Met | Pro |
| | | | 20 | | | | | 25 | | | | | 30 | | |

| Val | Pro | Glu | Asp | Leu | Ser | Thr | Thr | Ser | Gly | Ala | Gln | Gln | Asn | Ser | Lys |
| | | 35 | | | | | 40 | | | | | 45 | | | |

| Ser | Asp | Arg | Gly | Met |
| 50 | | | | |

( 2 ) INFORMATION FOR SEQ ID NO:191:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:191:

| Val | Gly | Lys | Pro | His | Lys | Cys | Gly | Tyr | Cys | Gly | Arg | Ser | Tyr | Lys | Gln |
| 1 | | | | 5 | | | | | 10 | | | | | 15 | |

| Arg | Xaa | Ser | Leu | Glu | Glu | His | Lys | Glu | Arg | Cys | His | Asn | Tyr | Leu | Glu |
| | | | 20 | | | | | 25 | | | | | 30 | | |

| Ser | Met | Gly | Leu | Pro | Gly | Xaa | Xaa | Xaa | Pro |
| | | 35 | | | | | 40 | | |